(12) United States Patent
Lei et al.

(10) Patent No.: US 11,293,015 B2
(45) Date of Patent: Apr. 5, 2022

(54) DIELS-ALDERASE AND USE THEREOF

(71) Applicants: Peking University, Beijing (CN); Institute of Materia Medica, Chinese Academy of Medical Sciences and Peking Union Medical College, Beijing (CN)

(72) Inventors: Xiaoguang Lei, Beijing (CN); Jungui Dai, Beijing (CN); Lei Gao, Beijing (CN); Cong Su, Beijing (CN)

(73) Assignees: Peking University, Beijing (CN); Institute of Materia Medica, Chinese Academy of Medical Sciences and Peking Union Medical College, Beijing (CN)

( * ) Notice: Subject to any disclaimer, the term of this patent is extended or adjusted under 35 U.S.C. 154(b) by 0 days.

(21) Appl. No.: 16/951,916

(22) Filed: Nov. 18, 2020

(65) Prior Publication Data

US 2021/0147820 A1     May 20, 2021

(51) Int. Cl.
  *C12N 9/50* (2006.01)
  *C12P 7/26* (2006.01)
  *C12P 17/04* (2006.01)

(52) U.S. Cl.
  CPC ............... *C12N 9/50* (2013.01); *C12P 7/26* (2013.01); *C12P 17/04* (2013.01)

(58) Field of Classification Search
  CPC ... C12N 9/10; C12N 9/50; C12P 17/04; C12P 7/26
  See application file for complete search history.

(56) References Cited

PUBLICATIONS

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Gao , et al., "Enantioselective Total Syntheses of Kiwanon X, Kuwanon Y, and Kuwanol A", Org. Lett. 2016, 18, 360-363.
Han , et al., "Enantioselective Biomimetic Total Syntheses of Kuwanons I and J and Brosimones A and B", Angew. Chem. Int. Ed. 2014, 53, 9257-9261.
Lee , et al., "An Efficient and Rapid Synthetic Route to Biologically Interesting Pyranochalcone Natural Products", Molecules, 2007, 12, 1420-1429.
Romano , et al., "A Short Synthesis of Morachalcone A", Tetrahedron Letters 46 (2005) 2323-2326.
Takasugi , et al., "Chalcomoracin, A Natural Diels-Alder Adduct from Diseased Mulberry", Chemistry Letters, pp. 1573-1576, 1980, The Chemical Society of Japan.

* cited by examiner

*Primary Examiner* — Ganapathirama Raghu
(74) *Attorney, Agent, or Firm* — Armstrong Teasdale LLP

(57) ABSTRACT

The present invention provides a Diels-Alderase and use thereof, and belongs to the field of gene engineering technology. The Diels-Alderase is MaDA, and its amino acid sequence and gene sequence are represented by SEQ ID Nos. 1 and 2, respectively. The present invention also provides MaDA-1 and MaDA-2, both of which are homologous proteins of MaDA, and their amino acid sequences are represented by SEQ ID Nos. 10 and 12, respectively. The present invention has discovered that MaDA and its homologous proteins from *Morus alba* can stereospecifically synthesize natural products of endo configuration, and prepare D-A type natural products and their analogs in vitro using chalcones and dehydroprenyl-containing compounds as substrates, which helps to develop and utilize the medicinal value of such natural products, and also provides a possibility to synthesize other six-membered ring-containing important chemical precursors or natural products.

8 Claims, 14 Drawing Sheets

Specification includes a Sequence Listing.

Figure 5

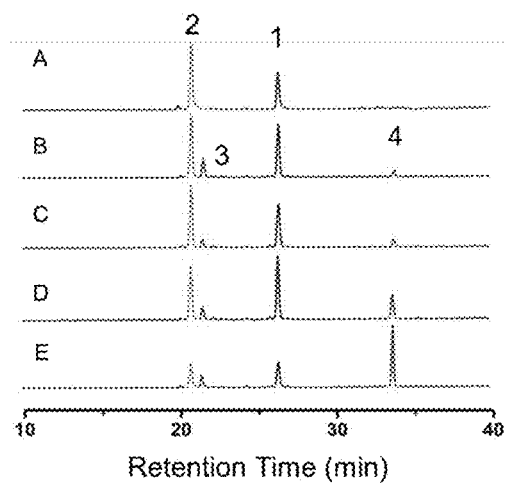

Figure 6

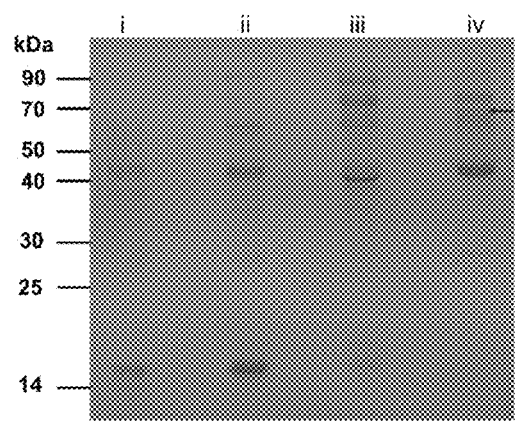

Figure 7

| Accession number | Protein description | Mascot score | MW | Matched queries | Matched peptides |
|---|---|---|---|---|---|
| EXB75193.1 | Reticuline oxidase-like protein [Morus notabilis] | 3144 | 59287 | 112 | 37 |
| EXC54351.1 | putative inactive purple acid phosphatase 2 [Morus notabilis] | 2141 | 78075 | 75 | 26 |
| EXB75194.1 | Reticuline oxidase-like protein [Morus notabilis] | 1887 | 61525 | 63 | 20 |
| EXB88234.1 | L-ascorbate oxidase-like protein [Morus notabilis] | 1704 | 60294 | 49 | 20 |
| EXC35209.1 | 2,3-bisphosphoglycerate-independent phosphoglycerate mutase [Morus notabilis] | 1381 | 61046 | 43 | 20 |
| EXC06703.1 | putative glucan 1,3-beta-glucosidase A [Morus notabilis] | 783 | 58208 | 31 | 16 |
| EXB95367.1 | L-ascorbate oxidase-like protein [Morus notabilis] | 669 | 61263 | 22 | 10 |
| EXB54433.1 | Flavonoid 3'-monooxygenase [Morus notabilis] | 537 | 92392 | 16 | 4 |
| EXB75197.1 | Reticuline oxidase-like protein [Morus notabilis] | 460 | 59923 | 15 | 2 |
| EXB53549.1 | Beta-galactosidase 10 [Morus notabilis] | 441 | 67611 | 14 | 8 |
| EXB69118.1 | 66 kDa stress protein [Morus notabilis] | 376 | 44798 | 8 | 5 |

Figure 8

| Transcript ID | FPKM | Automatic annotation |
|---|---|---|
| CL5271.Contig4_MaL_022 | 200.38 | sp|A6P6V9|CBDAS_CANSA/1.4e-61/Cannabidiolic acid synthase OS=Cannabis sativa GN=CBDAS PE=1 SV=1 |
| CL1657.Contig4_MaL_022 | 130.8 | sp|A6P6V9|CBDAS_CANSA/8.2e-61/Cannabidiolic acid synthase OS=Cannabis sativa GN=CBDAS PE=1 SV=1 |
| CL696.Contig2_MaL_022 | 72.02 | sp|Q8GTB6|THCAS_CANSA/8.0e-89/Tetrahydrocannabinolic acid synthase OS=Cannabis sativa PE=1 SV=1 |
| CL1657.Contig3_MaL_022 | 55.51 | sp|A6P6V9|CBDAS_CANSA/1.8e-63/Cannabidiolic acid synthase OS=Cannabis sativa GN=CBDAS PE=1 SV=1 |
| CL5084.Contig2_MaL_022 | 49.47 | sp|Q9SVG4|RETOL_ARATH/2.7e-194/Reticuline oxidase-like protein OS=Arabidopsis thaliana GN=At4g20830 PE=1 SV=2 |
| CL3237.Contig1_MaL_022 | 49.43 | sp|A6P6V9|CBDAS_CANSA/3.0e-92/Cannabidiolic acid synthase OS=Cannabis sativa GN=CBDAS PE=1 SV=1 |
| CL4607.Contig2_MaL_022 | 31.46 | sp|Q8GTB6|THCAS_CANSA/1.0e-140/Tetrahydrocannabinolic acid synthase OS=Cannabis sativa PE=1 SV=1 |
| CL4607.Contig1_MaL_022 | 26.07 | sp|Q8GTB6|THCAS_CANSA/5.6e-140/Tetrahydrocannabinolic acid synthase OS=Cannabis sativa PE=1 SV=1 |
| CL5271.Contig1_MaL_022 | 18.01 | sp|A6P6V9|CBDAS_CANSA/3.1e-93/Cannabidiolic acid synthase OS=Cannabis sativa GN=CBDAS PE=1 SV=1 |
| CL5084.Contig1_MaL_022 | 17.77 | sp|Q9SVG4|RETOL_ARATH/1.3e-188/Reticuline oxidase-like protein OS=Arabidopsis thaliana GN=At4g20830 PE=1 SV=2 |
| CL5271.Contig3_MaL_022 | 16.75 | sp|A6P6V9|CBDAS_CANSA/7.7e-154/Cannabidiolic acid synthase OS=Cannabis sativa GN=CBDAS PE=1 SV=1 |
| CL4729.Contig1_MaL_022 | 14.26 | sp|Q8GTB6|THCAS_CANSA/3.8e-75/Tetrahydrocannabinolic acid synthase OS=Cannabis sativa PE=1 SV=1 |
| CL696.Contig1_MaL_022 | 12.35 | sp|Q8GTB6|THCAS_CANSA/1.9e-68/Tetrahydrocannabinolic acid synthase OS=Cannabis sativa PE=1 SV=1 |
| Unigene20947_MaL_022 | 12.03 | sp|Q9SVG4|RETOL_ARATH/4.6e-156/Reticuline oxidase-like protein OS=Arabidopsis thaliana GN=At4g20830 PE=1 SV=2 |

Figure 17

```
MaDA-1   DQIGHEGFLKCLITKISKSNSTSTSESIIYTQNNPSYSTILTSTMQNPRFLSLPIPKPFV
MaDA     -NDTHEAFLECLTTRIP-SNSTFTPQSIIYTPDNPSYSTILDSTTQNPRFLSSSTRNPFA
         : **.**:**  ***. **** *.:*****.:********* ** *******.   :**.

MaDA-1   IVTPLHVSHVQATLYCAKKHDIQIRIRSGGHDYEGLSYMSNVTFVILDLRNLSSINIDVK
MaDA     IITPLHASHIQAALYCSQKHGEQMRIRSGGHDYEGLSYQSSVPFFILDLRNLSSISIDAK
         *:****.**:**:****::***.  *:*************** *. *. *.*******.** *

MaDA-1   RKSAWVQSGATIGELYYRIAEKSLSLAFPGGLGHTIGVGGQLGGGGYGYSTRKYGLASDN
MaDA     SKSAWVQAGATIGELYYGIAKTSLNLSFPGGVAHTIGVGGQLGGGGYGYSTRKYGLASDN
         *******:********* :**.:**.*:****:. ************************

MaDA-1   IIDAQFMDVQGRILNFKSMGEDLFWAIRGGGAGSPGIVLAWKIRLVDVPTTVTVFEAVRK
MaDA     VIDAQLIDARGRILDRKTMGEDLFWAIRGGGAGSPGIVLAWKIRLVNTPSTVTIFEAVRS
         :****::*. :****:**:************************:. *:***:*****.

MaDA-1   WENNATKKFVHRYQRRIADIDKDLTIFLGFQTANTGDEQGNTKIEVLAVISATPHGSQDK
MaDA     WENNITKKFIRRYQRRASKTDEDLTIPVGFRTTSSTDEEGNERISILTIVSATPHGSKDR
         ****:****:*****  :.. ******:**:*:.. : **:** :*. :*:::*******:*:

MaDA-1   VLPLMQKEFPELGLLKEECIEMPWVRSIMHYNFFRNGEPLEVLLNRTLNFEMKAFKLKSD
MaDA     LLQLVQKEFPDLGLVSEECTEMSWVRSIIHFNLFGDEVPLEVLLNRTLNFEMKAFKLRSD
         :* *.*****:***:.***.***  **.*****:*:*:*  : *****************:**

MaDA-1   YVKEFIPDDVLEKLLGKLYEEEIGEGYIELFPYGGKMNEISESEIFFPHRAGNLYNLRYL
MaDA     YVQKPIPDDVLEKLLSKLYDEETGEGYIEFPPYGGKMSKISESEIFFPYRAGNLYNLRYM
         **::.**********.***:** ******:.*******.:.*******:**********:

MaDA-1   VSWIDDGNITRTNEHIRWVRSAYDYMTPFVSKNPRGAYLNFRDLDIGINSDEDDYNYVAQ
MaDA     VSWKDDGNITRTNMHLSWIKDAYDYMTPYVSKDPRGAYLNFRDLDIGVNVNESDYDYVAK
         *** *********  *: *::. *******:****:***********:* :*.**:***:

MaDA-1   ASIWGTKYFKSNFYRLVYVKTLVDPTNFFTYEQSIPPLSPHYK--
MaDA     ASVWGTKYFRNNFYRLVDIKTIVDPTNFFKYEQSIPPLPPLHSAM
         **:******:.****** :**:******.********.*:*  :.
```

Figure 19

```
MaDA-2    ---HEEFLQCLSSRIP--------KSIIYASNNPSYSNVLDSTTQNPRFLSSSTRNPSVIV
MaDA      NDTHEAFLECLTTRIPSNSTFTPQSIIYTPDNPSYSTILDSTTQNPRFLSSSTRNPFAII
          **  **;**;:***          :****:.;*****.;*******************. *;

MaDA-2    TPFKISHIQPTIYCSKKHGVQIRIRSGGHDYEGLSYQSSVPFFILDLRNINSIQVDVEKK
MaDA      TPLHASHIQAALYCSQKHGEQMRIRSGGHDYEGLSYQSSVPFFILDLRNLSSISIDAKSK
          **:;; ****. ;;***:***  *;*************************;.**,;*.;.*

MaDA-2    SAWVEAGATLGELYYSIAKKSKTLGFPGGLCSTVGVGGQLGGGGYGYQSRTYGLASDNII
MaDA      SAWVQAGATIGELYYGIAKTSLNLSFPGGVAHTIGVGGQLGGGGYGYSTRKYGLASDNVI
          ****;****;*****.***.* ,*.****;.  *;**************,;*.*******;*

MaDA-2    DAQLIDARGRILNRKSMGEDLFWAIRGGGAGSFGIVIAWKVRLIDVPSTVTVFETVRMWE
MaDA      DAQLIDARGRILDRKTMGEDLFWAIRGGGAGSFGIVLAWKIRLVNTPSTVTIFEAVRSWE
          ************;**;****************;***;**;; ******;**;** **

MaDA-2    DNVTKKFVHRYQRRASNIDKDLTIFLGFRTTNTSDEQGNSKIQIITIISATFHGSRDRLL
MaDA      NNTTKKFIRRYQRRASKTDKDLTIFVGFRTTSSTDEEGNERISILTIVSATFHGSKDRLL
          ;*.****;;********:   ******;****** ,;;**;**,;*.*;**;********;****

MaDA-2    PLMQEEFPELGLGKEDFKEMSWVQSIVHYNNYKDDDPLEVLLNKTVNFEPNPFKLSDYV
MaDA      QLVQKEFPDLGLVSEECTEMSWVRSIIHFNLFGDEVPLEVLLNRTLNFEMKAPKLRSDYV
          *;*;***;***  .*; ,****;**;*;*  ; *; ********;*;**** ;.***;****

MaDA-2    KKPIPDDVLEKLLARLYEEDIGYDFVEFFPYGGKLSEISESEIPFPHRAGNLYNLRYMAS
MaDA      QKPIPDDVLEKLLSKLYDEETGEGYIEFFPYGGKMSKISESEIPFPYRAGNLYNLRYMVS
          ;************;;**;*; *  ,;;********;*;**********;**********.*

MaDA-2    WKQGENTTRINNHLSWVKSVYDSMTPYVSKNPRGAYLNFRDLDIGVNPNESDPTSAYNYV
MaDA      WKDDGNITRTNMHLSWIKDAYDYMTPYVSKDPRGAYLNFRDLDIGVNVNESD----YDYV
          **;.  * ** *  ****;;.. **  *******;***************  ****    *;**

MaDA-2    KQASVWGTKYFKNNFYKMVFIKTLVDPTNFFTYEQSIPPILHH-----
MaDA      AKASVWGTKYFRNNFYRLVDIKTIVDPTNFFKYEQSIPPLPPLHSAM
          ;*********;****;;*  ***;******. *******;
```

Figure 21
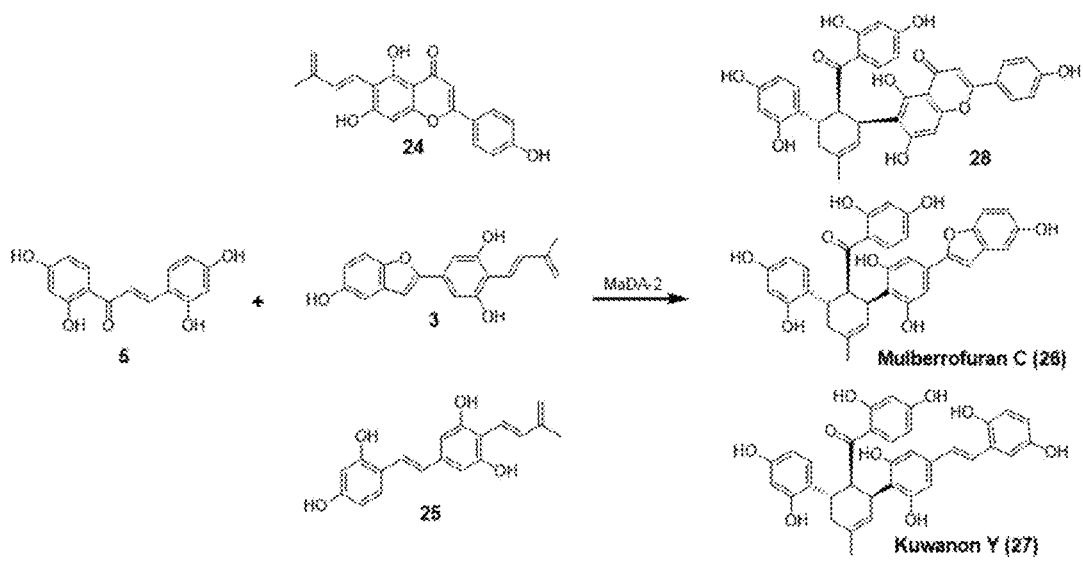
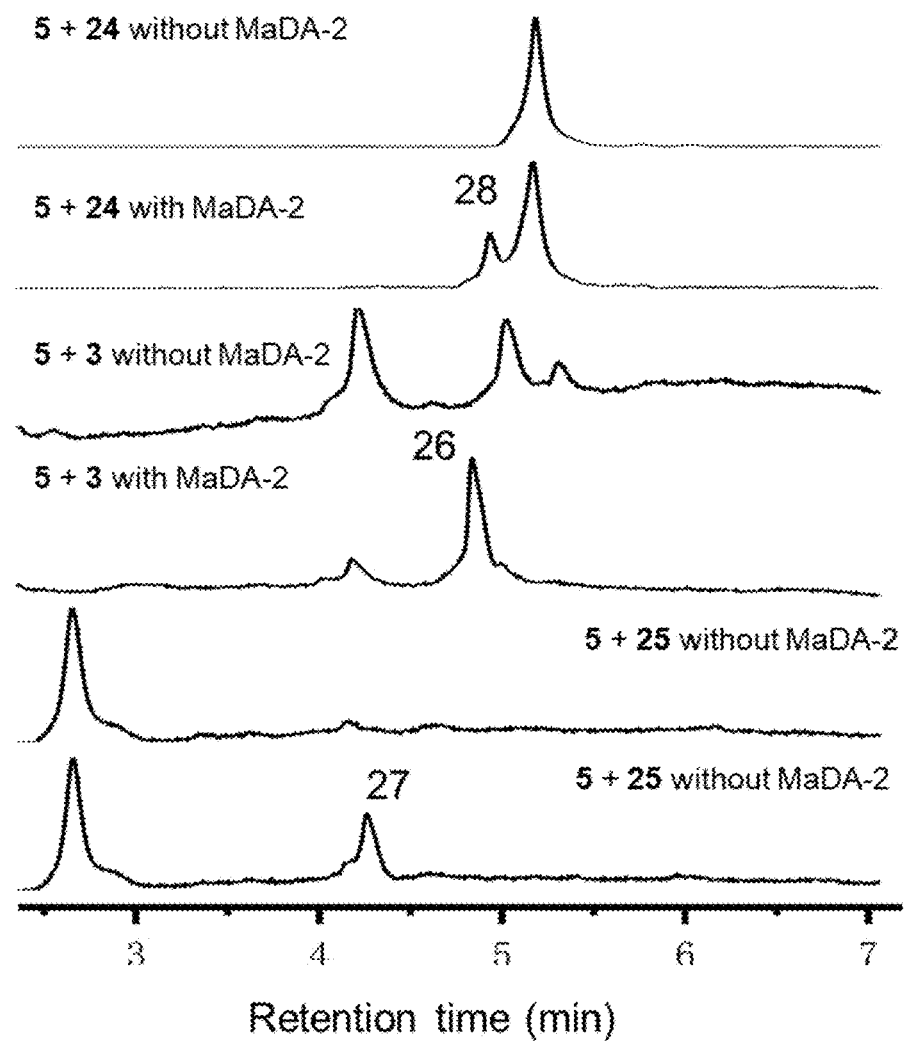

SEQUENCE LISTING

<160> NUMBER OF SEQ ID NOS: 27

<210> SEQ ID NO 1
<211> LENGTH: 550
<212> TYPE: PRT
<213> ORGANISM: Artificial Sequence
<220> FEATURE:
<223> OTHER INFORMATION: Synthesized

<400> SEQUENCE: 1

Met Gln Tyr Phe Ser Phe Pro Ser Ser Leu Ala Lys Ile Thr Ile Phe
1               5                   10                  15

Leu Ile Phe Ser Phe Val Phe Ala Ser Ser Ala Asn Asp Thr His Glu
            20                  25                  30

```
Ala Phe Leu Glu Cys Leu Thr Thr Arg Ile Pro Ser Asn Ser Thr Phe
         35                  40                  45

Thr Pro Gln Ser Ile Ile Tyr Thr Pro Asp Asn Pro Ser Tyr Ser Thr
 50                  55                  60

Ile Leu Asp Ser Thr Thr Gln Asn Pro Arg Phe Leu Ser Ser Ser Thr
 65                  70                  75                  80

Arg Asn Pro Phe Ala Ile Ile Thr Pro Leu His Ala Ser His Ile Gln
                 85                  90                  95

Ala Ala Leu Tyr Cys Ser Gln Lys His Gly Glu Gln Met Arg Ile Arg
                100                 105                 110

Ser Gly Gly His Asp Tyr Glu Gly Leu Ser Tyr Gln Ser Ser Val Pro
            115                 120                 125

Phe Phe Ile Leu Asp Leu Arg Asn Leu Ser Ser Ile Ser Ile Asp Ala
        130                 135                 140

Lys Ser Lys Ser Ala Trp Val Gln Ala Gly Ala Thr Ile Gly Glu Leu
145                 150                 155                 160

Tyr Tyr Gly Ile Ala Lys Thr Ser Leu Asn Leu Ser Phe Pro Gly Gly
                165                 170                 175

Val Ala His Thr Ile Gly Val Gly Gly Gln Leu Gly Gly Gly Gly Tyr
            180                 185                 190

Gly Tyr Ser Thr Arg Lys Tyr Gly Leu Ala Ser Asp Asn Val Ile Asp
        195                 200                 205

Ala Gln Leu Ile Asp Ala Arg Gly Arg Ile Leu Asp Arg Lys Thr Met
210                 215                 220

Gly Glu Asp Leu Phe Trp Ala Ile Arg Gly Gly Gly Ala Gly Ser Phe
225                 230                 235                 240

Gly Ile Val Leu Ala Trp Lys Ile Arg Leu Val Asn Thr Pro Ser Thr
                245                 250                 255

Val Thr Ile Phe Glu Ala Val Arg Ser Trp Glu Asn Asn Thr Thr Lys
            260                 265                 270

Lys Phe Ile Arg Arg Tyr Gln Arg Arg Ala Ser Lys Thr Asp Lys Asp
        275                 280                 285

Leu Thr Ile Phe Val Gly Phe Arg Thr Thr Ser Thr Asp Glu Glu
290                 295                 300

Gly Asn Glu Arg Ile Ser Ile Leu Thr Ile Val Ser Ala Thr Phe His
305                 310                 315                 320

Gly Ser Lys Asp Arg Leu Leu Gln Leu Val Gln Lys Glu Phe Pro Asp
                325                 330                 335

Leu Gly Leu Val Ser Glu Glu Cys Thr Glu Met Ser Trp Val Arg Ser
            340                 345                 350

Ile Ile His Phe Asn Leu Phe Gly Asp Glu Val Pro Leu Glu Val Leu
        355                 360                 365

Leu Asn Arg Thr Leu Asn Phe Glu Met Lys Ala Phe Lys Leu Arg Ser
370                 375                 380

Asp Tyr Val Gln Lys Pro Ile Pro Asp Asp Val Leu Glu Lys Leu Leu
385                 390                 395                 400

Ser Lys Leu Tyr Asp Glu Glu Thr Gly Glu Gly Tyr Ile Glu Phe Phe
                405                 410                 415

Pro Tyr Gly Gly Lys Met Ser Lys Ile Ser Glu Ser Glu Ile Pro Phe
            420                 425                 430

Pro Tyr Arg Ala Gly Asn Leu Tyr Asn Leu Arg Tyr Met Val Ser Trp
        435                 440                 445
```

Lys Asp Asp Gly Asn Ile Thr Arg Thr Asn Met His Leu Ser Trp Ile
            450                 455                 460

Lys Asp Ala Tyr Asp Tyr Met Thr Pro Tyr Val Ser Lys Asp Pro Arg
465                 470                 475                 480

Gly Ala Tyr Leu Asn Phe Arg Asp Leu Asp Ile Gly Val Asn Val Asn
                485                 490                 495

Glu Ser Asp Tyr Asp Tyr Val Ala Lys Ala Ser Val Trp Gly Thr Lys
            500                 505                 510

Tyr Phe Arg Asn Asn Phe Tyr Arg Leu Val Asp Ile Lys Thr Ile Val
            515                 520                 525

Asp Pro Thr Asn Phe Phe Lys Tyr Glu Gln Ser Ile Pro Pro Leu Pro
530                 535                 540

Pro Leu His Ser Ala Met
545                 550

<210> SEQ ID NO 2
<211> LENGTH: 1653
<212> TYPE: DNA
<213> ORGANISM: Artificial Sequence
<220> FEATURE:
<223> OTHER INFORMATION: Synthesized

<400> SEQUENCE: 2

```
atgcagtact tttccttccc ttcatcgtta gccaaaatca ccatctttct gatcttttca      60
tttgtattcg caagttcagc taacgacact catgaagcct tcttgagtg cctgaccact       120
cgtatacct ccaactccac cttcaccccg caatccatca tctacactcc agataatccg       180
tcgtattcaa ctatattgga ttcaacgact caaaatcctc gttttctttc ttcttcgaca      240
agaaatccat ttgccatcat cacaccactt cacgcctccc acatacaagc cgctctttat      300
tgttcccaga acatggcga gcagatgaga tccgaagcg gcggccatga ttatgaaggc        360
ctttcttacc agtccagtgt gccgttttc atacttgact tgagaaactt gagttctatt      420
agtattgacg cgaagagcaa gtctgcgtgg gttcaggccg agcgacgat tggtgaactt      480
tattatggga tagctaaaac gagcctgaat cttagctttc ccggcggcgt tgctcacact    540
atcggcgttg ggggacagtt aggtggagga ggctatggct attcgacgag aaaatatggg   600
ctcgcgtccg ataacgtcat cgacgcacag ttaatcgatg ctcgaggaag aattctcgat   660
cgaaaaacca tggggaaga tttgttttgg gccatccgcg tggtggagc gggaagcttc    720
ggaatcgttc ttgcctggaa aattcgcctt gttaacacac catcgacagt gactatattt    780
gaagccgtga ggagttggga aaacaataca acaaaaaagt tcatccgtcg atatcaacgt   840
cgcgcttcca aaaccgataa ggatctaacc atcttcgtcg gattccgaac tacgagttct   900
acagatgaag aagggaatga gagaatttca atactaacta tcgtctcggc acattccac    960
ggcagcaagg ataggctcct tcagttagtg caaaaggagt ttcccgactt gggtttggtt   1020
agtgaagagt gcaccgaaat gtcatgggtt cgatccatta tccatttcaa tttattcggg   1080
gacgaagtac ccttggaggt tctactcaat agaacgctca atttcgaaat gaaggctttt   1140
aaattgagat ctgactatgt acaaaagcct attccagatg acgtgttaga aaaattattg   1200
agtaagttgt atgatgaaga gacaggagaa ggttacatcg aattttttcc ttatggagga   1260
aaaatgagta agatttcaga atctgaaatc ccgttcccat accgagccgg aaacctctac   1320
aaccttcggt acatggtgtc atggaaggat gatggaaaca ttacaagaac caacatgcat   1380
cttagctgga taaaagatgc ttacgattac atgacacctt acgtgtcaaa agatccgagg   1440
```

```
ggcgcatatc tgaacttcag agatctcgac atcggagtta atgtcaatga gagcgactac    1500
gattacgtcg cgaaagcaag cgtttgggt  actaagtatt ttaggaataa tttttataga    1560
ttagttgata taaagacaat agttgatcca actaatttct ttaaatacga gcaaagtatc    1620
ccacctcttc ctcctctaca ttcagcaatg tga                                 1653

<210> SEQ ID NO 3
<211> LENGTH: 5254
<212> TYPE: DNA
<213> ORGANISM: Artificial Sequence
<220> FEATURE:
<223> OTHER INFORMATION: Synthesized

<400> SEQUENCE: 3
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta atcgggggc  tccctttagg gttccgattt     180
agtgctttac ggcacctcga ccccaaaaaa cttgattagg gtgatggttc acgtagtggg     240
ccatcgccct gatagacggt ttttcgccct tgacgttgg  agtccacgtt ctttaatagt     300
ggactcttgt tccaaactgg aacaacactc aaccctatct cggtctattc ttttgattta     360
taagggattt tgccgatttc ggcctattgg ttaaaaaatg agctgattta caaaaattt      420 aacgcgaatt ttaacaaaat attaacgttt acaatttcag gtggcacttt tcggggaaat     480
gtgcgcggaa cccctatttg tttatttttc taaatacatt caaatatgta tccgctcatg     540
agacaataac cctgataaat gcttcaataa tattgaaaaa ggaagagtat gagtattcaa     600
catttccgtg tcgcccttat ccctttttt  gcggcatttt gccttcctgt ttttgctcac     660
ccagaaacgc tggtgaaagt aaaagatgct gaagatcagt tgggtgcacg agtgggttac     720
atcgaactgg atctcaacag cggtaagatc cttgagagtt ttcgccccga agaacgtttt     780
ccaatgatga gcacttttaa agttctgcta tgtggcgcgg tattatcccg tattgacgcc     840
gggcaagagc aactcggtcg ccgcatacac tattctcaga atgacttggt tgagtactca     900
ccagtcacag aaaagcatct tacgatggca tgacagtaa  agaaattatg cagtgctgcc     960
ataaccatga gtgataacac tgcggccaac ttacttctga caacgatcgg aggaccgaag    1020
gagctaaccg cttttttgca acatgggga  gatcatgtaa ctcgccttga tcgttgggaa    1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca gtttactca  tatatacttt agattgattt aaaacttcat    1500
ttttaattta aaaggatcta ggtgaagatc ctttttgata atctcatgac caaaatccct    1560
taacgtgagt tttcgttcca ctgagcgtca gaccccgtag aaaagatcaa aggatcttct    1620
tgagatcctt ttttttctgcg cgtaatctgc tgcttgcaaa caaaaaaacc accgctacca    1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacataccte gctctgctaa tcctgttacc agtggctgct    1860
```

```
gccagtggcg ataagtcgtg tcttaccggg ttggactcaa gacgatagtt accggataag      1920
gcgcagcggt cgggctgaac ggggggttcg tgcacacagc ccagcttgga gcgaacgacc      1980
tacaccgaac tgagatacct acagcgtgag cattgagaaa gcgccacgct tcccgaaggg      2040
agaaaggcgg acaggtatcc ggtaagcggc agggtcggaa caggagagcg cacgagggag      2100
cttccagggg gaaacgcctg gtatctttat agtcctgtcg ggtttcgcca cctctgactt      2160
gagcgtcgat ttttgtgatg ctcgtcaggg ggcggagcc tatggaaaaa cgccagcaac      2220
gcggcctttt tacggttcct ggccttttgc tggcctttg ctcacatgtt ctttcctgcg       2280
ttatcccctg attctgtgga taaccgtatt accgcctttg agtgagctga taccgctcgc      2340
cgcagccgaa cgaccgagcg cagcgagtca gtgagcgagg aagcggaaga gcgcctgatg      2400
cggtattttc tccttacgca tctgtgcggt atttcacacc gcagaccagc cgcgtaacct      2460
ggcaaaatcg gttacggttg agtaataaat ggatgccctg cgtaagcggg tgtgggcgga      2520
caataaagtc ttaaactgaa caaaatagat ctaaactatg acaataaagt cttaaactag      2580
acagaatagt tgtaaactga atcagtcca gttatgctgt gaaaaagcat actggacttt       2640
tgttatggct aaagcaaact cttcattttc tgaagtgcaa attgcccgtc gtattaaaga      2700
ggggcgtggc caagggcatg gtaaagacta tattcgcggc gttgtgacaa tttaccgaac      2760
aactccgcgg ccgggaagcc gatctcggct tgaacgaatt gttaggtggc ggtacttggg      2820
tcgatatcaa agtgcatcac ttcttcccgt atgcccaact ttgtatagag agccactgcg      2880
ggatcgtcac cgtaatctgc ttgcacgtag atcacataag caccaagcgc gttggcctca      2940
tgcttgagga gattgatgag cgcggtggca atgccctgcc tccggtgctc gccggagact      3000
gcgagatcat agatatagat ctcactacgc ggctgctcaa acctgggcag aacgtaagcc      3060
gcgagagcgc caacaaccgc ttcttggtcg aaggcagcaa gcgcgatgaa tgtcttacta      3120
cggagcaagt tcccgaggta atcggagtcc ggctgatgtt gggagtaggt ggctacatca      3180
ccgaactcac gaccgaaaag atcaagagca gcccgcatgg atttgacttg gtcagggccg      3240
agcctacatg tgcgaatgat gcccatactt gagccaccta actttgtttt agggcgactg      3300
ccctgctgcg taacatcgtt gctgctgcgt aacatcgttg ctgctccata acatcaaaca      3360
tcgacccacg gcgtaacgcg cttgctgctt ggatgcccga ggcatagact gtacaaaaaa      3420
acagtcataa caagccatga aaccgccac tgcgccgtta ccaccgctgc gttcggtcaa       3480
ggttctggac cagttgcgtg agcgcatacg ctacttgcat tacagtttac gaaccgaaca      3540
ggcttatgtc aactgggttc gtgccttcat ccgtttccac ggtgtgcgtc acccggcaac      3600
cttgggcagc agcgaagtcg aggcatttct gtcctggctg gcgaacgagc gcaaggtttc      3660
ggtctccacg catcgtcagg cattggcggc cttgctgttc ttctacggca aggtgctgtg      3720
cacggatctg ccctggcttc aggagatcgg aagacctcgg ccgtcgcggc gcttgccggt      3780
ggtgctgacc ccggatgaag tggttcgcat cctcggtttt ctggaaggcg agcatcgttt      3840
gttcgcccag gactctagct atagttctag tggttggcta cgtatactcc ggaatattaa      3900
tagatcatgg agataattaa aatgataacc atctcgcaaa taataagta ttttactgtt       3960 ttcgtaacag ttttgtaata aaaaaaccta taaatattcc ggattattca taccgtccca      4020
ccatcgggcg cggatctagg tatgctacta gtaaatcagt cacaccaagg cttcaataag      4080
gaacacacaa gcaagatggt aagcgctatt gttttatatg tgcttttggc ggcggcggcg      4140
cattctgcct ttgcggcagg tatgggtcat caccatcatc atcacgggtc cctgcaggac      4200
```

| | |
|---|---|
| tcagaagtca atcaagaagc taagccagag gtcaagccag aagtcaagcc tgagactcac | 4260 |
| atcaatttaa aggtgtccga tggatcttca gagatcttct tcaagatcaa aaagaccact | 4320 |
| cctttaagaa ggctgatgga agcgttcgct aaaagacagg gtaaggaaat ggactcctta | 4380 |
| acgttcttgt acgacggtat tgaaattcaa gctgatcaga ccctgaaga tttggacatg | 4440 |
| gaggataacg atattattga ggctcacaga gaacagattg gaggtgatta cgatatccca | 4500 |
| acgaccgaaa acctgtattt tcagggatcc ggaattcaaa ggcctacgtc gacgagctca | 4560 |
| ctagtcgcgg ccgctttcga atctagagcc tgcagtctcg aggcatgcgg taccaagctt | 4620 |
| gtcgagaagt actagaggat cataatcagc cataccacat ttgtagaggt tttacttgct | 4680 |
| ttaaaaaacc tcccacacct cccctgaac ctgaaacata aaatgaatgc aattgttgtt | 4740 |
| gttaacttgt ttattgcagc ttataatggt tacaaataaa gcaatagcat cacaaatttc | 4800 |
| acaaataaag cattttttc actgcattct agttgtggtt tgtccaaact catcaatgta | 4860 |
| tcttatcatg tctggatctg atcactgctt gagcctagga gatccgaacc agataagtga | 4920 |
| aatctagttc caaactattt tgtcattttt aattttcgta ttagcttacg acgctacacc | 4980 |
| cagttcccat ctattttgtc actcttccct aaataatcct taaaaactcc atttccaccc | 5040 |
| ctcccagttc ccaactattt tgtccgccca cagcggggca ttttcttcc tgttatgttt | 5100 |
| ttaatcaaac atcctgccaa ctccatgtga caaaccgtca tcttcggcta cttttctct | 5160 |
| gtcacagaat gaaaattttt ctgtcatctc ttcgttatta atgtttgtaa ttgactgaat | 5220 |
| atcaacgctt atttgcagcc tgaatggcga atgg | 5254 |

<210> SEQ ID NO 4
<211> LENGTH: 668
<212> TYPE: PRT
<213> ORGANISM: Artificial Sequence
<220> FEATURE:
<223> OTHER INFORMATION: Synthesized

<400> SEQUENCE: 4

```
Met Val Ser Ala Ile Val Leu Tyr Val Leu Leu Ala Ala Ala Ala His
1               5                   10                  15

Ser Ala Phe Ala Ala Gly Met Gly His His His His His Gly Ser
            20                  25                  30

Leu Gln Asp Ser Glu Val Asn Gln Glu Ala Lys Pro Glu Val Lys Pro
        35                  40                  45

Glu Val Lys Pro Glu Thr His Ile Asn Leu Lys Val Ser Asp Gly Ser
    50                  55                  60

Ser Glu Ile Phe Phe Lys Ile Lys Lys Thr Thr Pro Leu Arg Arg Leu
65                  70                  75                  80

Met Glu Ala Phe Ala Lys Arg Gln Gly Lys Glu Met Asp Ser Leu Thr
                85                  90                  95

Phe Leu Tyr Asp Gly Ile Glu Ile Gln Ala Asp Gln Thr Pro Glu Asp
            100                 105                 110

Leu Asp Met Glu Asp Asn Asp Ile Ile Glu Ala His Arg Glu Gln Ile
        115                 120                 125

Gly Gly Asp Tyr Asp Ile Pro Thr Thr Glu Asn Leu Tyr Phe Gln Gly
    130                 135                 140

Ser Asn Asp Thr His Glu Ala Phe Leu Glu Cys Leu Thr Thr Arg Ile
145                 150                 155                 160

Pro Ser Asn Ser Thr Phe Thr Pro Gln Ser Ile Ile Tyr Thr Pro Asp
                165                 170                 175
```

-continued

```
Asn Pro Ser Tyr Ser Thr Ile Leu Asp Ser Thr Thr Gln Asn Pro Arg
            180                 185                 190

Phe Leu Ser Ser Ser Thr Arg Asn Pro Phe Ala Ile Ile Thr Pro Leu
        195                 200                 205

His Ala Ser His Ile Gln Ala Ala Leu Tyr Cys Ser Gln Lys His Gly
    210                 215                 220

Glu Gln Met Arg Ile Arg Ser Gly Gly His Asp Tyr Glu Gly Leu Ser
225                 230                 235                 240

Tyr Gln Ser Ser Val Pro Phe Phe Ile Leu Asp Leu Arg Asn Leu Ser
                245                 250                 255

Ser Ile Ser Ile Asp Ala Lys Ser Lys Ser Ala Trp Val Gln Ala Gly
            260                 265                 270

Ala Thr Ile Gly Glu Leu Tyr Tyr Gly Ile Ala Lys Thr Ser Leu Asn
        275                 280                 285

Leu Ser Phe Pro Gly Gly Val Ala His Thr Ile Gly Val Gly Gly Gln
    290                 295                 300

Leu Gly Gly Gly Tyr Gly Tyr Ser Thr Arg Lys Tyr Gly Leu Ala
305                 310                 315                 320

Ser Asp Asn Val Ile Asp Ala Gln Leu Ile Asp Ala Arg Gly Arg Ile
                325                 330                 335

Leu Asp Arg Lys Thr Met Gly Glu Asp Leu Phe Trp Ala Ile Arg Gly
            340                 345                 350

Gly Gly Ala Gly Ser Phe Gly Ile Val Leu Ala Trp Lys Ile Arg Leu
        355                 360                 365

Val Asn Thr Pro Ser Thr Val Thr Ile Phe Glu Ala Val Arg Ser Trp
370                 375                 380

Glu Asn Asn Thr Thr Lys Lys Phe Ile Arg Arg Tyr Gln Arg Arg Ala
385                 390                 395                 400

Ser Lys Thr Asp Lys Asp Leu Thr Ile Phe Val Gly Phe Arg Thr Thr
                405                 410                 415

Ser Ser Thr Asp Glu Glu Gly Asn Glu Arg Ile Ser Ile Leu Thr Ile
            420                 425                 430

Val Ser Ala Thr Phe His Gly Ser Lys Asp Arg Leu Leu Gln Leu Val
        435                 440                 445

Gln Lys Glu Phe Pro Asp Leu Gly Leu Val Ser Glu Glu Cys Thr Glu
    450                 455                 460

Met Ser Trp Val Arg Ser Ile Ile His Phe Asn Leu Phe Gly Asp Glu
465                 470                 475                 480

Val Pro Leu Glu Val Leu Leu Asn Arg Thr Leu Asn Phe Glu Met Lys
                485                 490                 495

Ala Phe Lys Leu Arg Ser Asp Tyr Val Gln Lys Pro Ile Pro Asp Asp
            500                 505                 510

Val Leu Glu Lys Leu Leu Ser Lys Leu Tyr Asp Glu Glu Thr Gly Glu
        515                 520                 525

Gly Tyr Ile Glu Phe Pro Tyr Gly Gly Lys Met Ser Lys Ile Ser
    530                 535                 540

Glu Ser Glu Ile Pro Phe Pro Tyr Arg Ala Gly Asn Leu Tyr Asn Leu
545                 550                 555                 560

Arg Tyr Met Val Ser Trp Lys Asp Asp Gly Asn Ile Thr Arg Thr Asn
                565                 570                 575

Met His Leu Ser Trp Ile Lys Asp Ala Tyr Asp Tyr Met Thr Pro Tyr
            580                 585                 590

Val Ser Lys Asp Pro Arg Gly Ala Tyr Leu Asn Phe Arg Asp Leu Asp
```

```
            595                 600                 605
Ile Gly Val Asn Val Asn Glu Ser Asp Tyr Asp Tyr Val Ala Lys Ala
    610                 615                 620

Ser Val Trp Gly Thr Lys Tyr Phe Arg Asn Asn Phe Tyr Arg Leu Val
625                 630                 635                 640

Asp Ile Lys Thr Ile Val Asp Pro Thr Asn Phe Phe Lys Tyr Glu Gln
                645                 650                 655

Ser Ile Pro Pro Leu Pro Pro Leu His Ser Ala Met
            660                 665

<210> SEQ ID NO 5
<211> LENGTH: 46
<212> TYPE: DNA
<213> ORGANISM: Artificial Sequence
<220> FEATURE:
<223> OTHER INFORMATION: Synthesized

<400> SEQUENCE: 5
aacctgtatt ttcagggatc caacgacact catgaagcct ttcttg                      46

<210> SEQ ID NO 6
<211> LENGTH: 50
<212> TYPE: DNA
<213> ORGANISM: Artificial Sequence
<220> FEATURE:
<223> OTHER INFORMATION: Synthesized

<400> SEQUENCE: 6
ctcgagactg caggctctag atcacattgc tgaatgtaga ggaggaagag                  50

<210> SEQ ID NO 7
<211> LENGTH: 18
<212> TYPE: DNA
<213> ORGANISM: Artificial Sequence
<220> FEATURE:
<223> OTHER INFORMATION: Synthesized

<400> SEQUENCE: 7
aaatgataac catctcgc                                                     18

<210> SEQ ID NO 8
<211> LENGTH: 24
<212> TYPE: DNA
<213> ORGANISM: Artificial Sequence
<220> FEATURE:
<223> OTHER INFORMATION: Synthesized

<400> SEQUENCE: 8
ggaggataac gatattattg aggc                                              24

<210> SEQ ID NO 9
<211> LENGTH: 1575
<212> TYPE: DNA
<213> ORGANISM: Artificial Sequence
<220> FEATURE:
<223> OTHER INFORMATION: Synthesized

<400> SEQUENCE: 9
gatcaaattg gtcatgaagg ctttcttaag tgcctgatca ctcgtatatc caaatccaac       60
tctacctcca cttctgaatc cattatctac actcaaaata atccctctta ttcaactata      120
ttgacttcaa cgatgcagaa tcctcgtttt ctttctcttc caatcccaaa accattcgtt      180
atcgtaacac cattacatgt ctcccacgtc caagccactc tttactgcgc caagaaacat      240
```

```
gacatacaaa tcagaatccg aagtggtggc catgattacg agggcctttc ttatatgtct    300
aatgtcactt ttgtcatact tgacttgaga aacttaagtt ctattaacat tgacgtgaag    360
aggaagtctg catgggttca gtccggagca accattggcg aactttatta taggattgct    420
gagaaaagcc taagtcttgc cttccctgga gggcttggcc acactattgg tgttggagga    480
cagttaggtg gaggaggcta tggctattcg acgcgaaagt acgggctcgc atctgataat    540
attattgacg cccaatttat ggacgtgcaa ggaagaattc tcaatcggaa atctatgggg    600
gaagatttgt tttgggccat acgcggtggt ggagctggaa gcttcggaat tgttctcgcc    660
tggaaaatcc gactggtgga cgtgcctacg acagtgaccg tatttgaagc cgtaaggaag    720
tgggaaaaca atgcaacaaa gaagtttgtt catcggtatc aacgccgtat tgccgacatc    780
gataaggatc taactatctt tcttggattc caaactgcga atactggcga tgaacaaggg    840
aacacgaaaa ttgaagtatt agctgtcatc tcagcaacat ttcacggcag tcaagataag    900
gtccttccat tgatgcagaa ggagtttccc gagttgggtt tgcttaaaga gaatgcata    960
gaaatgccgt gggtccgatc cattatgcat tacaactttt tccgaaacgg agagccctta   1020
gaagttctac tcaatagaac acttaatttc gagatgaagg ctttcaaatt gaaatctgac   1080
tacgtgaaag agcctattcc agatgacgtg ttggaaaaat tgttgggcaa gttgtatgag   1140
gaagaaatag gagaaggtta cattgaactt tttccttatg gagggaagat gaatgagatt   1200
tcagaatctg aaattccgtt cccacatcga gctgggaacc tctacaacct tcggtacttg   1260
gtgtcatgga tagacgatgg aaatattacg agaaccaacg agcatattcg ctgggtaaga   1320
agtgcttacg attacatgac tccttttgtt tcaaagaatc ctaggggtgc gtatctcaac   1380
ttcagagacc ttgacatcgg gattaattcc gatgaggatg attacaacta tgttgcacaa   1440
gcaagcattt ggggcactaa gtattttaaa agcaatttct ataggttggt ttatgtaaag   1500
acttttagttg atccgactaa tttctttaca tacgaacaaa gcatcccacc tctttcacca   1560
cattacaaaa ggtaa                                                    1575
```

<210> SEQ ID NO 10
<211> LENGTH: 524
<212> TYPE: PRT
<213> ORGANISM: Artificial Sequence
<220> FEATURE:
<223> OTHER INFORMATION: Synthesized

<400> SEQUENCE: 10

Asp Gln Ile Gly His Glu Gly Phe Leu Lys Cys Leu Ile Thr Arg Ile
1               5                   10                  15

Ser Lys Ser Asn Ser Thr Ser Thr Ser Glu Ser Ile Ile Tyr Thr Gln
            20                  25                  30

Asn Asn Pro Ser Tyr Ser Thr Ile Leu Thr Ser Thr Met Gln Asn Pro
        35                  40                  45

Arg Phe Leu Ser Leu Pro Ile Pro Lys Pro Phe Val Ile Val Thr Pro
    50                  55                  60

Leu His Val Ser His Val Gln Ala Thr Leu Tyr Cys Ala Lys Lys His
65                  70                  75                  80

Asp Ile Gln Ile Arg Ile Arg Ser Gly Gly His Asp Tyr Glu Gly Leu
                85                  90                  95

Ser Tyr Met Ser Asn Val Thr Phe Val Ile Leu Asp Leu Arg Asn Leu
            100                 105                 110

Ser Ser Ile Asn Ile Asp Val Lys Arg Lys Ser Ala Trp Val Gln Ser

```
            115                 120                 125
Gly Ala Thr Ile Gly Glu Leu Tyr Tyr Arg Ile Ala Glu Lys Ser Leu
        130                 135                 140

Ser Leu Ala Phe Pro Gly Gly Leu Gly His Thr Ile Gly Val Gly Gly
145                 150                 155                 160

Gln Leu Gly Gly Gly Tyr Gly Tyr Ser Thr Arg Lys Tyr Gly Leu
                165                 170                 175

Ala Ser Asp Asn Ile Ile Asp Ala Gln Phe Met Asp Val Gln Gly Arg
            180                 185                 190

Ile Leu Asn Arg Lys Ser Met Gly Glu Asp Leu Phe Trp Ala Ile Arg
            195                 200                 205

Gly Gly Gly Ala Gly Ser Phe Gly Ile Val Leu Ala Trp Lys Ile Arg
        210                 215                 220

Leu Val Asp Val Pro Thr Thr Val Thr Val Phe Glu Ala Val Arg Lys
225                 230                 235                 240

Trp Glu Asn Asn Ala Thr Lys Lys Phe Val His Arg Tyr Gln Arg Arg
                245                 250                 255

Ile Ala Asp Ile Asp Lys Asp Leu Thr Ile Phe Leu Gly Phe Gln Thr
            260                 265                 270

Ala Asn Thr Gly Asp Glu Gln Gly Asn Thr Lys Ile Glu Val Leu Ala
        275                 280                 285

Val Ile Ser Ala Thr Phe His Gly Ser Gln Asp Lys Val Leu Pro Leu
290                 295                 300

Met Gln Lys Glu Phe Pro Glu Leu Gly Leu Leu Lys Glu Glu Cys Ile
305                 310                 315                 320

Glu Met Pro Trp Val Arg Ser Ile Met His Tyr Asn Phe Phe Arg Asn
                325                 330                 335

Gly Glu Pro Leu Glu Val Leu Leu Asn Arg Thr Leu Asn Phe Glu Met
            340                 345                 350

Lys Ala Phe Lys Leu Lys Ser Asp Tyr Val Lys Glu Pro Ile Pro Asp
        355                 360                 365

Asp Val Leu Glu Lys Leu Leu Gly Lys Leu Tyr Glu Glu Ile Gly
370                 375                 380

Glu Gly Tyr Ile Glu Leu Phe Pro Tyr Gly Gly Lys Met Asn Glu Ile
385                 390                 395                 400

Ser Glu Ser Glu Ile Pro Phe Pro His Arg Ala Gly Asn Leu Tyr Asn
                405                 410                 415

Leu Arg Tyr Leu Val Ser Trp Ile Asp Asp Gly Asn Ile Thr Arg Thr
            420                 425                 430

Asn Glu His Ile Arg Trp Val Arg Ser Ala Tyr Asp Tyr Met Thr Pro
        435                 440                 445

Phe Val Ser Lys Asn Pro Arg Gly Ala Tyr Leu Asn Phe Arg Asp Leu
450                 455                 460

Asp Ile Gly Ile Asn Ser Asp Glu Asp Tyr Asn Tyr Val Ala Gln
465                 470                 475                 480

Ala Ser Ile Trp Gly Thr Lys Tyr Phe Lys Ser Asn Phe Tyr Arg Leu
                485                 490                 495

Val Tyr Val Lys Thr Leu Val Asp Pro Thr Asn Phe Phe Thr Tyr Glu
            500                 505                 510

Gln Ser Ile Pro Pro Leu Ser Pro His Tyr Lys Arg
        515                 520

<210> SEQ ID NO 11
```

<211> LENGTH: 1542
<212> TYPE: DNA
<213> ORGANISM: Artificial Sequence
<220> FEATURE:
<223> OTHER INFORMATION: Synthesized

<400> SEQUENCE: 11

| | | | | | |
|---|---|---|---|---|---|
| catgaagagt | tcttcagtg | cctgagctct | cgtatacca | agtccattat | ctatgcttca | 60 |
| aataacccct | cgtattcaaa | tgtattagat | tcgacgactc | aaaatcctcg | tttcctttct | 120 |
| tcttcgacca | gaaatccatc | tgttatcgtc | acaccgttta | aaatctccca | catacaaccc | 180 |
| accatttact | gctccaagaa | acatggcgtg | cagataagaa | ttcgaagcgg | tgggcatgat | 240 |
| tatgaaggcc | tttcttatca | gtccagtgtc | ccattttca | tactcgactt | gagaaacata | 300 |
| aattccattc | aagttgatgt | ggagaagaag | agtgcatggg | ttgaggcagg | tgcgacgctc | 360 |
| ggcgaacttt | actacagtat | cgctaaaaaa | agcaaacgc | ttggcttccc | tggcggtctt | 420 |
| tgcagcaccg | ttggtgtcgg | tggacagtta | ggtggaggag | gctatggcta | tcaatcgcga | 480 |
| acatatgggc | tcgcatctga | taatattatt | gatgcgcaat | taatcgacgc | tcgaggaaga | 540 |
| attctcaatc | ggaaatccat | ggggaggat | ttgttctggg | ccattcgcgg | tggtggagca | 600 |
| ggaagcttcg | gaattgtaat | tgcctggaag | gttcgactca | ttgacgtgcc | ttcgacagtg | 660 |
| actgtctttg | aaactgtacg | catgtgggaa | gataatgtaa | cgaagaagtt | tgttcatcga | 720 |
| tatcaacgtc | gtgcttccaa | catcgataag | gatctaacta | tcttcttggg | attccgaacc | 780 |
| acaaatacta | gtgatgaaca | agggaattca | aagattcaaa | taataaccat | catctcagcc | 840 |
| acattccatg | gcagcaggga | taggctcctt | ccattgatgc | aagaggagtt | tcccgagttg | 900 |
| ggtttgggca | agaagatttt | caaagaaatg | tcatgggtcc | aatctattgt | ccattacaat | 960 |
| aattacaaag | acgatgatcc | cttggaagtt | ctactcaaca | aaacagtcaa | tttcgaaccc | 1020 |
| aacccttca | aattgaaatc | tgactatgtg | aaaaagccta | ttccagatga | cgtgttggaa | 1080 |
| aaattgctgg | ctcggttgta | cgaagaagac | ataggatatg | attttgtgga | atttttcca | 1140 |
| tatggaggaa | aattgagcga | gatttcagaa | tctgaaatcc | cattcccaca | tcgagctgga | 1200 |
| aacctctaca | accttcggta | catggcttca | tggaaacaag | gcgaaaatac | tacaagaatc | 1260 |
| aacaaccatc | ttagctgggt | aagaagtgtt | tatgattcca | tgactcctta | tgtgtcaaag | 1320 |
| aatccaaggg | gtgcatatct | caactttaga | gaccttgaca | tcggggttaa | tcctaatgag | 1380 |
| agtgaccca | caagtgctta | taactatgtt | aaacaagcaa | gcgtttgggg | tactaagtat | 1440 |
| tttaagaaca | atttctacaa | aatggtgttt | ataaagactt | tagttgatcc | aactaatttc | 1500 |
| tttacatacg | aacaaagcat | cccacctatt | cttcaccatt | aa | | 1542 |

<210> SEQ ID NO 12
<211> LENGTH: 513
<212> TYPE: PRT
<213> ORGANISM: Artificial Sequence
<220> FEATURE:
<223> OTHER INFORMATION: Synthesized

<400> SEQUENCE: 12

His Glu Glu Phe Leu Gln Cys Leu Ser Ser Arg Ile Pro Lys Ser Ile
1               5                   10                  15

Ile Tyr Ala Ser Asn Asn Pro Ser Tyr Ser Asn Val Leu Asp Ser Thr
            20                  25                  30

Thr Gln Asn Pro Arg Phe Leu Ser Ser Ser Thr Arg Asn Pro Ser Val
        35                  40                  45

```
Ile Val Thr Pro Phe Lys Ile Ser His Ile Gln Pro Thr Ile Tyr Cys
     50                  55                  60

Ser Lys Lys His Gly Val Gln Ile Arg Ile Arg Ser Gly Gly His Asp
 65              70                  75                      80

Tyr Glu Gly Leu Ser Tyr Gln Ser Ser Val Pro Phe Phe Ile Leu Asp
                 85                  90                  95

Leu Arg Asn Ile Asn Ser Ile Gln Val Asp Val Glu Lys Lys Ser Ala
                100                 105                 110

Trp Val Glu Ala Gly Ala Thr Leu Gly Glu Leu Tyr Tyr Ser Ile Ala
                115                 120                 125

Lys Lys Ser Lys Thr Leu Gly Phe Pro Gly Gly Leu Cys Ser Thr Val
    130                 135                 140

Gly Val Gly Gly Gln Leu Gly Gly Gly Tyr Gly Tyr Gln Ser Arg
145                 150                 155                 160

Thr Tyr Gly Leu Ala Ser Asp Asn Ile Ile Asp Ala Gln Leu Ile Asp
                165                 170                 175

Ala Arg Gly Arg Ile Leu Asn Arg Lys Ser Met Gly Glu Asp Leu Phe
                180                 185                 190

Trp Ala Ile Arg Gly Gly Gly Ala Gly Ser Phe Gly Ile Val Ile Ala
                195                 200                 205

Trp Lys Val Arg Leu Ile Asp Val Pro Ser Thr Val Thr Val Phe Glu
    210                 215                 220

Thr Val Arg Met Trp Glu Asp Asn Val Thr Lys Lys Phe Val His Arg
225                 230                 235                 240

Tyr Gln Arg Arg Ala Ser Asn Ile Asp Lys Asp Leu Thr Ile Phe Leu
                245                 250                 255

Gly Phe Arg Thr Thr Asn Thr Ser Asp Glu Gln Gly Asn Ser Lys Ile
                260                 265                 270

Gln Ile Ile Thr Ile Ile Ser Ala Thr Phe His Gly Ser Arg Asp Arg
                275                 280                 285

Leu Leu Pro Leu Met Gln Glu Glu Phe Pro Glu Leu Gly Leu Gly Lys
    290                 295                 300

Glu Asp Phe Lys Glu Met Ser Trp Val Gln Ser Ile Val His Tyr Asn
305                 310                 315                 320

Asn Tyr Lys Asp Asp Asp Pro Leu Glu Val Leu Leu Asn Lys Thr Val
                325                 330                 335

Asn Phe Glu Pro Asn Pro Phe Lys Leu Lys Ser Asp Tyr Val Lys Lys
                340                 345                 350

Pro Ile Pro Asp Asp Val Leu Glu Lys Leu Leu Ala Arg Leu Tyr Glu
                355                 360                 365

Glu Asp Ile Gly Tyr Asp Phe Val Glu Phe Phe Pro Tyr Gly Gly Lys
370                 375                 380

Leu Ser Glu Ile Ser Glu Ser Glu Ile Pro Phe Pro His Arg Ala Gly
385                 390                 395                 400

Asn Leu Tyr Asn Leu Arg Tyr Met Ala Ser Trp Lys Gln Gly Glu Asn
                405                 410                 415

Thr Thr Arg Ile Asn Asn His Leu Ser Trp Val Arg Ser Val Tyr Asp
                420                 425                 430

Ser Met Thr Pro Tyr Val Ser Lys Asn Pro Arg Gly Ala Tyr Leu Asn
                435                 440                 445

Phe Arg Asp Leu Asp Ile Gly Val Asn Pro Asn Glu Ser Asp Pro Thr
450                 455                 460

Ser Ala Tyr Asn Tyr Val Lys Gln Ala Ser Val Trp Gly Thr Lys Tyr
```

```
                465                 470                 475                 480
Phe Lys Asn Asn Phe Tyr Lys Met Val Phe Ile Lys Thr Leu Val Asp
                    485                 490                 495

Pro Thr Asn Phe Phe Thr Tyr Glu Gln Ser Ile Pro Pro Ile Leu His
                500                 505                 510

His

<210> SEQ ID NO 13
<211> LENGTH: 42
<212> TYPE: DNA
<213> ORGANISM: Artificial Sequence
<220> FEATURE:
<223> OTHER INFORMATION: Synthesized

<400> SEQUENCE: 13
aacctgtatt ttcagggatc cgatcaaatt ggtcatgaag gc                           42

<210> SEQ ID NO 14
<211> LENGTH: 47
<212> TYPE: DNA
<213> ORGANISM: Artificial Sequence
<220> FEATURE:
<223> OTHER INFORMATION: Synthesized

<400> SEQUENCE: 14
ctcgagactg caggctctag attacctttt gtaatgtggt gaaagag                     47

<210> SEQ ID NO 15
<211> LENGTH: 121
<212> TYPE: DNA
<213> ORGANISM: Artificial Sequence
<220> FEATURE:
<223> OTHER INFORMATION: Synthesized

<400> SEQUENCE: 15
gattacgata tcccaacgac cgaaaacctg tattttcagg gatccggaat tcaaaggcct       60
acgtcgacga gctcactagt cgcggccgct ttcgaatcta gagcctgcag tctcgaggca      120
t                                                                      121

<210> SEQ ID NO 16
<211> LENGTH: 669
<212> TYPE: PRT
<213> ORGANISM: Artificial Sequence
<220> FEATURE:
<223> OTHER INFORMATION: Synthesized

<400> SEQUENCE: 16

Met Val Ser Ala Ile Val Leu Tyr Val Leu Leu Ala Ala Ala Ala His
1               5                   10                  15

Ser Ala Phe Ala Ala Gly Met Gly His His His His His His Gly Ser
                20                  25                  30

Leu Gln Asp Ser Glu Val Asn Gln Glu Ala Lys Pro Glu Val Lys Pro
            35                  40                  45

Glu Val Lys Pro Glu Thr His Ile Asn Leu Lys Val Ser Asp Gly Ser
        50                  55                  60

Ser Glu Ile Phe Phe Lys Ile Lys Lys Thr Thr Pro Leu Arg Arg Leu
65                  70                  75                  80

Met Glu Ala Phe Ala Lys Arg Gln Gly Lys Glu Met Asp Ser Leu Thr
                85                  90                  95

Phe Leu Tyr Asp Gly Ile Glu Ile Gln Ala Asp Gln Thr Pro Glu Asp
```

```
            100                 105                 110
Leu Asp Met Glu Asp Asn Asp Ile Ile Glu Ala His Arg Glu Gln Ile
    115                 120                 125

Gly Gly Asp Tyr Asp Ile Pro Thr Thr Glu Asn Leu Tyr Phe Gln Gly
130                 135                 140

Ser Asp Gln Ile Gly His Glu Gly Phe Leu Lys Cys Leu Ile Thr Arg
145                 150                 155                 160

Ile Ser Lys Ser Asn Ser Thr Ser Thr Ser Glu Ser Ile Ile Tyr Thr
                165                 170                 175

Gln Asn Asn Pro Ser Tyr Ser Thr Ile Leu Thr Ser Thr Met Gln Asn
                180                 185                 190

Pro Arg Phe Leu Ser Leu Pro Ile Pro Lys Pro Phe Val Ile Val Thr
                195                 200                 205

Pro Leu His Val Ser His Val Gln Ala Thr Leu Tyr Cys Ala Lys Lys
        210                 215                 220

His Asp Ile Gln Ile Arg Ile Arg Ser Gly Gly His Asp Tyr Glu Gly
225                 230                 235                 240

Leu Ser Tyr Met Ser Asn Val Thr Phe Val Ile Leu Asp Leu Arg Asn
                245                 250                 255

Leu Ser Ser Ile Asn Ile Asp Val Lys Arg Lys Ser Ala Trp Val Gln
                260                 265                 270

Ser Gly Ala Thr Ile Gly Glu Leu Tyr Tyr Arg Ile Ala Glu Lys Ser
            275                 280                 285

Leu Ser Leu Ala Phe Pro Gly Gly Leu Gly His Thr Ile Gly Val Gly
    290                 295                 300

Gly Gln Leu Gly Gly Gly Gly Tyr Gly Tyr Ser Thr Arg Lys Tyr Gly
305                 310                 315                 320

Leu Ala Ser Asp Asn Ile Ile Asp Ala Gln Phe Met Asp Val Gln Gly
                325                 330                 335

Arg Ile Leu Asn Arg Lys Ser Met Gly Glu Asp Leu Phe Trp Ala Ile
                340                 345                 350

Arg Gly Gly Gly Ala Gly Ser Phe Gly Ile Val Leu Ala Trp Lys Ile
            355                 360                 365

Arg Leu Val Asp Val Pro Thr Thr Val Thr Val Phe Glu Ala Val Arg
    370                 375                 380

Lys Trp Glu Asn Asn Ala Thr Lys Lys Phe Val His Arg Tyr Gln Arg
385                 390                 395                 400

Arg Ile Ala Asp Ile Asp Lys Asp Leu Thr Ile Phe Leu Gly Phe Gln
                405                 410                 415

Thr Ala Asn Thr Gly Asp Glu Gln Gly Asn Thr Lys Ile Glu Val Leu
                420                 425                 430

Ala Val Ile Ser Ala Thr Phe His Gly Ser Gln Asp Lys Val Leu Pro
            435                 440                 445

Leu Met Gln Lys Glu Phe Pro Glu Leu Gly Leu Leu Lys Glu Glu Cys
    450                 455                 460

Ile Glu Met Pro Trp Val Arg Ser Ile Met His Tyr Asn Phe Phe Arg
465                 470                 475                 480

Asn Gly Glu Pro Leu Glu Val Leu Leu Asn Arg Thr Leu Asn Phe Glu
                485                 490                 495

Met Lys Ala Phe Lys Leu Lys Ser Asp Tyr Val Lys Glu Pro Ile Pro
                500                 505                 510

Asp Asp Val Leu Glu Lys Leu Leu Gly Lys Leu Tyr Glu Glu Glu Ile
            515                 520                 525
```

```
Gly Glu Gly Tyr Ile Glu Leu Phe Pro Tyr Gly Gly Lys Met Asn Glu
            530                 535                 540

Ile Ser Glu Ser Glu Ile Pro Phe Pro His Arg Ala Gly Asn Leu Tyr
545                 550                 555                 560

Asn Leu Arg Tyr Leu Val Ser Trp Ile Asp Asp Gly Asn Ile Thr Arg
                565                 570                 575

Thr Asn Glu His Ile Arg Trp Val Arg Ser Ala Tyr Asp Tyr Met Thr
            580                 585                 590

Pro Phe Val Ser Lys Asn Pro Arg Gly Ala Tyr Leu Asn Phe Arg Asp
        595                 600                 605

Leu Asp Ile Gly Ile Asn Ser Asp Glu Asp Tyr Asn Tyr Val Ala
610                 615                 620

Gln Ala Ser Ile Trp Gly Thr Lys Tyr Phe Lys Ser Asn Phe Tyr Arg
625                 630                 635                 640

Leu Val Tyr Val Lys Thr Leu Val Asp Pro Thr Asn Phe Phe Thr Tyr
                645                 650                 655

Glu Gln Ser Ile Pro Pro Leu Ser Pro His Tyr Lys Arg
            660                 665
```

```
<210> SEQ ID NO 17
<211> LENGTH: 658
<212> TYPE: PRT
<213> ORGANISM: Artificial Sequence
<220> FEATURE:
<223> OTHER INFORMATION: Synthesized

<400> SEQUENCE: 17

Met Val Ser Ala Ile Val Leu Tyr Val Leu Leu Ala Ala Ala Ala His
1               5                   10                  15

Ser Ala Phe Ala Ala Gly Met Gly His His His His His His Gly Ser
            20                  25                  30

Leu Gln Asp Ser Glu Val Asn Gln Glu Ala Lys Pro Glu Val Lys Pro
        35                  40                  45

Glu Val Lys Pro Glu Thr His Ile Asn Leu Lys Val Ser Asp Gly Ser
50                  55                  60

Ser Glu Ile Phe Phe Lys Ile Lys Lys Thr Thr Pro Leu Arg Arg Leu
65                  70                  75                  80

Met Glu Ala Phe Ala Lys Arg Gln Gly Lys Glu Met Asp Ser Leu Thr
                85                  90                  95

Phe Leu Tyr Asp Gly Ile Glu Ile Gln Ala Asp Gln Thr Pro Glu Asp
            100                 105                 110

Leu Asp Met Glu Asp Asn Asp Ile Ile Glu Ala His Arg Glu Gln Ile
        115                 120                 125

Gly Gly Asp Tyr Asp Ile Pro Thr Thr Glu Asn Leu Tyr Phe Gln Gly
130                 135                 140

Ser His Glu Glu Phe Leu Gln Cys Leu Ser Ser Arg Ile Pro Lys Ser
145                 150                 155                 160

Ile Ile Tyr Ala Ser Asn Asn Pro Ser Tyr Ser Asn Val Leu Asp Ser
                165                 170                 175

Thr Thr Gln Asn Pro Arg Phe Leu Ser Ser Thr Arg Asn Pro Ser
            180                 185                 190

Val Ile Val Thr Pro Phe Lys Ile Ser His Ile Gln Pro Thr Ile Tyr
        195                 200                 205

Cys Ser Lys Lys His Gly Val Gln Ile Arg Ile Arg Ser Gly Gly His
210                 215                 220
```

```
Asp Tyr Glu Gly Leu Ser Tyr Gln Ser Ser Val Pro Phe Phe Ile Leu
225                 230                 235                 240

Asp Leu Arg Asn Ile Asn Ser Ile Gln Val Asp Val Glu Lys Lys Ser
            245                 250                 255

Ala Trp Val Glu Ala Gly Ala Thr Leu Gly Glu Leu Tyr Tyr Ser Ile
        260                 265                 270

Ala Lys Lys Ser Lys Thr Leu Gly Phe Pro Gly Gly Leu Cys Ser Thr
    275                 280                 285

Val Gly Val Gly Gly Gln Leu Gly Gly Gly Tyr Gly Tyr Gln Ser
290                 295                 300

Arg Thr Tyr Gly Leu Ala Ser Asp Asn Ile Ile Asp Ala Gln Leu Ile
305                 310                 315                 320

Asp Ala Arg Gly Arg Ile Leu Asn Arg Lys Ser Met Gly Glu Asp Leu
            325                 330                 335

Phe Trp Ala Ile Arg Gly Gly Ala Gly Ser Phe Gly Ile Val Ile
        340                 345                 350

Ala Trp Lys Val Arg Leu Ile Asp Val Pro Ser Thr Val Thr Val Phe
    355                 360                 365

Glu Thr Val Arg Met Trp Glu Asp Asn Val Thr Lys Lys Phe Val His
370                 375                 380

Arg Tyr Gln Arg Arg Ala Ser Asn Ile Asp Lys Asp Leu Thr Ile Phe
385                 390                 395                 400

Leu Gly Phe Arg Thr Thr Asn Thr Ser Asp Glu Gln Gly Asn Ser Lys
            405                 410                 415

Ile Gln Ile Ile Thr Ile Ile Ser Ala Thr Phe His Gly Ser Arg Asp
        420                 425                 430

Arg Leu Leu Pro Leu Met Gln Glu Glu Phe Pro Glu Leu Gly Leu Gly
    435                 440                 445

Lys Glu Asp Phe Lys Glu Met Ser Trp Val Gln Ser Ile Val His Tyr
450                 455                 460

Asn Asn Tyr Lys Asp Asp Pro Leu Glu Val Leu Leu Asn Lys Thr
465                 470                 475                 480

Val Asn Phe Glu Pro Asn Pro Phe Lys Leu Lys Ser Asp Tyr Val Lys
            485                 490                 495

Lys Pro Ile Pro Asp Asp Val Leu Glu Lys Leu Leu Ala Arg Leu Tyr
        500                 505                 510

Glu Glu Asp Ile Gly Tyr Asp Phe Val Glu Phe Pro Tyr Gly Gly
    515                 520                 525

Lys Leu Ser Glu Ile Ser Glu Ser Glu Ile Pro Phe Pro His Arg Ala
530                 535                 540

Gly Asn Leu Tyr Asn Leu Arg Tyr Met Ala Ser Trp Lys Gln Gly Glu
545                 550                 555                 560

Asn Thr Thr Arg Ile Asn Asn His Leu Ser Trp Val Arg Ser Val Tyr
            565                 570                 575

Asp Ser Met Thr Pro Tyr Val Ser Lys Asn Pro Arg Gly Ala Tyr Leu
        580                 585                 590

Asn Phe Arg Asp Leu Asp Ile Gly Val Asn Pro Asn Glu Ser Asp Pro
    595                 600                 605

Thr Ser Ala Tyr Asn Tyr Val Lys Gln Ala Ser Val Trp Gly Thr Lys
610                 615                 620

Tyr Phe Lys Asn Asn Phe Tyr Lys Met Val Phe Ile Lys Thr Leu Val
625                 630                 635                 640
```

Asp Pro Thr Asn Phe Phe Thr Tyr Glu Gln Ser Ile Pro Pro Ile Leu
                645                 650                 655

His His

<210> SEQ ID NO 18
<211> LENGTH: 43
<212> TYPE: DNA
<213> ORGANISM: Artificial Sequence
<220> FEATURE:
<223> OTHER INFORMATION: Synthesized

<400> SEQUENCE: 18
aacctgtatt ttcagggatc ccatgaagag tttcttcagt gcc          43

<210> SEQ ID NO 19
<211> LENGTH: 42
<212> TYPE: DNA
<213> ORGANISM: Artificial Sequence
<220> FEATURE:
<223> OTHER INFORMATION: Synthesized

<400> SEQUENCE: 19
ctcgagactg caggctctag attaatggtg aagaataggt gg           42

<210> SEQ ID NO 20
<211> LENGTH: 81
<212> TYPE: DNA
<213> ORGANISM: Artificial Sequence
<220> FEATURE:
<223> OTHER INFORMATION: Synthesized

<400> SEQUENCE: 20
atgcagtact ttccttccc ttcatcgtta gccaaaatca ccatctttct gatcttttca    60
tttgtattcg caagttcagc t                                            81

<210> SEQ ID NO 21
<211> LENGTH: 27
<212> TYPE: PRT
<213> ORGANISM: Artificial Sequence
<220> FEATURE:
<223> OTHER INFORMATION: Synthesized

<400> SEQUENCE: 21

Met Gln Tyr Phe Ser Phe Pro Ser Ser Leu Ala Lys Ile Thr Ile Phe
1               5                   10                  15

Leu Ile Phe Ser Phe Val Phe Ala Ser Ser Ala
            20                  25

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

Met Val Ser Ala Ile Val Leu Tyr Val Leu Leu Ala Ala Ala Ala His
1               5                   10                  15

Ser Ala Phe Ala
            20

<210> SEQ ID NO 23
<211> LENGTH: 6
<212> TYPE: PRT

<213> ORGANISM: Artificial Sequence
<220> FEATURE:
<223> OTHER INFORMATION: Synthesized

<400> SEQUENCE: 23

His His His His His His
1               5

<210> SEQ ID NO 24
<211> LENGTH: 96
<212> TYPE: PRT
<213> ORGANISM: Artificial Sequence
<220> FEATURE:
<223> OTHER INFORMATION: Synthesized

<400> SEQUENCE: 24

Asp Ser Glu Val Asn Gln Glu Ala Lys Pro Glu Val Lys Pro Glu Val
1               5                   10                  15

Lys Pro Glu Thr His Ile Asn Leu Lys Val Ser Asp Gly Ser Ser Glu
            20                  25                  30

Ile Phe Phe Lys Ile Lys Lys Thr Thr Pro Leu Arg Arg Leu Met Glu
        35                  40                  45

Ala Phe Ala Lys Arg Gln Gly Lys Glu Met Asp Ser Leu Thr Phe Leu
    50                  55                  60

Tyr Asp Gly Ile Glu Ile Gln Ala Asp Gln Thr Pro Glu Asp Leu Asp
65                  70                  75                  80

Met Glu Asp Asn Asp Ile Ile Glu Ala His Arg Glu Gln Ile Gly Gly
                85                  90                  95

<210> SEQ ID NO 25
<211> LENGTH: 7
<212> TYPE: PRT
<213> ORGANISM: Artificial Sequence
<220> FEATURE:
<223> OTHER INFORMATION: Synthesized

<400> SEQUENCE: 25

Glu Asn Leu Tyr Phe Gln Gly
1               5

<210> SEQ ID NO 26
<211> LENGTH: 31
<212> TYPE: DNA
<213> ORGANISM: Artificial Sequence
<220> FEATURE:
<223> OTHER INFORMATION: Synthesized

<400> SEQUENCE: 26
agagacgatc tgccgtctca ctagagcggc c                              31

<210> SEQ ID NO 27
<211> LENGTH: 523
<212> TYPE: PRT
<213> ORGANISM: Artificial Sequence
<220> FEATURE:
<223> OTHER INFORMATION: Synthesized

<400> SEQUENCE: 27

Asn Asp Thr His Glu Ala Phe Leu Glu Cys Leu Thr Thr Arg Ile Pro
1               5                   10                  15

Ser Asn Ser Thr Phe Thr Pro Gln Ser Ile Ile Tyr Thr Pro Asp Asn
            20                  25                  30

Pro Ser Tyr Ser Thr Ile Leu Asp Ser Thr Thr Gln Asn Pro Arg Phe

```
            35                  40                  45
Leu Ser Ser Thr Arg Asn Pro Phe Ala Ile Ile Thr Pro Leu His
 50                  55                  60

Ala Ser His Ile Gln Ala Ala Leu Tyr Cys Ser Gln Lys His Gly Glu
 65                  70                  75                  80

Gln Met Arg Ile Arg Ser Gly Gly His Asp Tyr Glu Gly Leu Ser Tyr
                     85                  90                  95

Gln Ser Ser Val Pro Phe Phe Ile Leu Asp Leu Arg Asn Leu Ser Ser
                100                 105                 110

Ile Ser Ile Asp Ala Lys Ser Lys Ser Ala Trp Val Gln Ala Gly Ala
                115                 120                 125

Thr Ile Gly Glu Leu Tyr Tyr Gly Ile Ala Lys Thr Ser Leu Asn Leu
                130                 135                 140

Ser Phe Pro Gly Gly Val Ala His Thr Ile Gly Val Gly Gly Gln Leu
145                 150                 155                 160

Gly Gly Gly Gly Tyr Gly Tyr Ser Thr Arg Lys Tyr Gly Leu Ala Ser
                    165                 170                 175

Asp Asn Val Ile Asp Ala Gln Leu Ile Asp Ala Arg Gly Arg Ile Leu
                180                 185                 190

Asp Arg Lys Thr Met Gly Glu Asp Leu Phe Trp Ala Ile Arg Gly Gly
                195                 200                 205

Gly Ala Gly Ser Phe Gly Ile Val Leu Ala Trp Lys Ile Arg Leu Val
210                 215                 220

Asn Thr Pro Ser Thr Val Thr Ile Phe Glu Ala Val Arg Ser Trp Glu
225                 230                 235                 240

Asn Asn Thr Thr Lys Lys Phe Ile Arg Arg Tyr Gln Arg Arg Ala Ser
                    245                 250                 255

Lys Thr Asp Lys Asp Leu Thr Ile Phe Val Gly Phe Arg Thr Thr Ser
                260                 265                 270

Ser Thr Asp Glu Glu Gly Asn Glu Arg Ile Ser Ile Leu Thr Ile Val
                275                 280                 285

Ser Ala Thr Phe His Gly Ser Lys Asp Arg Leu Leu Gln Leu Val Gln
290                 295                 300

Lys Glu Phe Pro Asp Leu Gly Leu Val Ser Glu Cys Thr Glu Met
305                 310                 315                 320

Ser Trp Val Arg Ser Ile Ile His Phe Asn Leu Phe Gly Asp Glu Val
                    325                 330                 335

Pro Leu Glu Val Leu Leu Asn Arg Thr Leu Asn Phe Glu Met Lys Ala
                340                 345                 350

Phe Lys Leu Arg Ser Asp Tyr Val Gln Lys Pro Ile Pro Asp Asp Val
                355                 360                 365

Leu Glu Lys Leu Leu Ser Lys Leu Tyr Asp Glu Thr Gly Glu Gly
                370                 375                 380

Tyr Ile Glu Phe Phe Pro Tyr Gly Gly Lys Met Ser Lys Ile Ser Glu
385                 390                 395                 400

Ser Glu Ile Pro Phe Pro Tyr Arg Ala Gly Asn Leu Tyr Asn Leu Arg
                405                 410                 415

Tyr Met Val Ser Trp Lys Asp Asp Gly Asn Ile Thr Arg Thr Asn Met
                420                 425                 430

His Leu Ser Trp Ile Lys Asp Ala Tyr Asp Tyr Met Thr Pro Tyr Val
                435                 440                 445

Ser Lys Asp Pro Arg Gly Ala Tyr Leu Asn Phe Arg Asp Leu Asp Ile
                450                 455                 460
```

-continued

```
Gly Val Asn Val Asn Glu Ser Asp Tyr Asp Tyr Val Ala Lys Ala Ser
465                 470                 475                 480

Val Trp Gly Thr Lys Tyr Phe Arg Asn Asn Phe Tyr Arg Leu Val Asp
                485                 490                 495

Ile Lys Thr Ile Val Asp Pro Thr Asn Phe Phe Lys Tyr Glu Gln Ser
            500                 505                 510

Ile Pro Pro Leu Pro Pro Leu His Ser Ala Met
        515             520
```

DIELS-ALDERASE AND USE THEREOF

RELATED APPLICATIONS

This application claims priority to Chinese Patent Application No. 2019111362437 which was filed on Nov. 19, 2019, which is hereby incorporated by reference in its entirety.

TECHNICAL FIELD

The present invention belongs to the field of gene engineering technology. More particularly, the present invention relates to a Diels-Alderase identified from *Morus alba* and use thereof in promoting Diels-Alder reaction.

BACKGROUND ART

Diels-Alder (D-A) reaction, a [4+2] cycloaddition reaction between a conjugated diene and a dienophile, is one of the most powerful carbon-carbon bond forming reactions in organic chemistry. It can construct new six-membered rings and multiple chiral centers in one step, rapidly increase the complexity of molecules and plays an important role in synthetic chemistry. There are numerous six-membered ring-containing natural products with complex structure and excellent bioactivities, such as anti-cancer drugs taxol and dynemycin A. Total syntheses of these natural products often rely on D-A reaction as the key step to construct six-membered ring skeleton and form new chiral center. However, due to the lack of good catalyst to control the regio-, endo/exo and stereoselectivity of D-A reaction, there will be many by-products in the reaction, which will reduce the yield and stereoselectivity of the target products, as shown in FIG. 1. Thus, the synthetic value of D-A reaction in total synthesis and drug synthesis is limited. Therefore, the development and utilization of enzymes that can catalyze the D-A reaction and enable it to selectively produce D-A products with defined stereo-structure (as shown in the circular box in FIG. 1) not only contributes to scientific innovation, but also has strong industrial application value. Unfortunately, no enzyme that can selectively catalyze the intermolecular D-A reaction has been found in nature.

"Sang-bai-pi" (the mulberry root bark or stem bark) is a traditional Chinese medicine used for anti-inflammatory, diuretic, antiasthmatic and other purposes. Moreover, it is a major bioactive component of the effective anti-HIV medicine ("oral suspension SH"). "Sang-bai-pi" is rich in D-A type flavonoids natural products. These natural products have unique structures and show good antibacterial, antiviral and anti-diabetic activities. Biosynthetically, they are proposed to be synthesized by an oxidase and an enzyme catalyzing Diels-Alder reactions (Diel-Alderase) in mulberry, as shown in FIG. 2. Due to their complex structures with multiple chiral centers, the asymmetric total syntheses of these natural products are faced with great challenges. Although there are few reports on asymmetric D-A reaction promoted by chiral boric acid complexes to realize asymmetric total synthesis of these natural products, the synthetic routes are still faced with the problems of long synthetic route, poor selectivity and low yield. Compared with the chemical catalyst, enzymes normally have higher efficiency and stereoselectivity. Therefore, discovery of the intermolecular Diels-Alderase in mulberry can not only contribute to a green and efficient synthesis of endo type D-A natural product in mulberry and their analogues, laying the foundation for developing and utilizing this type of natural products for medicinal purposes, but also offers new possibilities for efficient synthesis of important chemical precursors or natural products containing six-membered rings.

SUMMARY OF THE INVENTION

The purpose of the present invention is to provide a Diels-Alderase and use thereof in promoting D-A reaction.

Firstly, the present invention provides a Diels-Alderase identified from *Morus alba*, which is named as MaDA and has: 1) an amino acid sequence represented by SEQ ID No.1; or 2) an amino acid sequence that is derived from the amino acid sequence represented by SEQ ID No. 1 by substitution, deletion and/or addition of one or more amino acids and is 80%, 85%, 90%, 95%, 98%, 99% homologous to SEQ ID No. 1, wherein the protein formed by the amino acid sequence shares similar activity to the protein derived from 1).

Moreover, the present invention also provides homologous proteins of MaDA, i.e. MaDA-1 and MaDA-2, which have the amino acid sequences represented by SEQ ID Nos.10 and 12, respectively. Their nucleotide sequences are represented by SEQ ID Nos.9 and 11, respectively.

The present invention also provides a gene coding the Diels-Alderase, and the gene has:

1) a nucleotide sequence represented by SEQ ID No.2; or
2) a nucleotide sequence derived from SEQ ID No.2 by substitution, deletion and/or addition of one or more nucleotides; or
3) a nucleotide sequence that hybridizes with the sequence defined in 1) under a stringent condition.

The MaDA gene is amplified from cDNA of mulberry (*Morus alba*), and its nucleotide sequence is represented by SEQ ID No.2, which is a complete open reading frame (ORF). This open reading frame starts from ATG and ends with TGA, with a total of 1653 nucleotides. Among them, the first 81 nucleotides SEQ ID No.: 20
ATGCAGTACTTTTCCTTCCCTTCATCGTTAGCCAAAATCACCATCTTTC

TGATCTTTTCATTTGTATTCGCAAGTTCAGCT, is the nucleotide sequence of a signal peptide.

As shown in SEQ ID No.1, the Diels-Alderase MaDA contains 550 amino acids. The first 27 amino acids (MV-SAIVLYVLLAAAAHSAFA, SEQ ID No.: 21) is the signal peptide encoded by the gene, which will be removed during the secretion of the mature enzyme protein into the extracellular space. Therefore, the mature MaDA starts from Asn28, with a total of 523 amino acids, a theoretical molecular weight (MWt) of 59075.78 and a theoretical isoelectric point (PI) of 6.62.

Secondly, the present invention also provides a biomaterial containing a gene encoding the MaDA enzyme, and the bio-material is an expression kit, a plasmid, a vector, a microorganism, an insect cell, an animal cell or a plant cell.

Preferably, the bio-materials is expression vector pI-sec-sumostar-tev2, the nucleotide sequences of which is represented by SEQ ID No.3.

The present invention provides the use of the expression vector pI-sec-sumostar-tev2 in expressing mature MaDA enzyme protein without a signal peptide in insect cells.

In the Examples of the present invention, the expression vector pI-sec-sumostar-tev2 containing a MaDA gene sequence was constructed, and large-scale expression of MaDA in insect cells (Hi5) was achieved. The SUMO- MaDA protein expressed in insects by this vector contains a signal peptide, a 6×His tag and a SUMO tag at N-terminal. The amino acid sequence of SUMO-MaDA protein is represented by SEQ ID No.4.

Wherein, the first 20 amino acids (MVSAIVLYVLLAAAHSAFA, SEQ ID No.: 22) is the signal peptide, HHHHHH, SEQ ID No.: 23, is the 6× his tag,

```
                                          SEQ ID No.: 24
DSEVNQEAKPEVKPEVKPETHINLKVSDGSSEIFFKIKKTTPLRRLMEAFA

KRQGKEMDSLTFLYDGIEIQADQTPEDLDMEDNDIIEAHREQIGG,
``` is the SUMO tag, and ENLYFQG, SEQ ID No.: 25, is the TEV restriction site. The mature protein expressed by the insect expression system and purified has no signal peptide. Its theoretical molecular weight (MWt) is 73288.49, and the theoretical isoelectric point (PI) of the enzyme protein is 5.76. After hydrolysis with TEV enzyme, the mature protein of MaDA could be obtained without a signal peptide.

Thirdly, the present invention provides the use of the Diels-Alderase or coding gene thereof, or a biomaterial containing the coding gene in catalyzing Diels-Alder reaction.

The present invention provides the use of the Diels-Alderase or coding gene thereof or a biomaterial containing the coding gene in the preparation of natural products containing 6-membered ring skeleton or stereospecific synthesis of natural products with endo-configuration, preferably in the preparation of natural flavonoid products or analogues thereof.

Specifically, the above use is to utilize Diels-Alderases MaDA, MaDA-1, MaDA-2 or encoding genes thereof or a bio-material containing the coding gene of the Diels-Alderase as a catalytic enzyme to stereospecifically synthesize natural products with endo-configuration in mulberry tree and their derivatives from dienophiles and dienes as substrates.

Furthermore, as for the dienophile chalcones, different substituents at different positions of the benzene ring are tolerated. As for the dienes, they can be the compounds containing dehydroprenyl moiety found in moraceous plants, which include dehydroprenyl flavonoids, dehydroprenyl stilbenes, dehydroprenyl chalcones and dehydroprenyl benzofurans. All the compounds mentioned above can be used as substrates for the Diels-Alderase.

The present invention provides a method for catalyzing Diels-Alder reaction, wherein the method comprises using bio-material containing Diels-Alderase or homologous proteins of the Diels-Alderase;

wherein the Diels-Alderase has 1) an amino acid sequence represented by SEQ ID No. 1; or 2) an amino acid sequence that is derived from the amino acid sequence represented by SEQ ID No. 1 by substitution, deletion and/or addition of one or more amino acids and is 80%, 85%, 90%, 95%, 98%, 99% homologous to SEQ ID No. 1, wherein the protein formed by the amino acid sequence shares similar activity to the protein derived from 1).

Preferably, the Diels-Alder reaction is performed for generating natural products containing 6-membered ring skeleton or natural products with endo-configuration, preferably, the Diels-Alder reaction is performed for generating natural flavonoid products or analogues thereof.

Preferably, the bio-material is an expressing kit, a plasmid, a vector, a microorganism, an insect cell, an animal cell or a plant cell.

Preferably, in the Diels-Alder reaction, dienophiles and dienes are used as substrates.

Preferably, the dienophiles are chalcone or its derivatives, and the dienes are dehydroprenyl flavonoids, dehydroprenyl stilbenes, dehydroprenyl chalcones, or dehydroprenyl benzofurans.

Preferably, in the Diels-Alder reaction, reaction temperature is 50° C., and pH is 8.0.

The beneficial effect of the invention further reveals that the optimum reaction temperature and pH of MaDA from mulberry are 50° C. and 8.0, respectively, and the catalytic efficiency of MaDA to form chalcomoracin is very high at this optimum condition.

The beneficial effect of the present invention lies in that MaDA identified from mulberry tree can stereospecifically synthesize natural products with endo configuration with chalcone or its derivatives and compounds containing dehydroprenyl moiety as substrates, and can be used to synthesize D-A type natural products and their derivatives in vitro. The MaDA has good substrate adaptability. Different substituted chalcones and its derivatives can be used as dienophiles to generate natural products such as mulberofurans E/O, chalcomarcin and its derivatives at a conversion of 70% or more. The MaDA provided in the present invention has certain activity on different dienes (dehydroprenylbenzene diene) containing dehydroprenyl structural unit found in moraceae plants, can specifically generate endo products, and exhibits a good substrate adaptability and selectivity. Different types of D-A natural products from Moraceae plants can be obtained in high yield (up to 62%) by two-step cascade reactions composed of a hydrolysis in situ to form unstable dienes under basic conditions and an asymmetric D-A reaction catalyzed by MaDA. The successful application of MaDA has laid the foundation for developing and utilizing this type of natural products for medicinal purposes, meanwhile, offers new possibilities for efficient synthesis of important chemical precursors or natural products containing six-membered rings.

BRIEF DESCRIPTION OF THE DRAWINGS

FIG. 5 shows the activity test results of different purified components. A was the negative control, there was no protein in the system. B was added with crude enzyme of the cell callus; C was added with the active protein fraction purified by hydrophobic column chromatography; D was added with the active protein fraction further purified with ion exchange column chromatography, E was added with the active protein fraction further purified with molecular sieve column chromatography.

FIG. 6 shows the 12% SDS-PAGE of different protein active components. i) shows the total protein in the crude enzyme solution of mulberry suspension cells; ii) shows the active total protein in the crude enzyme solution of mulberry suspension cells purified by hydrophobic column chromatography; iii) shows the active total protein obtained from the previous hydrophobic column chromatography and then purified by ion exchange column chromatography; iv) shows the active protein that was obtained and sequentially purified by hydrophobic column chromatography, ion exchange column chromatography and molecular sieve column chromatography.

FIG. 7 shows the mass spectrometry analysis results of the enriched bands.

FIG. 8 shows the transcription levels of different reticuline oxidase-like enzyme family proteins in *Morus alba*.

FIG. 17 shows the alignment analysis between MaDA-1, represented by SEQ ID No.: 10, and MaDA, represented by SEQ ID No.: 27, protein sequences.

FIG. 19 shows the alignment analysis between MaDA-2, represented by SEQ ID No.: 12, and MaDA, represented by SEQ ID No.: 27, protein sequences.

FIG. 21 shows the activity test results for reaction between different dienes and dienophile 5 under catalyzation of MaDA-2.

SPECIFIC MODES FOR CARRYING OUT THE EMBODIMENTS

The following embodiments give a detailed and specific description of the present invention, but it should be understood that the present invention is not limited to the following examples. Unless otherwise specified, the reagents and raw materials used in the following embodiments are commercially available. The strains, vectors, culture media and reagents used in the following embodiments are mainly as follows:

Competent cells of *E. coli* DH5α and DH10Bac were bought from Beijing Zoman Biotechnology Co., Ltd. Insect cells sf21 and Hi5 were purchased from invitrogen.

Figure 1:
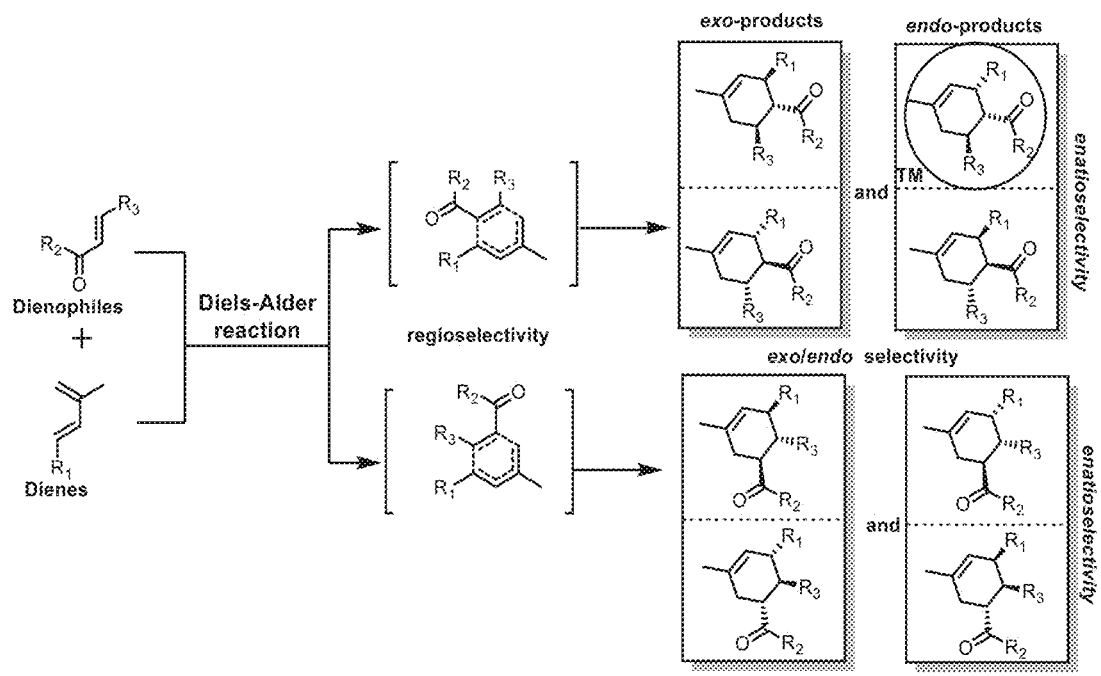
FIG. 1 shows the D-A reaction and its selectivity. When the catalyst cannot control the selectivity of D-A reaction, there will be eight different isomers formed at the same time.
Figure 2:
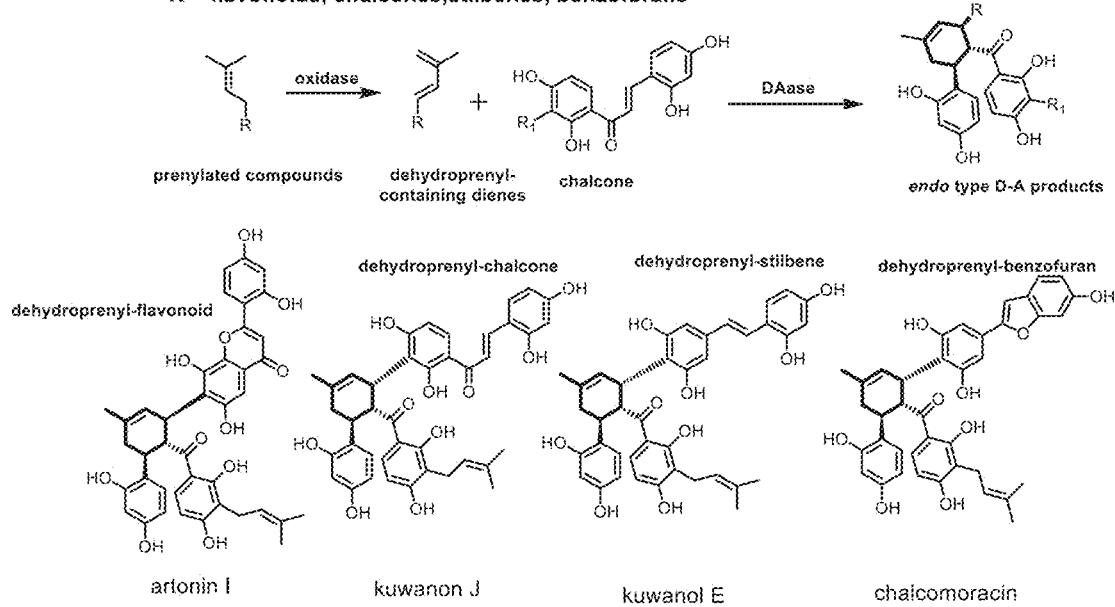
FIG. 2 shows the typical D-A type natural products in Moraceae plants and their biosynthesis pathways. The D-A type natural products from Moraceae plants are composed of same dienophile chalcones and different dienes, including dehydroprenyl flavonoids, dehydroprenyl chalcones, dehydroprenyl stilbenes and dehydroprenyl benzofurans.
Figure 3:
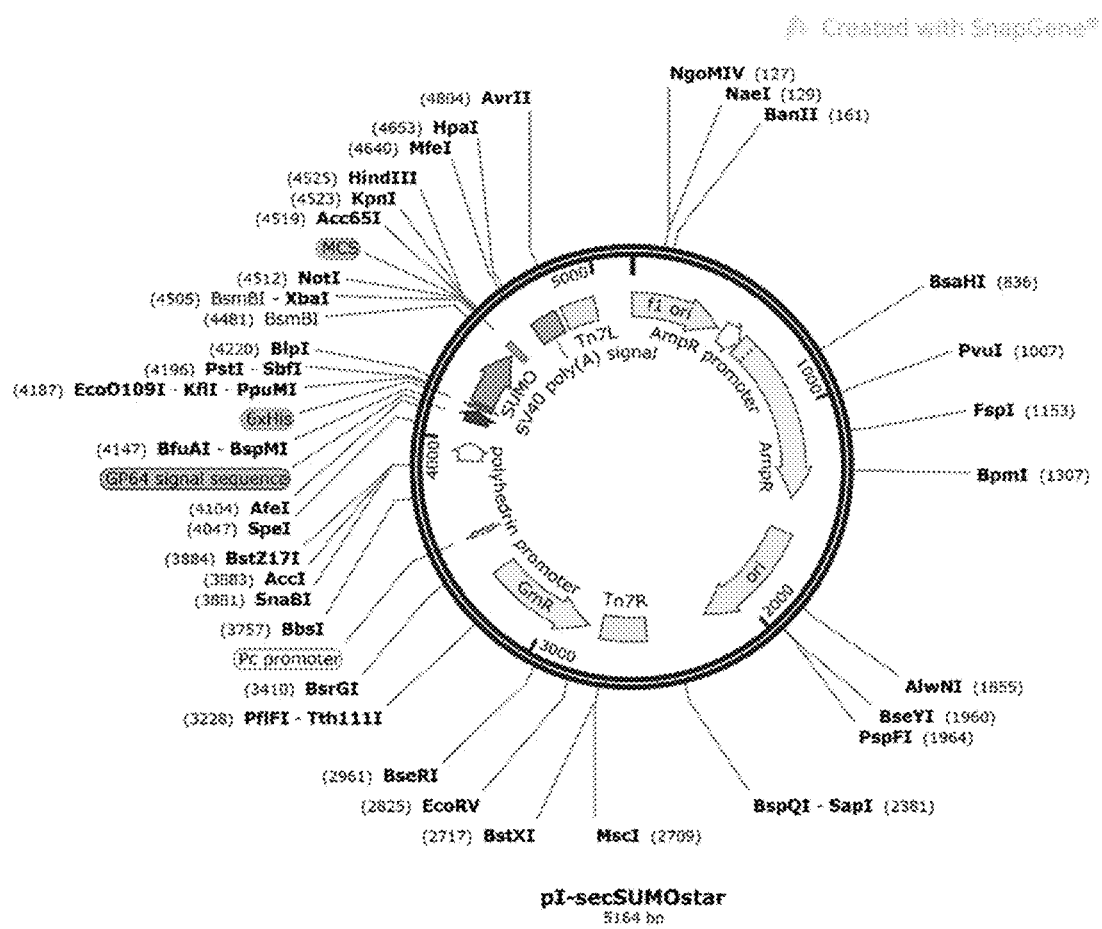
FIG. 3 shows the sequence map of the insect expression vector pI-secSUMOstar.

The insect expression vector pI-secSUMOstar was purchased from LifeSensors company, and its sequence map is shown in FIG. 3. A nucleotide sequence AGAGACGATCTGCCGTCTCACTAGAGCGGCC, SEQ ID NO.: 26) in the above-mentioned pI-secSUMOstar vector was replaced with a nucleotide sequence containing a TEV restriction site (GATTACGATATCCCAACGACCGAAAACCTGTATTTTCAGGGATCCGGAAT

TCAAAGGCCTACGTCGACGAGCTCACTAGTCGCGGCCGCTTTCGAATCTAG

AGCCTGCAGTCTCGAGGCAT, SEQ ID No. 15)

to construct the pI-sec-SUMOstar-tev2 vector. When using the pI-sec-SUMOstar-tev2 vector to express a protein, a new TEV restriction site was added between the SUMO tag and the target protein, which facilitates the subsequent removal of N-terminal SUMO tag. The nucleotide sequence of the pI-sec-SUMOstar-tev2 vector is shown in SEQ ID No.3.

LB solid medium: peptone 10 g/L, yeast powder 5 g/L, NaCl 10 g/L, 1.5% agar.

LB liquid medium: peptone 10 g/L, yeast powder 5 g/L, NaCl 10 g/L.

The total RNA extraction kit, plasmid extraction kit and gel Recovery Kit were purchased from Tiangen Biochemical Co., Ltd. and reverse transcriptional kits were purchased from thermo company. Homologous recombinant enzyme was purchased from Vazyme company. PCR high fidelity enzyme was purchased from TransGen Biotech. PCR primer synthesis and plasmid sequencing were completed by GENEWiZ Biotechnology Co., Ltd. MS medium was purchased from Beijing Solarbio Technology Co., Ltd. SIM SF medium was purchased from Sino Biological Inc. Compound 2 and Dienophile 6 were purchased from BioBioPha.

Dienophile 1 was synthesized according to one literature (Romano. J. J. & Casillas, E. A short synthesis of morachalcone A. Tetrahedron Lett. 2005, 46, 2323-2326). Dienophile 5 was synthesized according to one literature (Han, J., et al Enantioselective biomimetic total syntheses of kuwanons I and J and brosimones A and B, Angew. Chem. Int. Ed. 2014, 53, 9257-9261). Dienophile 11 was synthesized according to one literature (Lee, Y. R., et al. An Efficient and Rapid Synthetic Route to Biologically Interesting Pyranochalcone Natural Products, Molecules 2007, 12, 1420-1429).

Synthesis of Dienophile 7

S1 (29.3 mg, 0.055 mmol) was dissolved in acetone (3 mL) in a sealed tube, then 1,4-cyclohexadiene (52 μL, 0.27 mmol), HCOOH (2 μL, 0.027 mmol), HCOONH$_4$ (3.5 mg, 0.056 mmol) and Pd/C (11.6 mg, 0.011 mmol) were added. The resulting mixture was subjected to a dry ice/acetone bath to remove oxygen, and stirred at 40° C. for 2 h. After cooling to room temperature, the resultant was filtered with celite and spin dried to remove the solvent. After purification by column chromatography (EtOAc/petroleum ether=1/4), Dienophile 7 was obtained (8.7 mg, 45%).

$^1$H NMR (400 MHz, Acetone-d$_6$) δ 14.11 (s, 1H), 8.22 (d, J=15.4 Hz, 1H), 7.89 (d, J=8.8 Hz, 1H), 7.83 (d, J=15.4 Hz, 1H), 7.76 (d, J=8.4 Hz, 1H), 6.62-6.38 (m, 3H), 5.28 (t, J=7.2 Hz, 1H), 3.81 (s, 3H), 3.37 (d, J=7.2 Hz, 2H), 1.78 (s, 3H), 1.64 (s, 3H);

$^{13}$C NMR (101 MHz, Acetone-d$_6$) δ 193.4, 165.1, 164.1, 162.5, 159.7, 140.4, 131.5, 131.4, 130.0, 123.3, 118.4, 116.2, 114.5, 107.9, 107.5, 102.2, 55.7, 25.8, 22.3, 17.9.

Synthesis of Dienophile 8

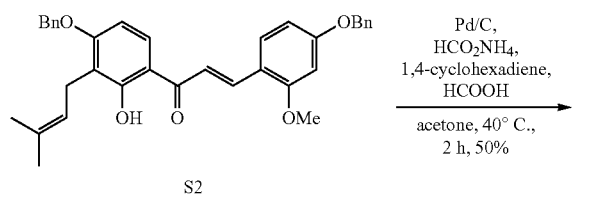

S2

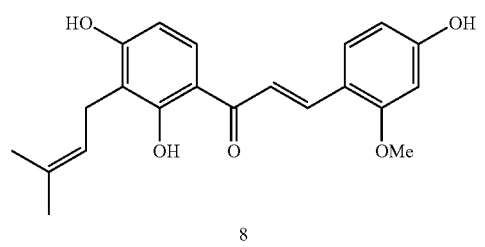

8

S2 (175 mg, 0.32 mmol) was dissolved in acetone (7 mL) in a sealed tube, then 1,4-cyclohexadiene (150 μL, 1.59 mmol), HCOOH (6 μL, 0.16 mmol), HCOONH$_4$ (20 mg, 0.32 mmol) and Pd/C (67 mg, 0.064 mmol) were added. The resulting mixture was subjected to a dry ice/acetone bath to remove oxygen, and stirred at 40° C. for 2 h. After cooling to room temperature, the resultant was filtered with celite and spin dried to remove the solvent. After purification by column chromatography (EtOAc/petroleum ether=1/4), Dienophile 8 was obtained (56.0 mg, 50%).

$^1$H NMR (400 MHz, Acetone-d$_6$) δ 14.11 (s, 1H), 8.18 (d, J=15.6 Hz, 1H), 7.91 (d, J=8.8 Hz, 1H), 7.77 (d, J=15.6 Hz, 1H), 7.73 (d, J=8.4 Hz, 1H), 6.57 (s, 1H), 6.52 (m, 2H), 5.28 (t, J=6.6 Hz, 1H), 3.93 (s, 3H), 3.38 (d, =7.0 Hz, 2H), 1.78 (s, 3H), 1.64 (s, 3H);

$^{13}$C NMR (101 MHz, Acetone-d$_6$) δ 193.4, 165.1, 162.6, 162.5, 161.7, 140.2, 131.6, 131.4, 130.0, 123.3, 118.1, 116.5, 116.1, 114.5, 109.0, 107.9, 99.9, 56.0, 25.9, 22.3, 17.9.

Synthesis of Dienophile 9

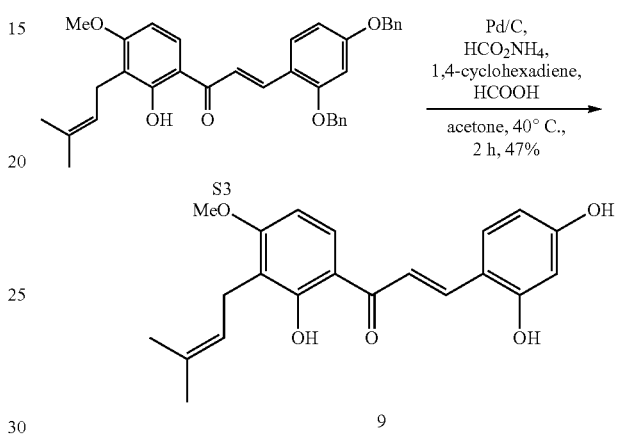

9

S3 (80.2 mg, 0.15 mmol) was dissolved in acetone (4 mL) in a sealed tube, then 1,4-cyclohexadiene (70.9 μL, 0.75 mmol), HCOOH (2.8 μL, 0.075 mmol), HCOONH$_4$ (9.5 mg, 0.15 mmol) and Pd/C (31.8 mg, 0.030 mmol) were added. The resulting mixture was subjected to a dry ice/acetone bath to remove oxygen, and stirred at 40° C. for 2 h. After cooling to room temperature, the resultant was filtered with celite and spin dried to remove the solvent. After purification by column chromatography (dichloromethane/methanol=1/4), Dienophile 9 was obtained (25 mg, 47%).

$^1$H NMR (400 MHz, Acetone-d$_6$) δ 13.92 (s, 1H), 8.24 (d, J=15.4 Hz, 1H), 8.05 (d, J=9.2 Hz, 1H), 7.83 (d, J=15.4 Hz, 1H), 7.70 (d, J=8.6 Hz, 1H), 6.65 (d, J=9.0 Hz, H), 6.52 (d, J=2.4 Hz, 1H), 6.47 (dd, J=8.6, 2.4 Hz, 1H), 5.21 (t, =7.2 Hz, 1H), 3.93 (s, 3H), 3.35 (d, J=7.2 Hz, 2H), 1.77 (s, 3H), 1.63 (s, 3H);

$^{13}$C NMR (101 MHz, Acetone-d) δ 193.8, 163.9, 163.7, 162.4, 160.0, 141.2, 131.8, 131.5, 130.4, 123.2, 117.5, 117.4, 115.5, 115.2, 109.2, 103.6, 103.0, 56.2, 25.8, 22.2, 17.8.

Synthesis of Dienophile 10

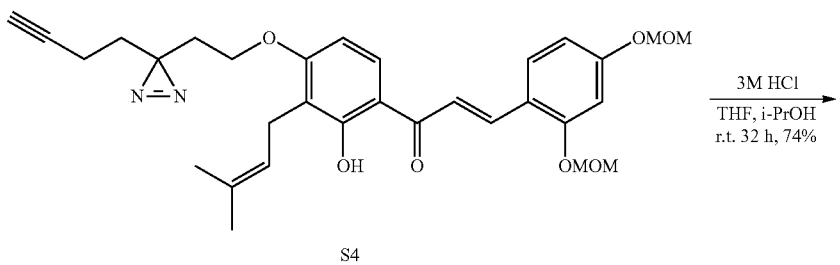

S4

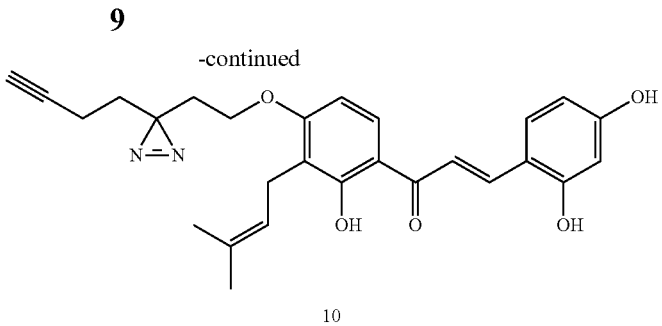

10

S4 (26.5 mg, 0.048 mmol) was dissolved in THF (0.6 mL) and i-PrOH (0.6 mL) at 0° C. 3M HCl aqueous solution (0.4 mL) was slowly added. The reaction mixture was slowly warmed to room temperature. After stirring for 32 h, the reaction was quenched by water and extracted by EtOAc. The organic layers were dried over anhydrous sodium sulfate. After purification by preparative TLC, Dienophile 10 was obtained (16.5 mg, 74%).

$^1$H NMR (400 MHz, Acetone-$d_6$) δ 13.95 (s, 1H), 8.25 (d, J=15.4 Hz, 1H), 8.04 (d, J=9.2 Hz, 1H), 7.84 (d, J=15.4 Hz, 1H), 7.71 (d, J=8.6 Hz, 1H), 6.63 (d, J=9.0 Hz, 1H), 6.53 (d, J=2.0 Hz, 1H), 6.47 (dd, J=8.6, 2.0 Hz, 1H), 5.30 (t, J=7.0 Hz 1H), 3.44 (d, J=7.2 Hz, 2H), 2.12-2.03 (m, 5H), 2.01 (t, J=6.0 Hz, 2H), 1.81 (s, 3H), 1.77 (t, J=7.6 Hz, 2H), 1.65 (s, 3H);

$^{13}$C NMR (101 MHz, Acetone-$d_6$) δ 193.8, 163.8, 162.8, 162.4, 160.0, 141.3, 131.8, 131.5, 130.3, 123.4, 117.8, 117.4, 115.6, 115.2, 109.2, 103.7, 103.6, 83.5, 70.6, 64.0, 54.9, 33.4, 33.1, 25.9, 22.4, 18.1, 13.6.

Synthesis of Diene 3

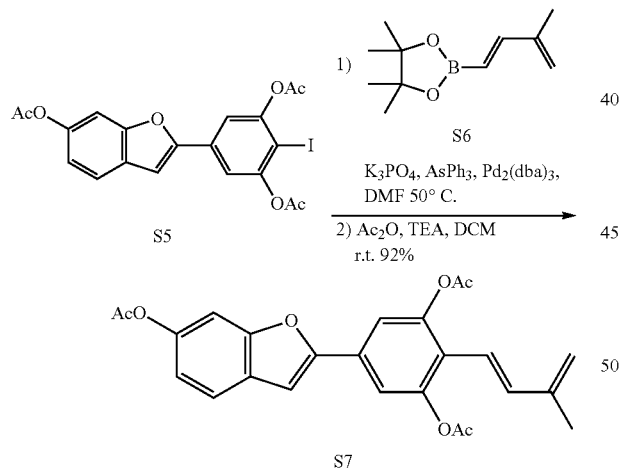

S5 (191.5 mg, 0.39 mmol) and S6 (301.2 mg, 1.53 mmol) were dissolved in DMF (40 mL), followed by adding $K_3PO_4$ (823 mg, 3.9 mmol), $AsPh_3$ (16.6 mg, 0.054 mmol), and $Pd_2(dba)_3$ (24.8 mg, 0.027 mmol). The reaction mixture was degassed by bubbling argon for 30 min, and the reaction was stirred at 50° C. for 5 h, and then quenched by water and extracted with EtOAc. The organic layer was dried with anhydrous sodium sulfate and spin dried to remove the solvent. The resultant was dissolved in DCM (20 mL), and then $Et_3N$ (539 μL, 3.9 mmol) and $Ac_2O$ (220 μL, 2.33 mmol) were added. After stirring at room temperature for 5 h, the reaction mixture was quenched by water and extracted with DCM. The organic layer was dried with anhydrous sodium sulfate. After purification by column chromatography (EtOAc/petroleum ether=1/10), Diene precursor S7 was obtained (155.3 mg, 92%).

$^1$H NMR (400 MHz, CDCl$_3$) δ 7.54 (dd. J=8.6, 4.8 Hz, 1H), 7.45 (d, =5.2 Hz, 2H), 7.45 (s, 1H), 7.26 (s, 1H), 7.08-6.96 (m, 2H), 6.92 (d, J=16.6 Hz, 1H), 5.13 (d, J=9.6 Hz, 2H), 2.34 (s, 3H), 2.33 (s, 6H), 1.93 (s, 3H);

$^{13}$C NMR (101 MHz, CDCl$_3$) δ 169.7, 168.8, 154.8, 153.0, 149.5, 148.3, 142.1, 138.3, 129.8, 126.8, 124.3, 121.2, 119.1, 117.8, 117.4, 116.9, 116.5, 105.2, 102.6, 21.0, 18.0.

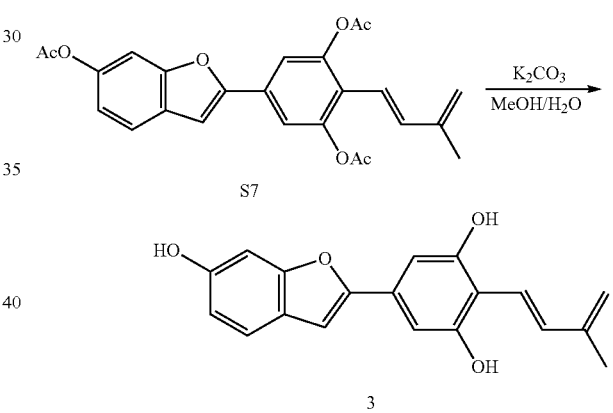

Diene 3 is unstable and can only be obtained by in-situ hydrolysis of its acetyl precursor S7: 5 volumes of methanol, 3 volumes of water and 1 volume of potassium carbonate aqueous solution (1M) were mixed together, and then 1 volume of S7 DMSO stock solution (100 mm) was added. After mixing and standing for reaction for 35 minutes, 10 mM solution of Diene 3 was obtained, and directly used for activity test.

Synthesis of Diene 23 and its Acetyl Precursor S10:

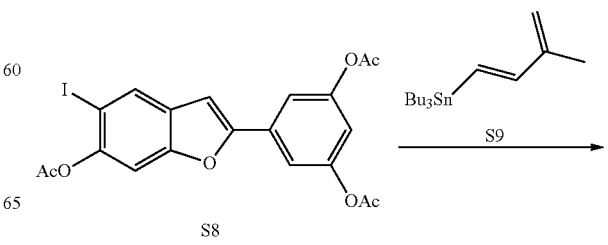

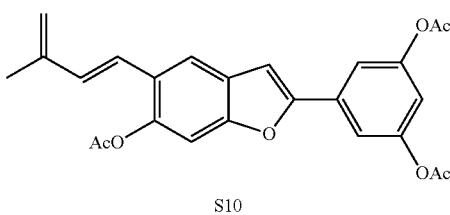

To a solution of S8 (15.9 mg, 0.0322 mmol) and S9 (17.0 mg, 0.0476 mmol) in DMF (0.6 mL) was added AsPh$_3$ (1.4 mg, 4.5 µmol) and Pd$_2$(dba)$_3$ (2.1 mg, 2.2 µmol) under argon atmosphere, and the reaction was performed at room temperature for 3.5 h. Then, the reaction was quenched by saturated ammonium chloride solution and extracted with Et$_2$O. The organic layers were combined and spin dried. After purification by column chromatography (EtOA/petroleum ether=1/4), Diene precursor S10 was obtained (13 mg, 93%)

$^1$H NMR (400 MHz, CDCl$_3$) 7.75 (s, 1H), 7.45 (d, J=2.1 Hz, 2H), 7.22 (s, 1H), 6.99 (s, 1H), 6.93 (t, J=2.0 Hz, 1H), 6.86 (d, J=16.1 Hz, 1H), 6.58 (d, J=16.1 Hz, 1H), 5.14 (s, 1H), 5.10 (s, 1H), 2.38 (s, 3H), 2.33 (s, 6H), 1.97 (s, 3H):

$^{13}$C NMR (101 MHz, CDCl$_3$) δ 169.5, 169.0, 155.4, 154.2, 151.5, 146.2, 142.0, 133.4, 132.2, 127.4, 126.5, 122.2, 118.1, 117.9, 115.7, 115.5, 105.8, 102.7, 21.2, 21.0, 18.6.

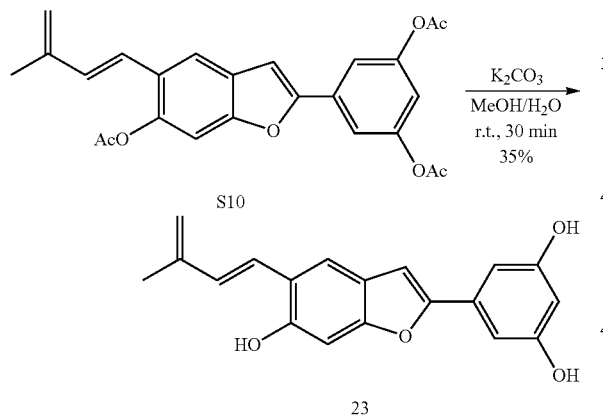

To a solution of Diene precursor S10 (10.3 mg, 0.024 mmol) in 0.8 ml of MeOH and 0.2 ml of H$_2$O (MeOH/H$_2$O=4:1) was added K$_2$CO$_3$ (16.4 mg, 0.119 mmol) under argon atmosphere. The reaction was performed at room temperature for 30 min, then quenched by saturated NH$_4$Cl solution and extracted with EtOAc. The organic layers were combined and spin dried. After purification by column chromatography (EtOAc/petroleum ether, 1/4), Diene 23 was obtained (2.6 mg, 0.0084 mmol, 35%).

$^1$H NMR (600 MHz, Acetone-d6) δ 8.78 (s, 1H), 8.35 (d, J=6.3 Hz, 2H), 7.74 (s, 1H), 7.04 (s, 2H), 7.02 (s, 1H), 7.00 (s, 1H), 6.86 (d, J=2.2 Hz, 2H), 6.37 (t, J=2.2 Hz, 1H), 5.11 (d, J=1.7 Hz, 1H), 5.03 (s, 1H), 1.99 (s, 3H);

$^{13}$C NMR (125 MHz, Acetone-d6) 159.8, 156.1, 155.9, 154.3, 143.6, 133.2, 131.2, 124.8, 123.1, 122.7, 118.4, 116.5, 103.8, 103.6, 102.3, 98.4, 18.8.

Synthesis of Diene 24 and its Acetyl Precursor S13

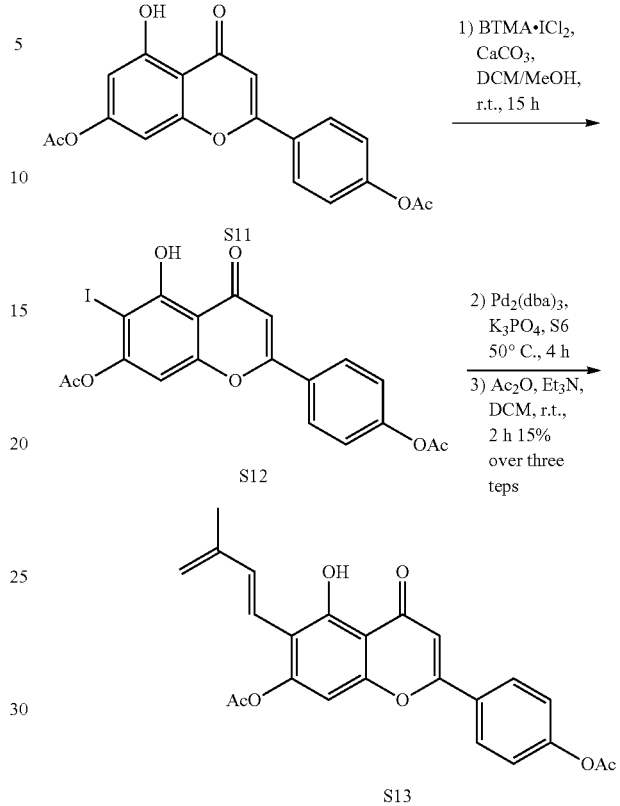

Compounds S11 (68.8 mg, 0.194 mmol) was dissolved in a mixed solution of 5 ml of DCM and 5 ml of MeOH, and then BTMA.ICl$_2$ (67.5 mg, 0.194 mmol) and CaCO$_3$ (194 mg, 1.94 mmol) were added. The resulting mixture was reacted at room temperature for 15 h and then filtered to remove CaCO$_3$. The resulting filtrate was extracted with DCM. The organic layers were combined and spin dried. The resultant was purified by column chromatography (MeOH/DCM=1/10) to obtain crude S12.

The crude S12 (70 mg, 0.146 mmol) and S6 (113 mg, 0.584 mmol) were dissolved in DMF (2 mL), then K$_3$PO$_4$ (318 mg, 1.46 mmol) and AsPh$_3$ (6.4 mg, 0.0204 mmol) were added. The reaction mixture was degassed by bubbling argon for 30 min to remove oxygen in the solution. Then Pd$_2$(dba)$_3$ (9.4 mg, 0.0102 mol) was added, and the reaction was performed at 50° C. for 5 h, and then filtered, and the filtrate was collected. The filtrate was spin dried and dissolved in DCM (4 mL), and then Et$_3$N (122 µL, 0.875 mmol) and Ac$_2$O (55.2 µL, 0.584 mmol) were added. After reacting at room temperature overnight, the reaction mixture was quenched by water and extracted with DCM. After purification by column chromatography (Acetone/Petroleum ether, 1/4), Diene precursor S13 was obtained (12.0 mg, 15% over three steps).

$^1$H NMR (400 MHz, Acetone-d6) δ 13.97 (s, 1H), 8.15 (d, J=8.6 Hz, 2H), 7.38 (dd, J=12.5, 9.2 Hz, 3H), 7.03 (s, 1H), 6.94 (s, 1H), 6.56 (d, J=16.5 Hz, 1H), 5.16 (s, 1H), 5.12 (s, 1H), 2.39 (s, 3H), 2.31 (s, 3H), 1.96 (s, 3H);

$^{13}$C NMR (101 MHz, Acetone-d6) δ 184.1, 169.3, 168.8, 164.8, 160.8, 155.7, 155.0, 154.9, 143.7, 137.4, 129.1, 128.9, 123.5, 118.4, 118.3, 114.8, 109.2, 106.4, 103.2, 21.0, 20.9, 18.1.

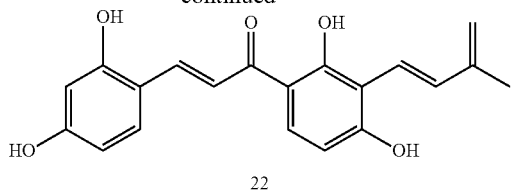

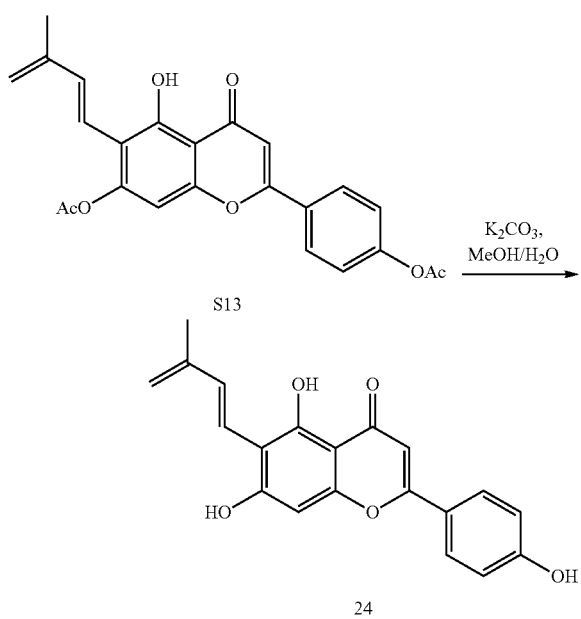

Diene 24 is unstable and can only be obtained by in-situ hydrolysis of its acetyl precursor S13:4 volumes of methanol, 3 volumes of water and 1 volume of potassium carbonate aqueous solution (1M) were mixed together, and then 2 volumes of S13 DMSO stock solution (50 mM) were added. After mixing and standing for 35 minutes, 10 mM solution of Diene 24 can be obtained and directly used for activity test.

Synthesis of Dienes 25 and 22

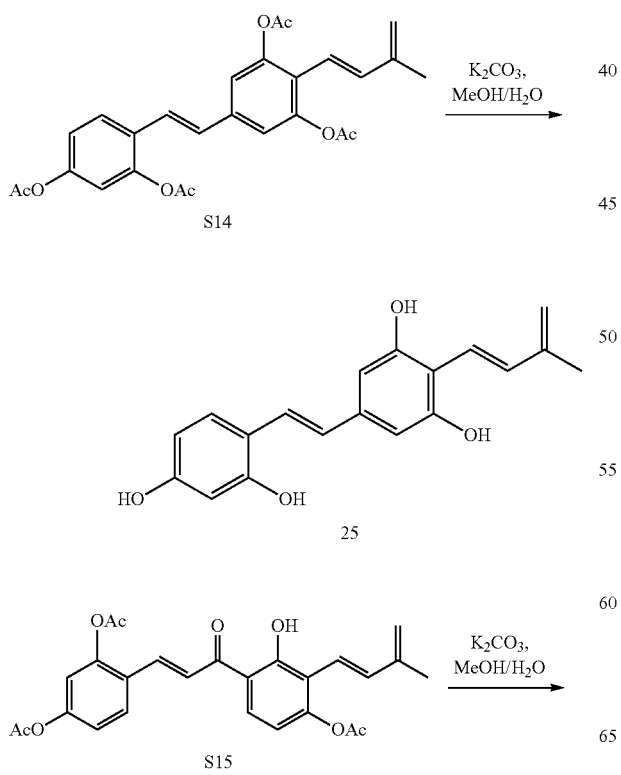

Diene precursor S14 was synthesized according to one literature (Gao, L., Han, J., Lei, X. Enantioselective total syntheses of kuwanon X, kuwanon Y, and kuwanol A, *Org. Lett.* 2016, 18, 360-363), and then subjected to in-situ hydrolysis with $K_2CO_3$ to generate Diene 25, and the operation was the same as the synthesis of Diene 3. Diene precursor S15 was synthesized according to one literature (Han, J., et al. Enantioselective biomimetic total syntheses of kuwanons I and J and brosimones A and B, *Angew. Chem. Int. Ed.* 2014, 53, 9257-9261), and then subjected to in-situ hydrolysis with $K_2CO_3$ to generate Diene 22, and the operation was the same as the synthesis of Diene 3.

Synthesis of Racemic Chalcomoracin (4)

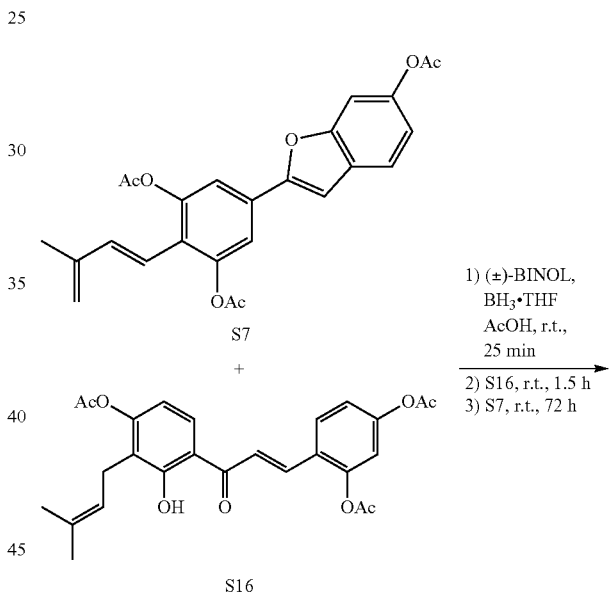

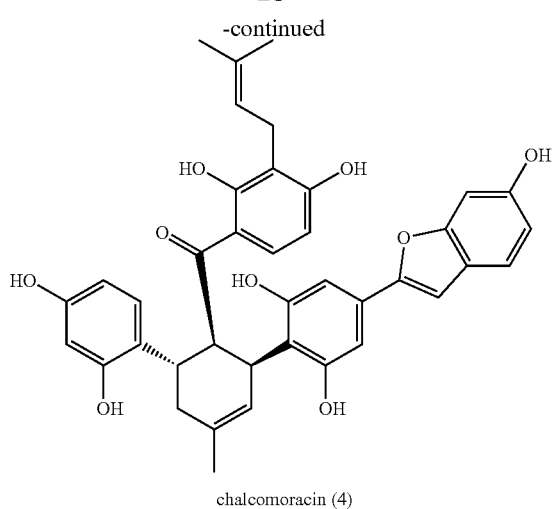

chalcomoracin (4)

Compound S16 was synthesized according to one literature (Han, J., et al. Enantioselective biomimetic total syntheses of kuwanons I and J and brosimones A and B, *Angew. Chem. Int. Ed.* 2014, 53, 9257-9261).

(±)-BINOL (25.4 mg, 0.107 mmol) was dissolved in THF (1.5 mL), and then $BH_3$.THF (51.5 μL, 0.0515 mmol) and AcOH (3.0 μL, 0.0515 mmol) were added. The resulting mixture was stirred at room temperature for 25 min, and then dried under high vacuum. THF (2.5 mL) was added into the resulting solid, and then 5 Å molecular sieve (200 mg) and Dienophile S16 (20.0 mg, 0.0429 mmol) were added. The resultant was reacted at room temperature for 1.5 h, and then S7 (22.4 mg, 0.0515 mmol) was added. The reaction mixture was reacted for 72 h, and then quenched by $H_2O$. The resultant was filtered, and the filtrate was collected and extracted with EtOAc, and then the resultant was spin dried. After purification by preliminary column chromatography (EtOAc/petroleum ether=1:5 to 1:2), crude S17 was obtained.

Rac-S17 (4.4 mg, 0.00489 mmol) was added to a mixed solution of MeOH (0.5 mL) and THF (0.25 mL), and then $K_2CO_3$ (6.7 mg, 0.0489 mmol) was added. The reaction was performed at room temperature for 1 h, and then quenched by 0.1N HCl aqueous solution (0.9 mL), and the resulting mixture was extracted with EtOAc and spin dried. After purification by column chromatography (MeOH/DCM=5: 95), racemic natural product chalcomoracin (4) was obtained. The NMR data of racemic natural product chalcomoracin (4) is consistent with the following literature: Takasugi, M., Nagao, S., Masamune, T., Shirata, A., Takahashi, K. Chalcomoracin, a natural Diels-Alder adduct from diseased mulberr. *Chem. Lett* 1980, 9, 1573-1576.

Example 1

1. Induction and Culture of the Cell Callus of the Mulberry Tree

The young leaves were superficially sterilized with 70% ethanol for 30 s, then sterilized with saturated sodium hypochlorite solution for 10 min, and then rinsed with 5 volumes of distilled water for 3 times. The sterilized leaves were cut into small pieces of about 1 $cm^2$ and inoculated on MS solid medium supplemented with NAA (naphthalene acetic acid) 0.5 mg·$L^{-1}$+6-BA (6-benzylaminoadenine) 0.5 mg·$L^{-1}$+2,4-D (2,4-dichlorophenoxyacetic acid) 0.2 mg·$L^{-1}$, at pH 5.8. The callus was induced under dark conditions. Expanded culture was carried out by inoculating the induced callus on the above-mentioned MS solid medium, subculture was performed every 4 weeks, and the culture temperature was 25±1° C. Mulberry suspension cell line was established by inoculating the callus with good growth condition into the same MS liquid medium. The suspension cell line was cultured on a shaker at 25±1° C. in darkness at 110 r·$min^{-1}$.

2. Component Analysis of D-A Type Natural Products in the Mulberry Cell Callus.

Figure 4:
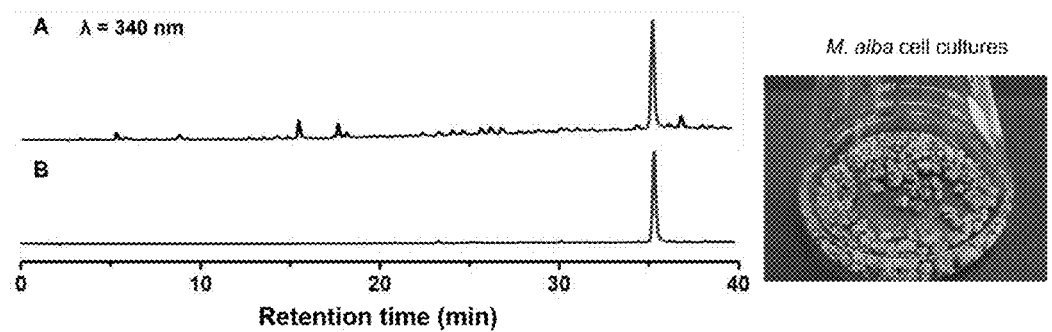
FIG. 4 shows the HPLC analysis results of the crude extract from cell callus of Morus alba. A is the high performance liquid chromatography (HPLC) analysis result of the chemical components of the cell callus; B is the standard substance of natural product chalcomoracin.

0.1 g dried mulberry callus was weighed and added into 1.5 mL EP tube. Then 1 ml methanol aqueous solution (methanol:water=4:1) was added, and sonicated twice. After filtration with 0.22 μL filter membrane, the callus crude extract was obtained. The crude extract was analyzed by HPLC, and the results as shown in A in FIG. 4 were obtained. Compared with chalcomoracin standard (B in FIG. 4), the cell callus of the present invention is rich in D-A type natural product chalcomoracin. This indicates that Diels-Alderases catalyzing the synthesis of chalcomoracin exists and may be highly expressed in the cell callus of the present invention.

3. Activity-Based Protein Purification

1). Preparation of the Cell Crude Enzyme Solution

Fresh *M. alba* cell cultures (200 g) was added into lysis buffer (400 ml) that consisted of 50 mM sodium phosphate (pH 7.4), 1 mM EDTA, 3 mM 2-mercaptoethanol and 100 mM phenylmethanesulfonyl fluoride at a ratio of 1:100 (v/v) and treated with a Waring blender at 4° C. The mixture was centrifuged at 9,000 g at 4° C. for 30 min, and the supernatant was collected and added into a 500 ml Erlenmeyer flask for precipitation. Solid ammonium sulfate (AS) was added to the supernatant to 80% saturation. After gentle agitation at 4° C. for 12 h, the mixture was distributed into the test tube and centrifuged at 9,000 g at 4° C. for 30 min. The resulting pellet was resuspended in a buffer that contained 20 mM Tris-HCl (pH 7.4), 2 mM EDTA and 3 mM 2-mercaptoethanol, and then transferred to new test tube. The protein sample was centrifuged at 160,000 g at 4° C. for 2 h to remove particulates. The supernatant was collected and concentrated using a centrifugal concentrator with Amicon Ultra-30K (Millipore) to obtain the cell crude enzyme solution.

2). Purification by Hydrophobic Column Chromatography

The above cell crude enzyme solution was loaded onto a Hitrap Butyl FF column (5 ml) equilibrated with a 50 mM sodium phosphate buffer (pH 7.0, containing 1.5 M AS). Protein elution was performed at a flow rate of 2 ml/min using a 50 mM sodium phosphate buffer (pH 7.0), with the following gradient: 0 to 20 min at 0% (v/v), 20-70 min at 20% (v/v) and 70-120 min at 100% (v/v).

3). Purification by Ion Exchange Column Chromatography

The active fractions from the above Hitrap Butyl FF chromatography were collected, and buffer-exchanged to 20 mM Tris-HCl, pH 8.0, and loaded onto a HiTrap Q FF (5 mL) column (GE Healthcare, USA) equilibrated with 20 mM Tris-HCl, pH 8.0. Protein elution was performed at a flow rate of 2 ml/min using a buffer that contained 20 mM Tris-HCl, pH 8.0, and 1 M NaCl with the following gradient: 0-20 min at 0% (v/v), 20-40 min at 10% (v/v), 40-60 min at 20% (v/v) and 60-100 min at 100% (v/v).

4). Purification by Size Exclusion Column Chromatography (SEC)

The active fractions from the above HiTrap Q chromatography were concentrated and fractionated using Superdex 200 Increase 10/300 GL columns (GE Healthcare, USA)

connected in series. Isocratic protein elution was performed at a flow rate of 0.25 ml/min using a buffer that contained 20 mM Tris-HCl (pH 7.2) and 0.15 M NaCl. The eluted fractions were tested for activity by Agilent 126 HPLC. Gel filtration chromatography (size-exclusion chromatography) was performed using the NGC™ chromatographic system.

5). Activity Tests was Performed on Different Protein Fractions After Purification 9.8 μg of different proteins obtained from the above-mentioned steps 1-4 was added to a reaction liquid, which contained 20 mM Tris-HCl (pH 7.5), 100 μM dienophile morachalcone A (1) and 100 μM moracin C (2), to a final volume of 100 μl. The resultant reaction mixture was incubated at 30° C. for 1 h. The reactions were terminated by the addition of 200 μl of ice-cold MeOH and were centrifuged at 15,000 g for 30 min. The supernatants were analyzed by HPLC-MS. When the cell crude enzyme solution or the purified active protein fraction was not added into the reaction liquid, Dienophile 1 and the diene precursor moracin C (2) will not change, as shown in FIG. 5A. Diene 3 and the corresponding D-A natural product chalcomoracin (4) can be detected after addition of cell lysate, as shown in the FIG. 5B; Diene 3 and the D-A natural product chalcomoracin (4) can also be detected when the active protein fraction purified by hydrophobic column chromatography was added into the reaction liquid, as shown in FIG. 5 C. When the active protein fraction purified by ion-exchange column was added into the reaction liquid, the production of D-A natural product 4 increased, as shown in FIG. 5D. When the active protein fraction purified by gel filtration chromatography was added to the reaction liquid, the production of D-A natural product 4 increased significantly, as shown in FIG. 5E, and this indicated that the Diels-Alderase might be enriched in this fraction.

4. SDS-PAGE Analysis of Different Protein Fractions

The concentration of each protein fraction was diluted to 0.4 μg/μL, and 25 μL protein sample was added with 5 μL loading buffer, then heated at 100° C. for 5 min, and analyzed by 12% SDS-PAGE. After electrophoresis, Coomassie brilliant blue staining was performed to obtain the results as shown in FIG. 6. By comparing the protein bands in different protein fractions, an obvious enrichment band in the SEC fraction was observed, which band was indicated with an arrow in FIG. 6, this band was used as a candidate protein band, and was subsequently analyzed by protein mass spectrometry.

5. LC-MS-MS Protein Mass Spectrometry Analysis

The enriched bands were cut off and sent to National Institute of Biological Sciences, Beijing (NIBS) for LC-MS/MS analysis, and the obtained peptide information was aligned with *Morus notabilis* protein sequences so as to obtain information of proteins in the enrichment band, as shown in FIG. 7. It is believed that the enrichment band is very likely to be a type of reticuline oxidase-like protein in mulberry. It is speculated that this type of protein might be an enzyme that catalyzes the intermolecular D-A reaction.

Example 2 Transcriptome Analysis of Cell Callus of *Morus alba*

0.1 mm Methyl jasmonate was added into the medium of the cell callus which had been growing for about 10 days. After 20 hours of induction, the cell callus was sent to BGI for transcriptome sequencing. In the obtained transcriptome data, a total of 14 transcripts annotated as reticuline oxidase like oxidase or its homologous protein (cannabidiolic acid synthase) were found. According to the size of fragments per kilobase of exon per million reads mapped (FKPM), these proteins were sorted according to the transcriptional levels, and the result is shown in FIG. 8.

1. Extraction of Total RNA from Cell Callus of *Morus alba*

100 g fresh cell callus was added into a mortar, and grinded to powder with liquid $N_2$. The total RNA from the cell callus was extracted using the plant total RNA extraction kit from Tiangen Biotech., Beijing following the protocol as follows.

1) To 100 mg of ground sample in 1.5 ml EP tube, 450 μL lysis solution was added, and then shaken vigorously to mix well, and centrifuged (15000×g, 5 min). the supernatant was collected.

2) The supernatant was transferred to the filter column CS (the filter column CS was placed in the collection tube), and centrifuged at 12,000 rpm (13400×g) for 2 to 5 min. The supernatant in the collection tube was carefully sucked into the RNase free centrifuge tube. The aspirator should avoid contacting with the cell debris precipitation in the collection tube.

3) 0.5 volume of the supernatant volume of absolute ethanol (about 225 μL) was slowly added and mixed well, then the obtained solution and precipitation were transferred into the adsorption column CR3, and centrifuged at 12,000 rpm (~13400×g) for 30 to 60 seconds, the waste liquid in the collection pipe was poured out, and the adsorption column CR3 was put back into the collecting tube.

4) 350 μL deproteinized solution RW1 was added to the adsorption column CR3, centrifuged at 12,000 RPM (~13400×g) for 30 to 60 sec. The waste liquid in the collection tube was poured out, and the adsorption column CR3 was put back into the collecting tube.

5) 80 μL DNase I working solution was added into the center of CR3 column and placed at room temperature for 15 min.

6) 350 μL deproteinized solution RW1 was added to the adsorption column CR3, centrifuged at 12,000 RPM (~13400×g) for 30 to 60 sec. The waste liquid in the collection tube was poured out, and the adsorption column CR3 was put back into the collecting tube.

7) 500 μL rinsing solution RW was added to the adsorption column CR3, stood at room temperature for 2 min, and centrifuged at 12,000 rpm (~13400×g) for 30 to 60 sec, the waste liquid in the collection pipe was poured out, and the adsorption column CR3 was put back into the collection pipe.

8) Step 7 was repeated.

9) The resultant was centrifuged at 12,000 rpm (~13400× g) for 2 min, and the waste liquid was poured out. The adsorption column CR3 was placed at room temperature for several minutes to dry the remaining rinsing solution in the adsorption material thoroughly.

10) The adsorption column CR3 was put into a new RNase-free centrifuge tube, 30-100 μL of RNase-free $ddH_2O$ was added to the middle part of the adsorption membrane, placed at room temperature for 2 min, and centrifuged at 12,000 rpm (~13400×g) for 2 min to obtain a RNA solution.

2. The Preparation of cDNA of Cell Callus of *Morus alba*

The total extracted RNA was treated with DNAase at 37° C. for half an hour, then purified with RNA Purification Kit, and its recovery concentration was determined by nanodrop. The cDNA was obtained by reverse transcription with Thermo Scientific RevertAid First Strand cDNA Synthesis Kit.

3. The Amplification of the MaDA Gene

Upstream primer sequence:
(SEQ ID No. 5)
5'-AACCTGTATTTTCAGGGATCCAACGACACTCATGAAGCCTTTCTTG-3'

Downstream primer sequence:
(SEQ ID No. 6)
5'-CTCGAGACTGCAGGCTCTAGATCACATTGCTGAATGTAGAGGAGGAAGAG-3'

PCR Reaction System (50 µL):

| | |
|---|---|
| Template cDNA | 1 µL |
| Upstream primer | 1.5 µL |
| Downstream primer | 1.5 µL |
| 5 × Transstart Fastpfu Buffer | 10 µL |
| Transstart fastpfu DNA polymerase | 1 µL |
| 10 mM dNTPs | 4 µL |
| ddH$_2$O | 31 µL |

PCR cycle conditions (50 µL system) were as follows: 95° C. for 2 min, 98° C. for 30 s, 52° C. for 30 s, 72° C. for 1 min, 32 cycles in total; 72° C. 5 min.

Figure 9:
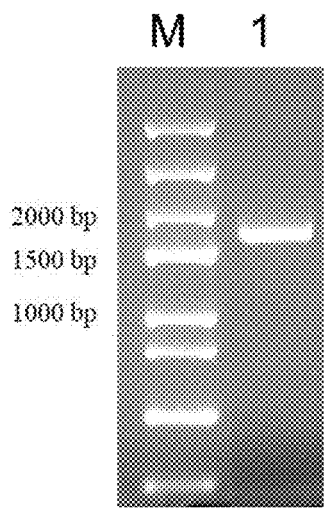
FIG. 9 shows the agarose gel electrophoresis map of MaDA gene. M is nucleic acid marker and lane 1 is MaDA gene nucleic acid.

1% agarose gel electrophoresis of PCR product was carried out after PCR, as shown in FIG. 9, and the specific band was recovered and purified.

4. The Construction of Baculovirus

The Bac-to-Bac system developed by Invivogen Company was used:

pI-secSUMOstar-tev2 empty vector was subjected to double enzyme digestion with BamHI and XbaI, and after 1% agarose gel electrophoresis, a single band was recovered with a gel recovery kit, and the concentration of recovered DNA was measured with nanodrop. Vazyme homologous recombinase was used to generate the pI-secSUMOstar-tev2-MaDA plasmid. The ligation system (10 µL) was composed of 1 µL Exnase II, 2 µL 5-CE buffer, 3 µL linearized vector, 4 µL PCR product of MaDA.

In the above ligation system, the molar ratio of MaDA to linearized pI-sec-sumostar-tev2 vector was about 2:1. After 30 min ligation reaction at 37° C., the reaction system was placed on ice immediately. Then, the linked products were added into 100 µL DH5α competent cells. After 30 min of ice bath, heat shock was performed at 42° C. for 1 min, and then immediately put the mixture on ice for 3 min, then 1 ml LB medium was added and cultured at 37° C. and 220 rpm. After about one hour of incubation, the resultant was centrifuged to discard 900 µl culture media. The cells were suspended in the remaining 100 µL medium and then inoculated on a solid LB plate containing ampicillin (100 µg/ml) by pipette. After overnight culture at 37° C., the monoclonal cells on solid medium were selected and cultured in LB liquid medium for 12 to 16 hours, and then the plasmids were extracted and sequenced.

1 µg pI-sec-sumostar-tev2-MaDA was added into 100 µL DH10Bac competent cells. After 30 min of ice bath and heat shock at 42° C. for 1 min, the resulting mixture was then placed on ice for about 3 min, and then 1 ml LB liquid medium was added. After incubation at 37° C. and 220 rpm for about 4 hours, the bacterial solution was diluted with 5 mL liquid LB medium, and 100 µL diluted solution was inoculated on a solid LB plate containing kanamycin (50 µg/mL), gentamicin (7 µg/mL), tetracycline (10 µg/mL), IPTG (40 µg/mL) and Bluo-gal (100 µg/mL). After overnight culture at 37° C., 3 to 4 large white clones were selected and inoculated into liquid LB containing kanamycin (50 µg/mL), gentamicin (7 µg/mL), tetracycline (10 µg/mL) for overnight culture. The E. coli strains cultured overnight were collected, and the Bacmid was purified using isopropanol precipitation method. The Bacmid was verified by PCR and the primers were as follows:

Upstream primer sequence:
(SEQ ID No. 7)
5'-AAATGATAACCATCTCGC-3'

Downstream primer sequence:
(SEQ ID No. 8)
5'-GGAGGATAACGATATTATTGAGGC-3'

PCR Reaction System is:

| | |
|---|---|
| Bacmid | 1 µL |
| Upstream primer | 1.5 µL |
| Downstream primer | 1.5 µL |
| 5 × Transstart Fastpfu Buffer | 10 µL |
| Transstart fastpfu DNA polytnerase | 1 µL |
| 10 mM dNTPs | 4 µL |
| ddH$_2$O | 31 µL |

The Bacmid containing the target gene (confirmed by PCR as positive) was transfected into Sf21 insect cells and adherently cultured in SIM-SF medium for 96 hours to obtain P1 generation baculovirus. The sf21 cells were suspension cultured, and when the cell density reached $1.5 \times 10^6$ to $2.5 \times 10^6$ cells/mL, P1 generation baculovirus was added at a volume ratio of 1:200, and P2 generation baculovirus was obtained % hours later.

5. Expression of the Secretory Protein

Figure 10:
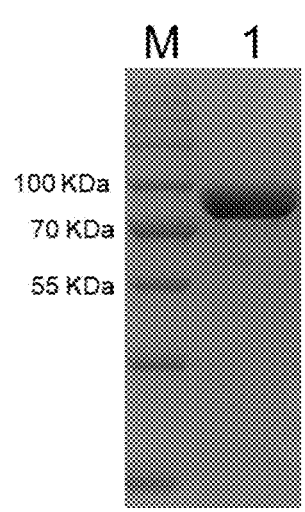
FIG. 10 is the SDS-PAGE map of SUMO-MaDA protein.

Insect cells Hi5 was used as protein expression system. Hi5 cells were suspension cultured in SIM-HF medium and infected with recombinant baculovirus when the cell density reached $1.5 \times 10^5$ to $2.5 \times 10^6$ cells ml$^{-1}$. The cells were removed by centrifugation after 48 h. and the supernatant was collected. The supernatant was concentrated and then buffer-exchanged using viva flow 200 enrichment facility from Sartorius company. Then, the target protein with His tag was purified by nickel ion chelating affinity chromatography, as shown in FIG. 10.

Example 3 Enzyme Activity Test of MaDA

1) Determination of the Scope of Application of Dienophile Substrate

To 97 µL reaction buffer (20 mM Tris-HCl, pH 8.0) was added 1 µL Diene 3 (final concentration, 100 µM) and 1 µL different chalcones or their derivatives (final concentration, 100 µM). Then 1 µL SUMO-MaDA (final concentration, 2.7 nM) was added, and the resulting mixture was reacted at 50° C. for 10 min. The reactions were terminated by the addition of 200 µl of methanol and centrifuged at 13,000 rpm for 30 min. Supernatants were analyzed by HPLC.

The HPLC condition was as follows:
column: Shiseido MGIII C18 (250 mm×4.6 mm, 5 µm); mobile phase: methanol-water (0.1% formic acid); The gradient programs were as follows: 40→70% methanol, 0-15 min; 70→100% methanol, 15-35 min; 100→40% methanol, 35-45 min. Flow rate: 1.0 mL min$^{-1}$, detection wavelength: 340 nm, column temperature: 25° C.; and injection volume: 10 µL.

Figure 11A:
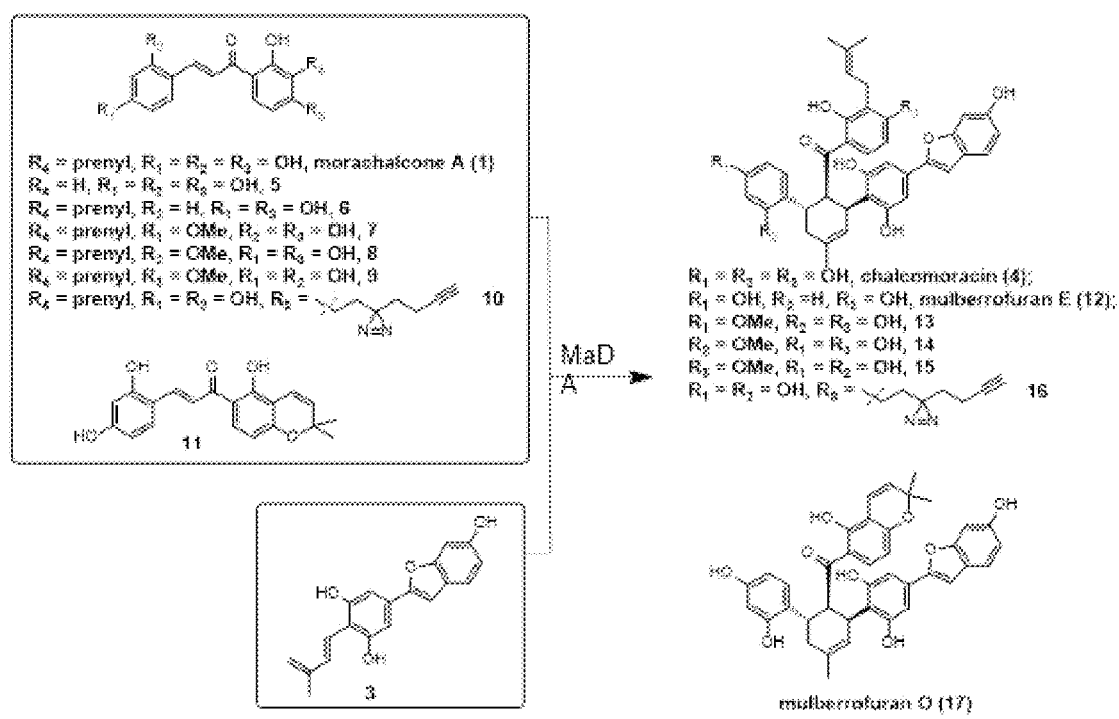
FIG. 11A shows the structures of different dienophiles and corresponding D-A products
Figure 11B:
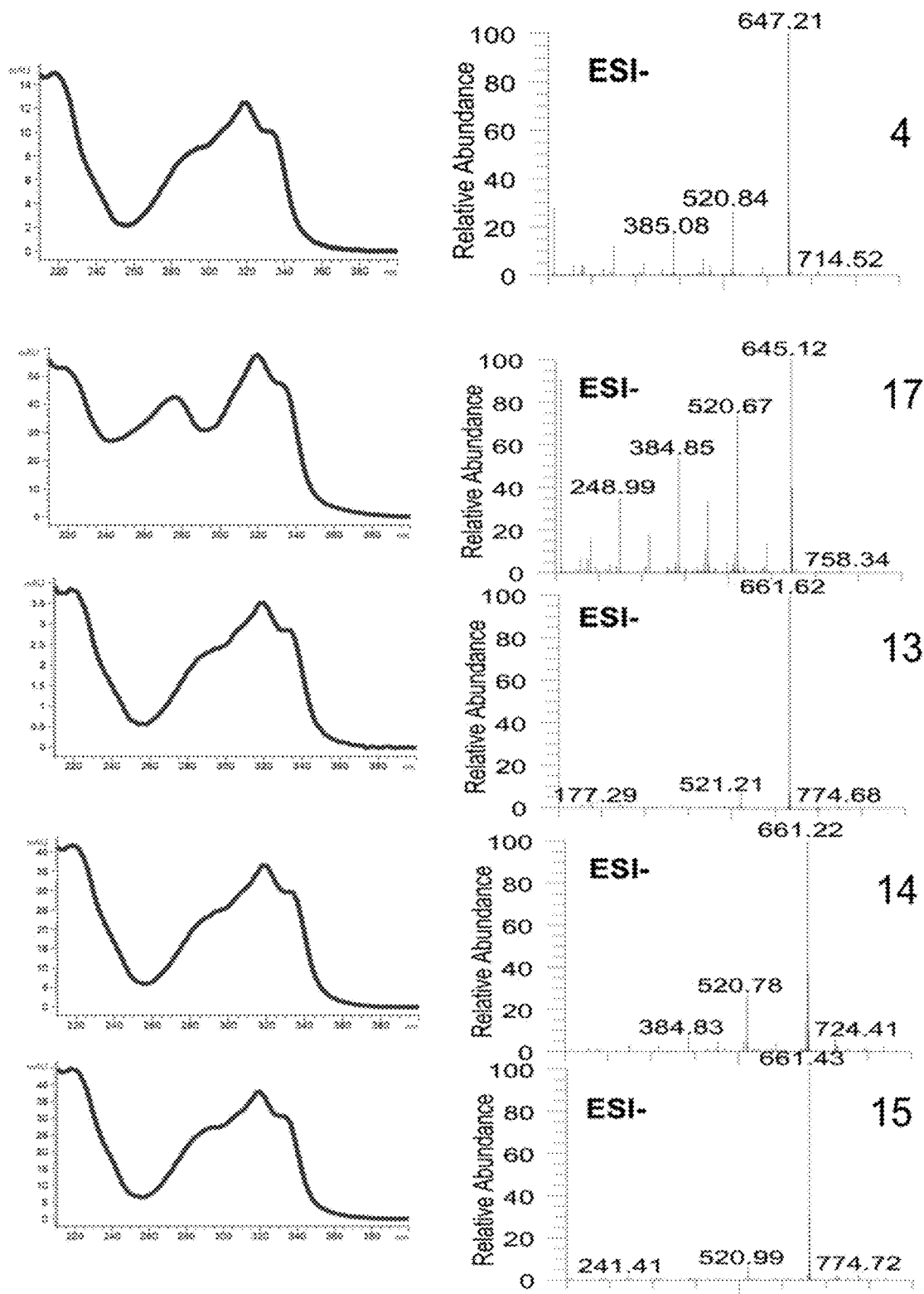
FIG. 11B shows the UV absorption and mass spectrometry results of D-A products.
Figure 11C:
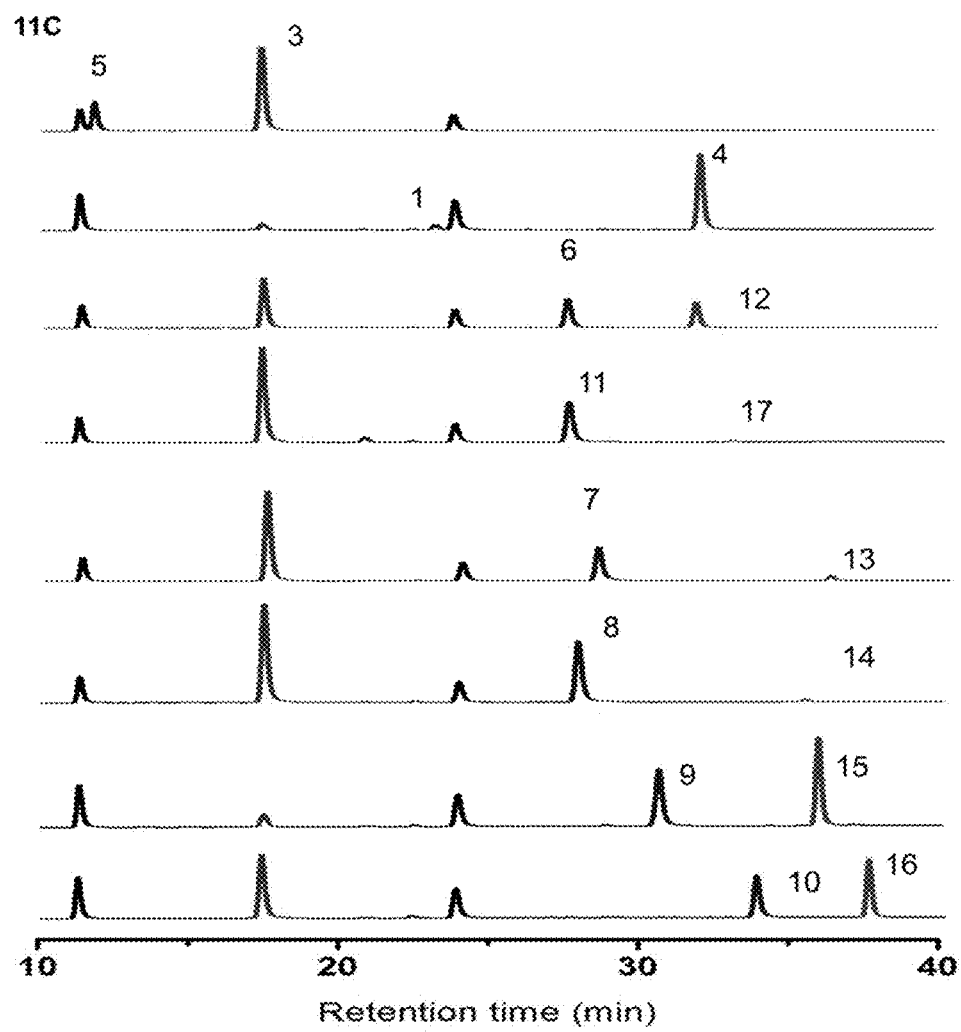
FIG. 11C shows the HPLC results of the activity test.

The structures of different dienophiles and corresponding D-A products were shown in FIG. 11A; the UV absorption and mass spectrometry results of D-A products were shown in FIG. 11B, and the HPLC analysis results were shown in FIG. 11C. MaDA can recognize different substituted chalcones and their derivatives (compounds 1, 6-11) to generate the natural product mulberofurans E/O, chalcomoracin and its derivatives, showing good substrate adaptability, but could not recognize chalcone 5 without prenyl group. In order to further confirm the structure of the products, the natural product chalcomoracin (4) and its derivative 13 were prepared through large-scale enzymatic reactions, and their structures was confirmed to be consistent with the reported structures. See Example 3 for details.

2) Determining conversion of some dienophile substrates

Figure 12:
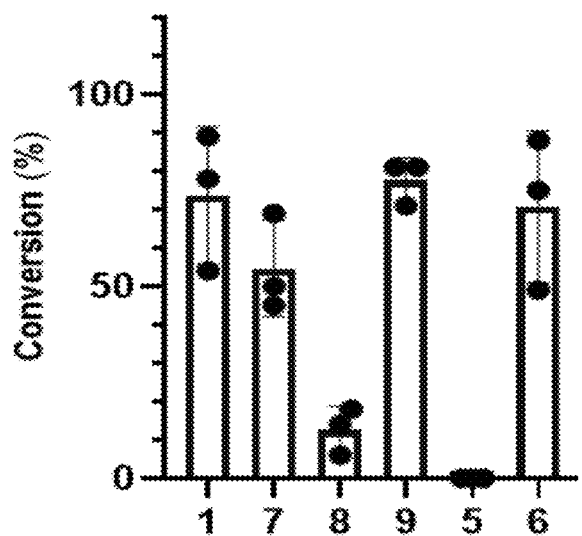
FIG. 12 shows the determination results of conversion of some dienophiles.

In the present Example, the conversion of Dienophiles 1 and 5-9 under enzymatic D-A reaction conditions were also determined. The reaction conditions were as follows:

To 96 μL reaction buffer (20 mM Tris-HCl, pH 8.0) was added 2 μL Diene 3 (final concentration, 200 μM) and 1 μL different chalcones or their derivatives (i.e., Dienophiles 1 and 5-9, final concentration, 100 μM). Then 1 μL MaDA or SUMO-MaDA (final concentration, 540 nM) was added. The resulting mixture was reacted at 50° C. for 5 min. The reactions were terminated by the addition of 200 μl of methanol. The reaction liquid were analyzed using the HPLC analysis condition mentioned above. After three repeated experiments, the conversion of Dienophiles 1, 7, 8, 9, 5 and 6 are determined as 74%, 55%, 13%, 78%, 0%, 71% respectively, as shown in FIG. 12. These results showed that under this reaction condition, MaDA protein could effectively recognize Dienophiles 1, 6 and 9 to synthesize the corresponding D-A natural products or their derivatives.

3) Determination of the Scope of Application of Diene Substrates

Figure 13:
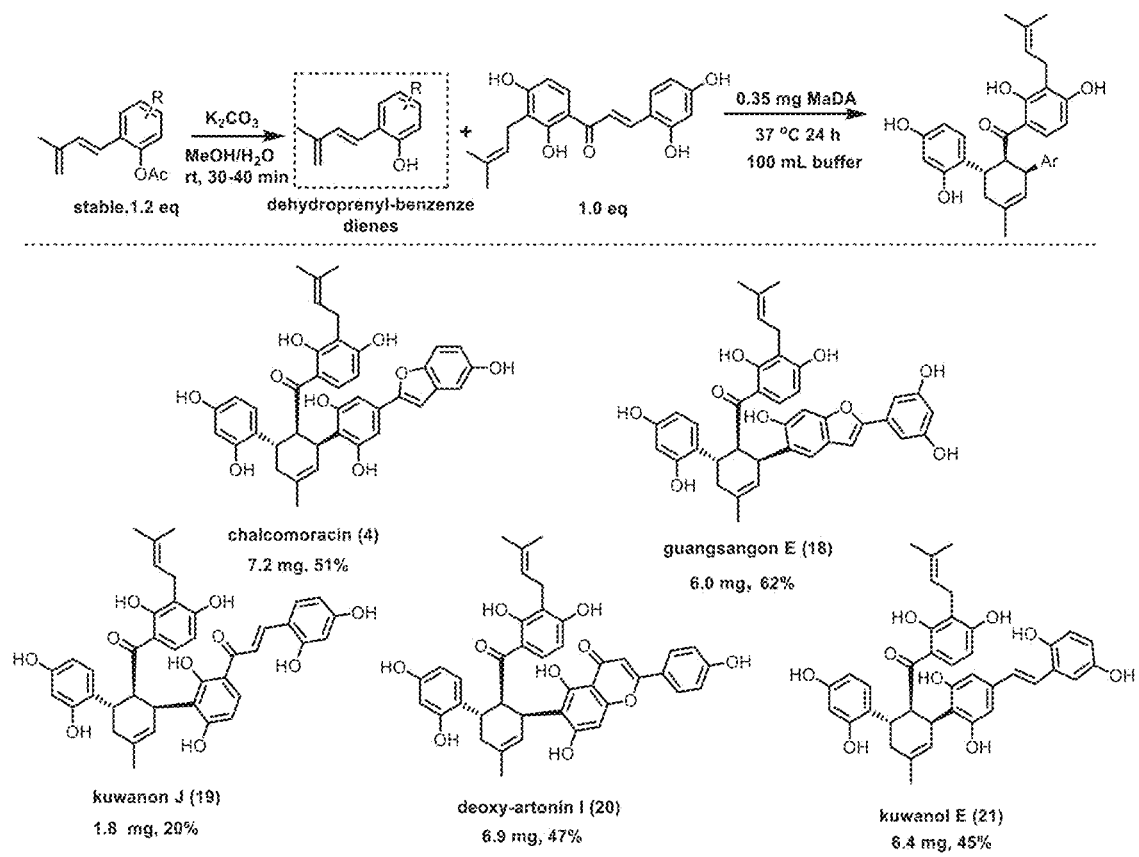
FIG. 13 shows the enzymatic synthesis of D-A natural products.

In the present Example, many dienes with dehydroprenyl group were also obtained by chemical synthesis. Then, the reaction efficiencies between different dienes and Dienophile 1 were determined. The reaction conditions and experimental results were shown in FIG. 13. The specific procedure was as follows: the acetyl precursor of corresponding diene (0.026 mmol, 1.2 equivalents) was dissolved in a 1 mL mixture of water and methanol (water:methanol=1:4), and then potassium carbonate (0.087 mmol, 5.0 equivalents) was added. After stirring at room temperature for 35 minutes, the mixture was added to 48 ml of reaction buffer (20 mm Tris-HCl, pH=8.0), Then, 0.35 mg SUMO-MaDA enzyme and 7.4 mg dienophile 1 (0.022 mmol, 1.0 equivalent, dissolved in 0.34 ml DMSO) were added to the reaction system. After mixing well, the resultant was incubated in static at 37° C. for 14 to 18 hours. Then 50 ml saturated ammonium chloride solution was added to quench the reaction, and then the mixture was extracted with ethyl acetate (50 ml) for three times and then spin dried. The final product was separated and purified by C18 reverse high performance liquid chromatography (Waters, XBridge@ pre C18 OBD™, 150 mmx 19 mm i.d., 5 μm), as shown in FIG. 13. The liquid phase preparation system was water (A) and acetonitrile (B), with the following gradient: 50%-80% B, 0-5 min; 80%-95% B, 5-12 min; 95%-95% B, 12-15 min; 95-50% B, 15-16 min; and 50% B, 16-18 min.

From the above results, it can be seen that MaDA enzyme has certain activity towards Dienes 3 and 22-25, and can specifically produce endo products, showing good substrate adaptability and selectivity. Five different types of D-A type natural products can be obtained in high yield (up to 62%) by two-step tandem reactions of in-situ formation of unstable dienes under alkaline conditions and asymmetric D-A reaction catalyzed by MaDA.

Figure 14:
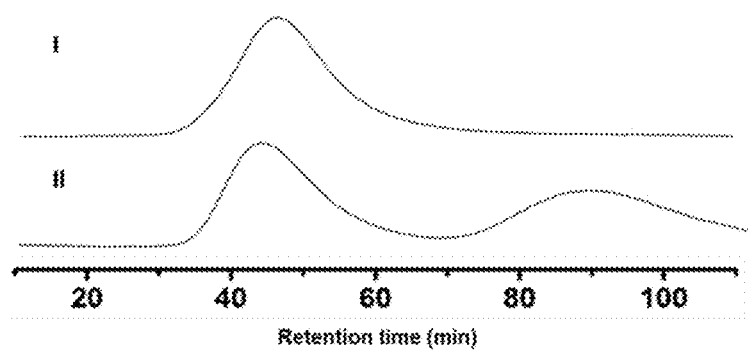
FIG. 14 shows the determination of enantioselectivity of the D-A product chalcomoracin (4). i) shows the chiral HPLC analysis of the enzymatically obtained chalcomoracin (4); ii) shows the chiral HPLC analysis of the racemic chalcomorcin.

The ee value of chalcomoracin (4) prepared by the enzymatic method was also determined. The results proved that the D-A reaction catalyzed by MaDA was not only endo-selective, but also stereospecific, as shown in FIG. 14. This indicates that MaDA has certain application value in stereospecific synthesis of D-A type natural products.

4) Determination of Optimum Temperature and pH of MaDA

Figure 15:
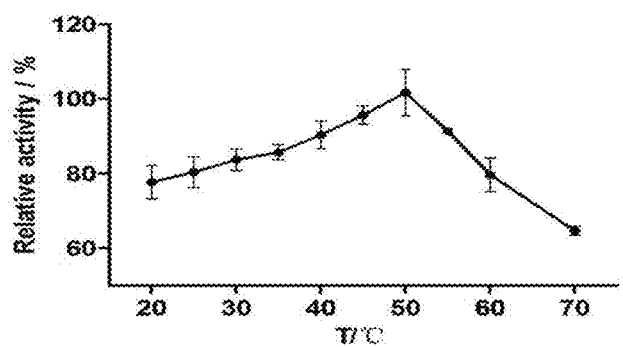
FIG. 15 shows the optimum temperature determination results of MaDA protein.

The effects of different reaction temperatures (25, 30, 35, 40, 45, 50, 55, 60, and 70° C.) on [4+2] cyclization catalyzed by MaDA were investigated using Diene 3 and Dienophile 1 as substrates. The reaction system was as follows: the reaction mixture (100 μL) containing Diene 3 (0.1 mM) and Dienophile 1 (0.1 mM), and 0.02 μg MaDA was reacted for 5 min in Tris HCl buffer at pH 7.5 (the buffer solution was balanced at different temperatures for 15 min in advance). After the reaction, 200 μL ice-cold methanol was added to terminate the reaction, and vortex mixing was carried out. The resulting mixture was centrifuged at 15,000 g for 30 min. The supernatant was analyzed by HPLC. Three reactions in each group were parallel. The conversion of the substrate was calculated by substituting the peak area of the product into the standard curve to calculate the reduction of the substrate. Finally, the relative activity of MaDA at different temperatures was obtained, as shown in FIG. 15.

Figure 16:
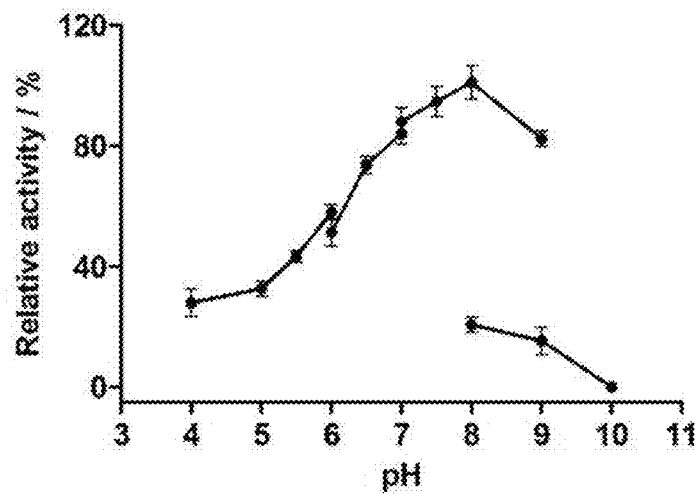
FIG. 16 shows the optimum pH determination results of MaDA protein.

The effects of buffer at different pH (pH 4.0-6.0, citric acid-sodium citrate buffer; 6.0-7.0, disodium hydrogen phosphate-sodium dihydrogen phosphate buffer; 7.0-9.0, Tris HCl buffer; 9.0-11.0, sodium carbonate-sodium bicarbonate buffer) on the [4+2] cyclization reaction of MaDA was investigated using Diene 3 and Dienophile 1 as substrates. The reaction system was as follows: the reaction mixture (100 μL) containing Diene 3 (0.1 mM) and Dienophile 1 (0.1 mM), and 0.02 μg MaDA was reacted for 5 min in different buffer with different pH (the buffer solution was balanced at different reaction temperatures for 15 min in advance). After the reaction, 200 μl of cold methanol was added to terminate the reaction, and vortex mixing was performed. The supernatant was centrifuged at 15,000 g for 30 min. The supernatant was analyzed by HPLC. Three reactions in each group were parallel. The conversion of the substrate was calculated by substituting the peak area of the product into the standard curve to calculate the reduction of substrate. The relative activity of MaDA at different pH was obtained, as shown in FIG. 16.

Example 4 Application of MaDA

1. The Preparation of Chalcomoracin (4) Using MaDA as Catalyst

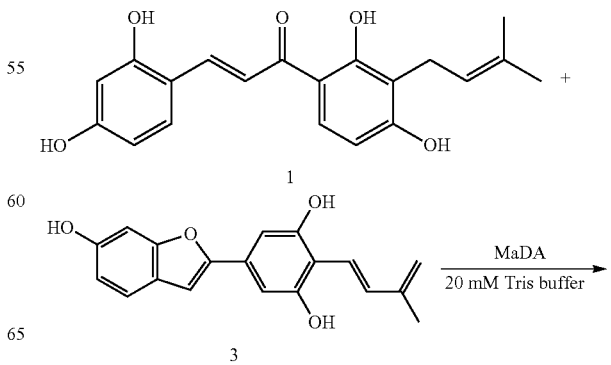

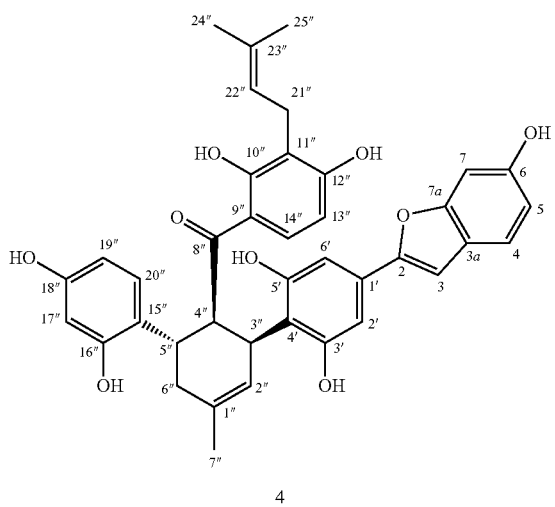

4

Diene precursor S7 (11.3 mg, 0.0261 mmol) was added to 1 mL mixture solution of MeOH and H$_2$O (MeOH/H$_2$O=4:1) and then K$_2$CO$_3$ (18.0 mg, 0.131 mmol) was added. The resulting mixture was reacted at room temperature for about 35 min to generate Diene 3 in situ. Then the resulting solution was added to 98 mL reaction solution (59 nM MaDA in 20 mM Tris-HCl, H=8.0). To this mixture, dienophile morachalcone A (1, 7.4 mg dissolved in 0.37 mL DMSO) was added. The resulting mixture was reacted at 37° C. overnight. The resulting mixture was extracted with ethyl acetate. The organic layers were combined and spin dried, and purified by HPLC to give natural product chalcomoracin (4) (7.2 mg, 51%).

$[\alpha]_D^{20}$+178.8° (c 0.10, MeOH);

$^1$H NMR (600 MH z, Acetone-d$_6$) δ 8.44 (1H, d, J=9.0 Hz, H-14"), 7.34 (1H, d, J=8.4 Hz, H-4), 6.98 (1H, d, J=8.4 Hz, H-20"), 6.93 (1H, s, H-7), 6.92 (1H, s, H-3), 6.76 (2H, s, H-2', H-6"), 6.75 (1H, dd, J=8.4, 2.4 Hz, H-5), 6.52 (1H, d, J=2.4 Hz, H-17"), 6.46 (1H, d, J=9.0 Hz, H-13"), 6.31 (1H, dd, J=8.4, 2.0 Hz, H-19"), 5.77 (1H, brs, H-2"), 5.16 (1H, t, J=7.2 Hz, H-22"), 4.65 (1H, t, J=4.8 Hz, H-4"), 4.10 (1H, br s, H-3"), 3.75 (1H, br s, H-5"), 3.25 (2H, d, J=7.2 Hz, H-21"), 2.48 (1H, m, H-6"), 2.11 (1H, m, H-6"), 1.94 (3H, s, H-7"), 1.71 (3H s, H-24") 1.57 (3H, s H-25");

$^{13}$C NMR (150 MHz, Acetone-d$_6$) δ: 155.4 (C-2), 101.9 (C-3), 121.9 (C-4) 113.2 (C-5) 156.6 (C-6), 98.4 (C-7), 122.7 (C-3a), 156.7 (C-7), 131.6 (C-1'), 113.5 (C-2"), 157.9 (C-3', C-5'), 116.6 (C-4'), 104.9 (C-6') 133.8 (C-1"), 124.4 (C-2"), 33.2 (C-3"), 47.8 (C-4"), 36.6 (C-5"), 32.2 (C-6"), 23.9 (C-7"), 209.9 (C-8"), 113.2 (C-9"), 164.7 (C-10"), 116.0 (C-11"), 163.3 (C-12"), 108.2 (C-13"), 132.2 (C-14"), 122.7 (C-15"), 157.9 (C-16"), 103.6 (C-17"), 157.8 (C-18"), 107.6 (C-19"), 128.8 (C-20"), 22.2 (C-21"), 123.2 (C-22"), 131.8 (C-23"), 17.9 (C-24"), 25.9 (C-25");

HRMS (ESI) calculated for C$_{39}$H$_{37}$O$_9$ [M+H]$^+$ 649.2432, found 649.2405.

2. The Preparation of 18"-O-Methychalcomoracin (13) Using MaDA as Catalyst

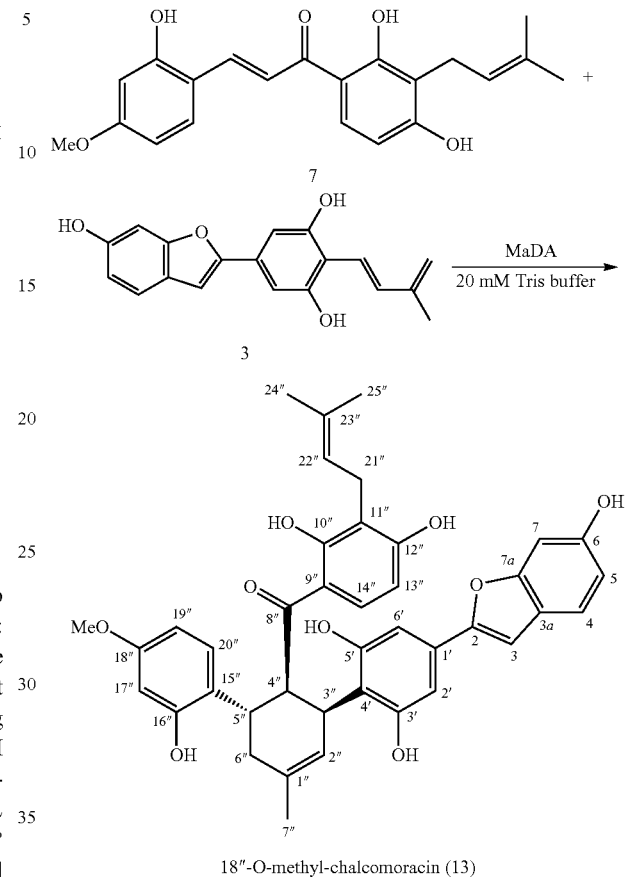

18"-O-methyl-chalcomoracin (13)

Diene precursor S7 (10.0 mg, 0.023 mmol) was added to 1 mL mixture solution of MeOH and H$_2$O (MeOH/H$_2$O=4:1), and then K$_2$CO$_3$ (12.7 mg, 0.092 mmol) was added. The resulting mixture was reacted at room temperature for about 35 min to generate Diene 3 in situ. Then the resulting mixture was added to 98 mL reaction solution (118 nM MaDA in 20 mM Tris-HCl, pH=8.0). To this mixture, Dienophile 7 (6.8 mg dissolved in 1 mL DMSO) was added. The resulting mixture was reacted at 37° C. overnight. The resulting mixture was extracted with ethyl acetate. The organic layers were combined and spin dried, and purified by HPLC to give 18"-O-methychalcomoracin (13) (1.6 mg, 13%).

$[\alpha]_D^{20}$+180.2° (c 0.10, MeOH):

$^1$H NMR (Acetone-d$_6$, 400 MHz) δ: 8.42 (1H, d, J=8.0 Hz, H-14"), 7.35 (1H, d, J=8.4 Hz, H-4), 7.09 (1H, d, J=8.4 Hz, H-20"), 6.93 (1H, s, H-7), 6.93 (1H, s, H-3), 6.77 (2H, s, H-2', H-6'), 6.77 (1H, dd, J=8.4, 2.4 Hz, H-5), 6.55 (1H, d, J=2.4 Hz, H-17"), 6.44 (1H, d, J=9.0 Hz, H-13"), 6.40 (1H, dd, J=8.4, 2.0 Hz, H-19"), 5.78 (1H, br s, H-2"), 5.16 (1H, t, =7.2 Hz, H-22"), 4.65 (1H, t, J=4.2 Hz, H-4"), 4.11 (1H, br s, H-3"), 3.79 (1H, br s, H-5"), 3.25 (2H, d, J=7.2 Hz, H-21"), 2.52 (1H, in, H-6"), 2.24 (1H, m, H-6"), 1.94 (3H, s, H-7"), 1.71 (3H, s, H-24"), 1.57 (3H, s, H-25"), 3.73 (OCH$_3$);

$^{13}$C NMR (Acetone-d$_6$, 100 MHz) δ: 155.3 (C-2), 101.9 (C-3), 121.9 (C-4), 113.0 (C-5), 156.5 (C-6), 98.3 (C-7), 122.6 (C-3a), 156.6 (C-7a), 131.5 (C-1'), 113.9 (C-2'), 157.6

(C-3', C-5'), 117.7 (C-4'), 105.4 (C-6'), 133.8 (C-1"), 124.3 (C-2"), 33.2 (C-3"), 47.7 (C-4"), 36.5 (C-5"), 32.3 (C-6"), 23.8 (C-7"), 209.6 (C-8"), 113.4 (C-9"), 164.6 (C-10"), 115.9 (C-11"), 163.3 (C-12"), 108.1 (C-13"), 132.1 (C-14"), 123.1 (C-15"), 157.7 (C-16"), 102.4 (C-17"), 160.3 (C-18"), 107.1 (C-19") 128.8 (C-20"), 22.2 (C-21"), 123.2 (C-22"), 132.1 (C-23"), 17.8 (C-24"), 25.8 (C-25"), 55.3 (OCH$_3$);

HRMS (ESI) calculated for $C_{40}H_{39}O_9$ [M+H]$^+$ 663.2589, found 663.2549.

3. The Preparation of Guangsangon E (18) Using MaDA as Catalyst

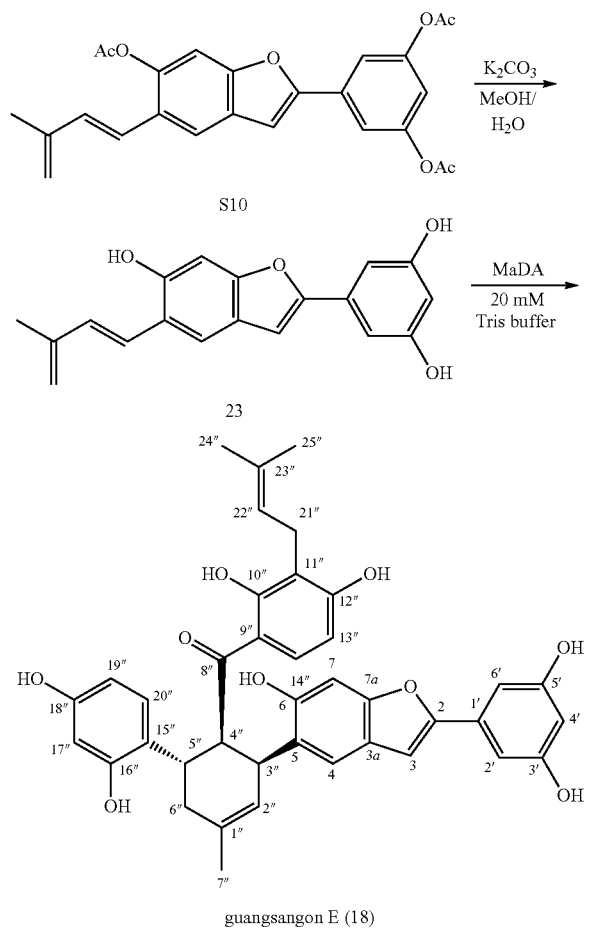

guangsangon E (18)

Diene precursor S10 (9.2 mg, 0.0212 mmol) was added to 1 mL mixture solution of MeOH and H$_2$O (MeOH/H$_2$O=4:1), and then K$_2$CO$_3$ (12.0 mg, 0.0870 mmol) was added. The resulting mixture was reacted at room temperature for about 35 min to generate Diene 23 in situ. Then the resulting solution was added to 48 mL reaction solution (118 nM MaDA in 20 mM Tris-HCl, pH=8.0). To this mixture. Dienophile 1 (5.2 mg, dissolved in 0.26 mL DMSO) was added. The resulting mixture was reacted at 37° C. overnight. The resulting mixture was extracted with ethyl acetate. The organic layers were combined and spin dried, and purified by HPLC to give guangsangon E (13) (6.0 mg, 62%).

$[\alpha]_D^{20}$+376.6° (c 0.11. MeOH);

$^1$H NMR (Acetone-. 600 MHz) δ: 13.04 (1H, s), 9.04 (1H, s), 8.38 (2H, br s), 8.29 (1H, s), 8.02 (1H, d, J=8, 8 Hz, H-14"), 7.99 (1H, s), 7.86 (1H, s), 7.46 (1H, s, H-4), 7.04 (1H, d, J=0.7 Hz, H-3), 6.87 (1H, d, J=8.4 Hz, H-20"), 6.84 (2H, d, J=2.2 Hz, H-2', 6'), 6.82 (1H, s, H-7), 6.44 (1H, d, J=8.8 Hz, H-13"), 6.34 (1H, t, J=2.2 Hz, H-4') 6.27 (1H, d. J=2.4 Hz, H-17"), 6.14 (1H, dd. J=8.4, 2.4 Hz, H-19"), 5.57-5.56 (1H, m, H-2"), 5.17-5.09 (1H, m, H-22"), 4.70 (1H, dd, J=9.7, 5.4 Hz, H-4"), 4.39 (1H, brs, H-3"), 3.71-3.67 (1H, m, H-5"), 3.20 (2H, d. J=7.0 Hz, H-21"), 2.48-2.44 (1H, m, H-6"), 2.07-2.06 (1H, m, H-6"), 1.90 (3H, s, H-7"), 1.67 (3H, s, H-24"), 1.57 (3H, s, H-25");

$^{13}$C NMR (Acetone-d, 150 MHz) δ: 155.1 (C-2), 102.6 (C-3), 123.8 (C-4), 125.5 (C-5), 156.4 (C-6), 97.2 (C-7), 121.9 (C-3a), 154.7 (C-7a), 129.7 (C-1'), 103.7 (C-2'), 159.7 (C-3'), 103.3 (C-4'), 159.7 (C-5'), 103.7 (C-6'), 135.1 (C-1"), 125.5 (C-2"), 37.8 (C-3"), 48.4 (C-4"), 33.5 (C-5"), 37.3 (C-6"), 23.6 (C-7"), 207.0 (C-8"), 115.7 (C-9"), 163.8 (C-10"), 115.3 (C-11"), 161.8 (C-12"), 107.2 (C-13"), 130.5 (C-14"), 123.1 (C-15"), 155.2 (C-16"), 103.8 (C-17"), 156.4 (C-18"), 107.5 (C-19"), 129.7 (C-20"), 22.2 (C-21"), 123.5 (C-22"), 131.1 (C-23"), 17.8 (C-24"), 25.8 (C-25");

HRMS (ESI) calculated for $C_{39}H_{37}O_9$ [M+H]$^+$ 649.2438, found 649.2435.

4. The Preparation of Kuwanol E (21) Using MaDA as Catalyst

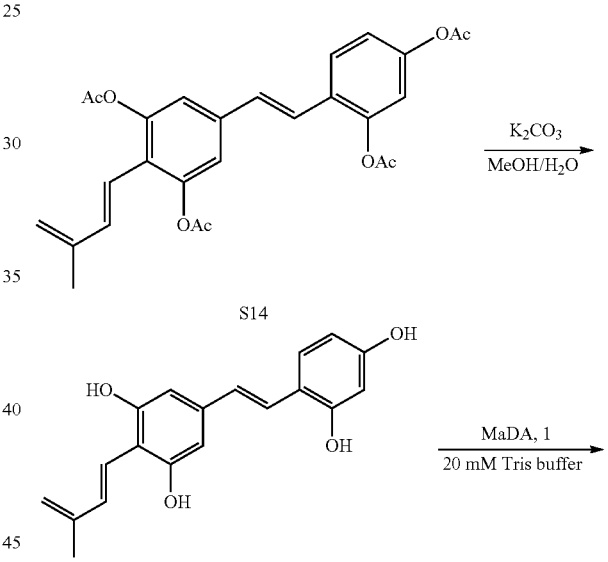

kuwanol E (21)

Acetyl protected precursor S14 (12.5 mg, 0.0261 mmol) was added to 1 mL mixture solution of MeOH and $H_2O$ (MeOH/$H_2O$=4:1), and then $K_2CO_3$ (21.6 mg, 0.1567 mmol) was added. The resulting mixture was reacted at room temperature for about 35 min to generate Diene 25 in situ. Then the resulting solution was added to 98 mL reaction solution (59 nM MaDA in 20 mM Tris-HCl, pH=8.0). To this mixture, Dienophile 1 (7.4 mg, dissolved in 0.34 mL DMSO) was added. The resulting mixture was reacted at 37° C. overnight. The resulting mixture was extracted with ethyl acetate. The organic layers were combined and spin dried, and purified by HPLC to give kuwanol E (21) (6.4 mg, 45%).

$[\alpha]_D^{20}$+160.0° (c 0.03, MeOH);

$^1$H NMR (Acetone-$d_6$, 600 MHz) δ: 13.00 (1H, s), 8.42 (1H, d, J=9.0 Hz, H-14"), 6.76 (1H, d, J=15.6 Hz, H-β), 6.43 (1H, H-6'), 7.21 (1H, d, J=15.6 Hz, H-α), 7.36 (1H, d, J=9.0 Hz, H-6), 6.99 (1H, d, J=8.0 Hz, H-20"), 6.50 (1H, d. J=2.4 Hz, H-17"), 6.40 (1H, d, J=2.4 Hz, H-3), 6.43 (1H, H-2'), 6.35 (1H, dd, J=2.4, 9.0 Hz, H-5), 6.43 (1H, d, J=9.0 Hz, H-13"), 6.31 (1H, dd, J=2.4, 8.4 Hz, H-19"), 5.77 (1H, s, H-2"), 5.17 (1H, t, J=7.2 Hz, H-22"), 4.61 (1H, t, J=4.0 Hz, H-4"), 4.08 (1H br s, H-3"), 3.74 (1H br s, H-5"), 3.27 (2H, d, J=7.2 Hz, H-21"), 2.50 (1H, br d, J=18.0 Hz, H-6"), 2.17 (1H, br d, J=18.0 Hz, H-6"), 1.92 (3H, s, H-7"), 1.71 (3H, s, H-24"), 1.58 (3H, s, H-25");

$^{13}$C NMR (Acetone-dh, 150 MHz): 117.4 (C-1), 157.4 (C-2), 103.5 (C-3), 158.9 (C-4), 108.4 (C-5), 124.8 (C-6), 126.1 (C-α), 126.8 (C-β), 139.2 (C-1'), 106.6 (C-2'), 157.5 (C-3'), 115.8 (C-4'), 157.5 (C-5'), 106.6 (C-6'), 133.6 (C-1"), 123.9 (C-2"), 33.2 (C-3"), 47.9 (C-4"), 36.5 (C-5"), 32.3 (C-3". C-6"), 23.9 (C-7"), 209.9 (C-8"), 113.6 (C-9"), 164.7 (C-10"), 115.9 (C-11"), 164.4 (C-12"), 108.1 (C-13"), 132.3 (C-14"), 122.0 (C-15"), 156.8 (C-16"), 103.5 (C-17"), 157.9 (C-18"), 107.5 (C-19"), 128.8 (C-20"), 22.3 (C-21"), 123.2 (C-22"), 131.6 (C-23"), 17.9 (C-24"), 25.9 (C-25").

HRMS (ESI) calculated for $C_{39}H_{39}O_9$ [M+H]651.2549, found 651.2589.

5. The Preparation of Kuwanon J (19) Using MaDA as Catalyst

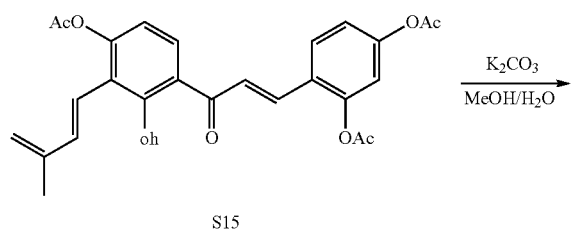

S15

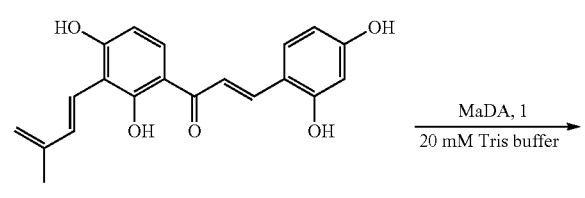

22

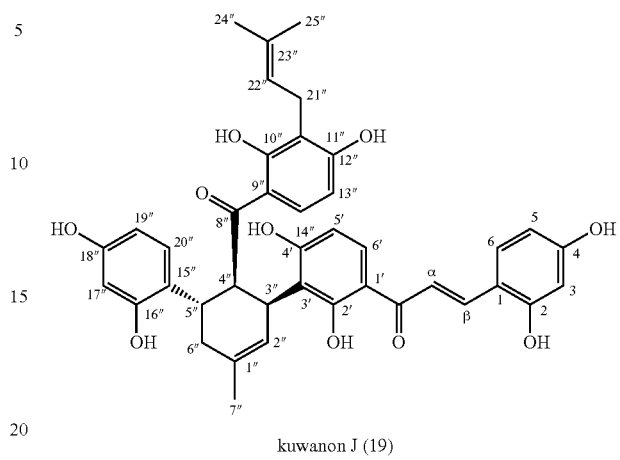

kuwanon J (19)

The acetyl protected precursor S15 (8.5 mg, 0.017 mmol) was added to 1 mL mixture solution of MeOH and $H_2O$ (MeOH/$H_2O$=4:1), and then $K_2CO_3$ (11.2 mg, 0.081 mmol) was added. The resulting mixture was reacted at room temperature for about 35 min to generate Diene 22 in situ. Then the resulting solution was added to 98 mL reaction solution (59 nM MaDA in 20 mM Tris-HCl, pH=8.0). To this mixture, Dienophile 1 (4.8 mg, dissolved in 0.5 mL DMSO) was added. The resulting mixture was reacted at 37° C. overnight. The resulting mixture was extracted with ethyl acetate. The organic layers were combined and spin dried, and purified by HPLC to give kuwanon J (19)(1.8 mg, 19%).

$[\alpha]_D^{20}$+90.0° (c 0.03, MeOH);

$^1$H NMR (Acetone-$d_6$, 600 MHz) S: 14.37 (1H, s), 12.88 (1H, s), 8.39 (1H, d, J=9.0 Hz, H-14"), 8.15 (1H, d, J=15.6 Hz, H-β), 7.85 (1H, d, J=9.0 Hz, H-6'), 7.72 (1H, d, J=15.6 Hz, H-α), 7.66 (1H, d, J=9.0 Hz, H-6), 6.98 (1H, d, J=8.0 Hz, H-20"), 6.53 (1H, d, J=2.4 Hz, H-17"), 6.48 (1H, d. J=2.4 Hz, H-3), 6.43 (1H, d, J=9.0 Hz, H-5'), 6.43 (1H, dd, J=2.4, 9.0 Hz, H-5), 6.36 (1H, d, J=9.0 Hz, H-13"), 6.32 (1H, dd, J=2.4, 8.4 Hz, H-19"), 5.68 (1H, s, H-2"), 5.16 (1H, t, J=7.2 Hz, H-22"), 4.67 (1H, J=4.0 Hz, H-4"), 4.14 (1H br s, H-3"), 3.78 (1H br s, H-5"), 3.26 (2H, d. J=7.2 Hz, H-21"), 2.53 (1H, br d, J=18.0 Hz, H-6"), 2.25 (1H, br d, J=18.0 Hz, H-6"), 1.92 (3H, s, H-7"), 1.71 (3H, s, H-24"), 1.58 (3H, s, H-25");

$^{13}$C NMR (Acetone-$d_6$, 150 MHz) δ: 114.4 (C-1), 160.7 (C-2), 108.0 (C-3), 162.7 (C-4), 103.7 (C-5), 132.3 (C-6), 117.8 (C-α), 141.9 (C-β), 115.6 (C-1'), 163.9 (C-2'), 116.7 (C-3'), 165.8 (C-4'), 110.0 (C-5'), 131.0 (C-6'), 134.7 (C-1"), 123.9 (C-2"), 33.3 (C-3". C-6"), 47.9 (C-4"), 36.7 (C-5"), 23.8 (C-7"), 209.8 (C-8"), 113.9 (C-9"), 164.5 (C-10"), 116.1 (C-11"), 163.9 (C-12"), 109.0 (C-13"), 132.3 (C-14"), 122.9 (C-15"), 157.0 (C-16"), 103.5 (C-17"), 157.8 (C-18"), 107.3 (C-19"), 129.0 (C-20"), 22.4 (C-21"), 123.6 (C-22"), 131.8 (C-23"), 17.9 (C-24"), 25.9 (C-25").

HRMS (ESI) calculated for $C_{40}H_{39}O_{10}$ [M+H]$^+$ 679.2498. found 679.2489.

6. The Preparation of Deoxy-Artonin I (20) Using MaDA as Catalyst

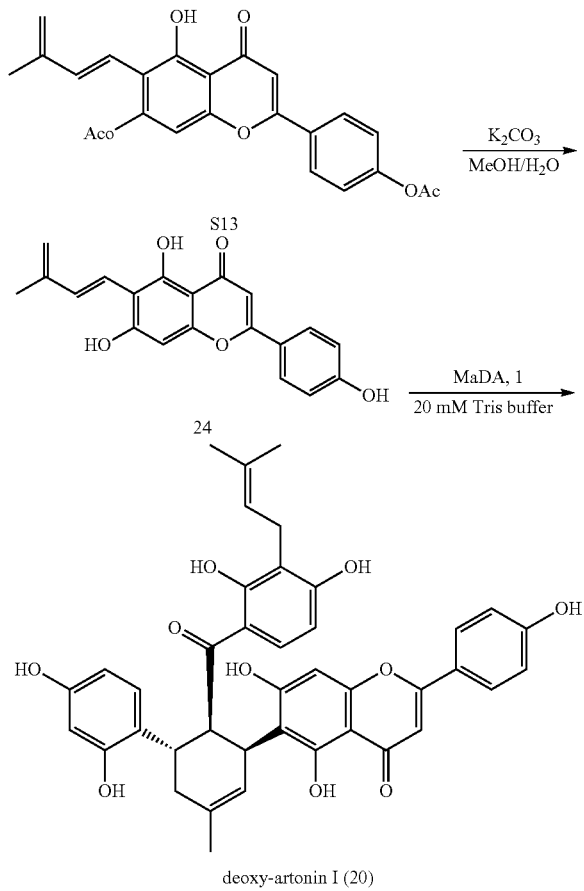

deoxy-artonin I (20)

The acetyl protected precursor S13 (11.0 mg, 0.0262 mmol) was added to 1 mL mixture solution of MeOH and H$_2$O (MeOH/H$_2$O=4:1), and then K$_2$CO$_3$ (11.1 mg, 0.105 mmol) was added. The resulting mixture was reacted at room temperature for about 35 min to generate Diene 24 in situ. Then the resulting solution was added to 150 mL reaction solution (118 nM MaDA in 20 mM Tris-HCl, pH=8.0). To this mixture, Dienophile 1 (7.4 mg, dissolved in 0.37 mL DMSO) was added. The resulting mixture was reacted at 37° C. overnight. The resulting mixture was extracted with ethyl acetate. The organic layers were combined and spin dried, and purified by HPLC to give deoxy-artonin I (20) (6.9 mg, 47%).

$[\alpha]_D^{20}$+176.8° (c 0.23, MeOH):

$^1$H NMR (Acetone-d$_6$, 600 MHz) δ: 13.46 (1H, s), 12.86 (1H, s), 9.42 (1H, br s), 9.22 (1H, br s), 8.89 (1H, d, J=4.9 Hz), 8.68 (1H, br s), 8.38-8.33 (1H, m), 8.10 (1H, s), 7.89 (2H, d, J=8.6 Hz), 7.02-6.98 (2H, m), 6.97 (1H, d, J=8.4 Hz), 6.55 (1H, d, J=2.5 Hz), 6.51 (1H, s), 6.46-6.44 (2H, m), 6.30 (1H, dd, J=2.4, 8.4 Hz), 5.66 (1H, s), 5.15 (1H, ddd, J=1.3, 4.2, 7.1 Hz), 4.66 (1H, t, J=5.1 Hz), 4.15 (1H, s), 3.84 (1H, s), 3.25 (2H, d, J=7.2 Hz), 2.48 (1H, br d, J=17.9 Hz), 2.25 (1H, br d, J=18.0 Hz), 1.92 (3H, s), 1.70 (3H, s), 1.58 (3H, s);

$^{13}$C NMR (Acetone-d$_6$, 150 MHz) S: 209.3, 183.1, 164.9, 164.5, 163.4, 163.3, 161.9, 161.1, 157.9, 156.9, 156.5, 134.8, 132.0, 131.4, 129.2, 128.8, 123.3, 123.1, 123.0, 121.9, 116.8, 115.8, 113.5, 112.4, 108.1, 107.6, 104.8, 103.8, 103.7, 95.8, 47.8, 36.3, 32.9, 32.6, 25.8, 23.8, 22.1, 17.8; HRMS (ESI) calculated for C$_{40}$H$_{37}$O$_{10}$ [M+H]$^+$ 677.2387, found 677.2383.

Example 5 Activity Test of MaDA-Homologous Protein MaDA-1

In the transcriptome of the mulberry cell callus, the inventor not only expressed and verified the function of MaDA, but also carried out the hetero-expression and enzyme activity test of MaDA homologous protein MaDA-1.

1, Amplification of Gene MaDA-1

```
Upstream primer sequence:
                                   (SEQ ID No. 13)
5'-AACCTGTATTTTCAGGGATCCGATCAAATTGGTCATGAAGGC-3'

Downstream primer sequence:
                                   (SEQ ID No. 14)
5'-CTCGAGACTGCAGGCTCTAGATTACCTTTTGTAATGTGGTGAAA

GAG-3'
```

The PCR amplification system and procedures for MaDA-1 were the same as those for MaDA. The nucleotide sequence of MaDA-1 without a signal peptide was shown in SEQ ID No. 9.

2, Construction of pI-Sec-Sumostar-Tev2-MaDA-1 Plasmid and Protein Expression

According to the protocol for constructing pI-sec-SUMOstar-tev2-MaDA plasmid, the MaDA-1 gene sequence was inserted into pI-sec-SUMOstar-tev2 vector and expressed in insect cells. The amino acid sequence of the obtained protein was shown in SEQ ID No. 16. In the sequence of SEQ ID No. 16, the first 20 amino acids (MVSAIVLYVLLAAAAH-SAFA, SEQ ID No.: 22) were the signal peptide contained in the vector itself, HHHHHH, SEQ ID No.: 23, was the 6× his tag,

```
                                      SEQ ID No.: 24
DSEVNQEAKPEVKPETHINLKVSDGSSEIFFKIKKTTPLRRLMEAFA

KRQGKEMDSLTFLYDGIEIQADQTPEDLDMEDNDIIEAHREQIGG,
``` was the SUMO tag, and ENLYFQG, SEQ ID No.: 25, was the TEV restriction site. The purified mature protein expressed by the insect expression system do not contain a signal peptide, and contains 648 amino acids including the SUMO tag, with a theoretical molecular weight (MWt) of 73679.52, and a theoretical isoelectric point (PI) of 5.96. After the N-terminal of the protein was cut off by TEV enzyme, MaDA-1 protein was obtained, and the amino acid sequence of the MaDA-1 protein was shown in SEQ ID No. 10. The MaDA-1 protein contains 524 amino acids, with a theoretical molecular weight (MWt) of 59553.88, and a theoretical isoelectric point (PI) of 7.19. By comparing the amino acid sequences of mature MaDA protein and MaDA-1 protein, it is found that the amino acid sequences of the two proteins are highly similar, as shown in FIG. 17, and the sequence identity is 74%, which indicates that MaDA-1 is one homologous protein of MaDA and may also have the enzymatic activity of catalyzing intermolecular D-A reaction.

3. Enzymatic Activity Test for MaDA-1

The activity of MaDA-1 was tested as follows: to a 97 μL reaction buffer (20 mm Tris-HCl, pH=8.0), 1 μL of Diene 3 (final concentration of 100 μM) and 1 L of Dienophile 1

Figure 18:
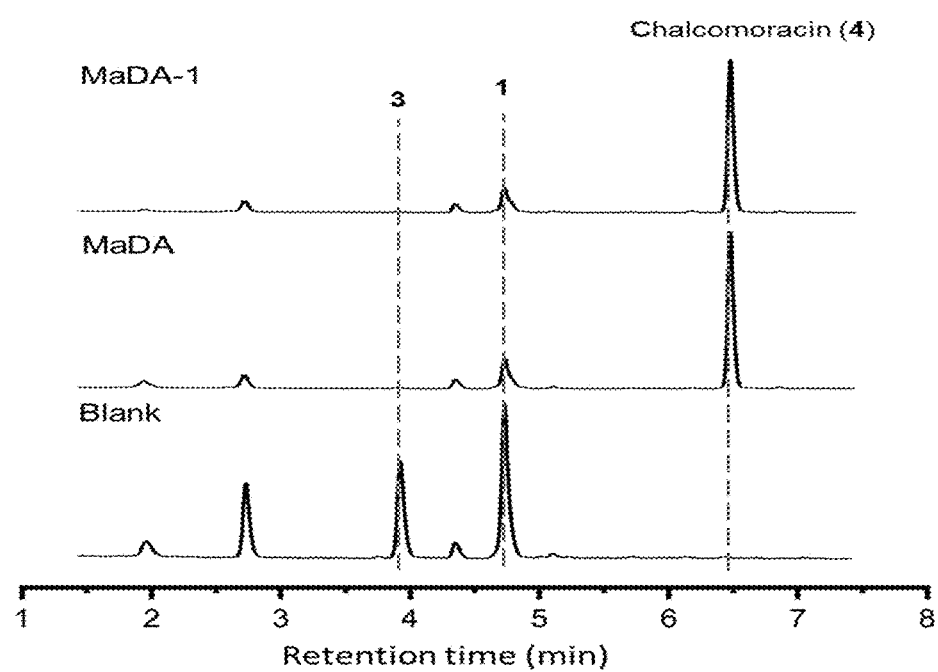
FIG. 18 shows the activity test results of MaDA-1.

(final concentration of 100 μM) were added, and then 1 μL of SUMO-MaDA protein (final concentration 27 nM) or SUMO-MaDA-1 (final concentration 27 nM) was added. The reaction mixture was reacted at 50° C. for 10 min, then quenched by adding 200 μL methanol, and centrifuged at 13,000 rpm for 30 min. The supernatant was analyzed by HPLC. In the control group as blank control, no protein was added. When MaDA or MaDA-1 is added, Diene 3 and Dienophile 1 are almost completely consumed, and chalcomoracin (4) can be produced, as shown in FIG. 18.

Example 6 Enzymatic Activity Test of MaDA-Homologous Protein MaDA-2

In the transcriptome of the cell callus, another homologous protein of MaDA was subjected to heterogenous expression and enzymatic activity test.

1. Amplification of Gene MaDA-2

```
Upstream primer sequence:
                                     (SEQ ID No. 18)
5'-AACCTGTATTTTCAGGGATCCCATGAAGAGTTTCTTCAGTGCC-3'

Downstream primer sequene:
                                     (SEQ ID No. 19)
5'-CTCGAGACTGCAGGCTCTAGATTAATGGTGAAGAATAGGTGG-3'
```

The PCR amplification system and procedures for MaDA-2 were the same as those for MaDA. The nucleotide sequence of MaDA-2 without signal peptide was shown in SEQ ID No. 11.

2. Construction of the pI-Sec-SUMOstar-Tev2-MaDA-2 Plasmid and Protein Expression According to the protocol of constructing pI-sec-SUMOstar-tev2-MaDA plasmid, the above MaDA-2 gene sequence was inserted into pI-sec-SUMOstar-tev2 vector and expressed in insect cells. The amino acid sequence of the obtained protein was as shown in SEQ ID No. 17. In this sequence, the first 20 amino acids (MVSAIVLYVL-LAAAAHSAFA, SEQ ID No.: 22) were the signal peptide contained in the vector itself, HHHHHH, SEQ ID No.: 23,S was the 6× his tag,

```
                                   SEQ ID No.: 24
DSEVNQEAKPEVKPEVKPETHINLKVSDGSSEIFFKIKKTTPLRRLMEAFA

KRQGKEMDSLTFLYDGIEIQADQTPEDLDMEDNDIIEAHREQIGG,
``` was the SUMO tag, and ENLYFQG, SEQ ID No.: 25, was the TEV restriction site. The purified mature protein expressed by the insect expression system do not include a signal peptide, and contains 638 amino acids including the SUMO tag, with a theoretical molecular weight (MWt) of 72487.69, and a theoretical isoelectric point (PI) of 6.13. After the N-terminal of the protein was cut off by TEV, MaDA-2 protein was obtained, and the amino acid sequence of MaDA-2 was shown in SEQ ID No. 12.

MaDA-2 protein contains 513 amino acids, with a theoretical molecular weight (MWt) of 58274.97, and a theoretical isoelectric point (PI) of 8.42. By comparing the amino acid sequences of mature MaDA and MaDA-2, it is found that the amino acid sequences of the two proteins are highly similar, as shown in FIG. 19, and the sequence identity is 72%, which indicates that MaDA-2 is one homologous protein of MaDA and may have the enzymatic activity of catalyzing intermolecular D-A reaction.

3. Activity Test of MaDA-2

Figure 20:
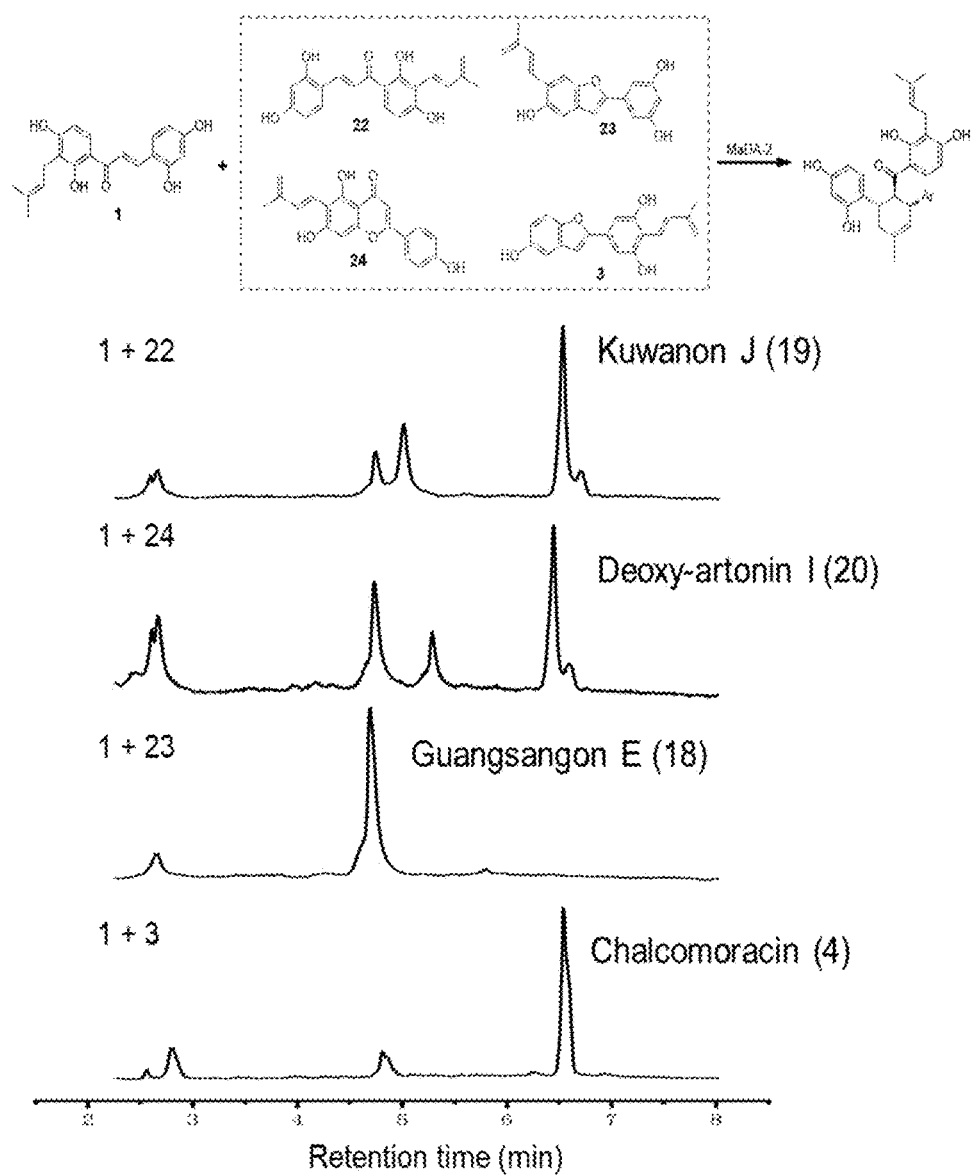
FIG. 20 shows the activity test results for reaction between different dienes and dienophile 1 under catalyzation of MaDA-2.

Under the catalyzation of MaDA-2, the reaction activity between Dienophile 1 and different dienes 3, 22, 23 and 24 was measured following the protocol as follows: to a 98 μL reaction buffer (20 mm Tris-HCl, pH=8.0), 1 μL of Dienophile 1 (final concentration of 100 μM) and 1 μL Diene 3, 22, 23 or 24 (final concentration of 100 μM) were added, and then 1 μL of SUMO-MaDA-2 (final concentration 54 nM) was added. The reaction mixture was reacted at 50° C. for 5 min, then quenched by adding 200 μL methanol. The reaction solution was analyzed by HPLC under the analysis conditions mentioned above, and the results were shown in FIG. 20. It can be seen from FIG. 20 that, MaDA-2 can also catalyze the reaction between Dienophile 1 and different dienes to generate corresponding natural products. In addition, it is also found that MaDA-2 can catalyze the reaction between Dienophile 5 and different dienes to generate corresponding natural products, as shown in FIG. 21. These data show that MaDA-2 and MaDA have the same function, and both of them can catalyze the reaction between Dienophile chalcone 1 and different dienes to produce D-A type natural products or their analogs. However, unlike MaDA, MaDA-2 can recognize Dienophile 5 to generate corresponding natural products or their analogs.

Although the present invention has been described in detail with general description and specific embodiments, it is obvious to a person skilled in the art that some modifications or improvements can be made on the basis of the present invention. Therefore, these modifications or improvements made without deviating from the spirit of the present invention belong to the scope of protection claimed in the present invention.

What is claimed is:

1. A Diels-Alderase protein comprising SEQ ID No. 10 (corresponding to MaDA-1) and SEQ ID No. 12 (corresponding to MaDA 2).

2. A method for catalyzing Diels-Alder reaction in an isolated insect cell, an isolated animal cell or an isolated plant cell, wherein the method comprises using bio-material containing a Diels-Alderase protein comprising SEQ ID No.10 (corresponding to MaDA-1) and SEQ ID No. 12 (corresponding to MaDA 2).

3. The method according to claim 2, wherein, the Diels-Alder reaction is performed for generating natural products containing 6-membered ring skeleton or natural products with endo-configuration.

4. The method according to claim 2, wherein, the bio-material is an expressing kit, a plasmid, a vector, a microorganism, an insect cell, an animal cell or a plant cell.

5. The method according to claim 2, wherein, in the Diels-Alder reaction, dienophiles and dienes are used as substrates.

6. The method according to claim 5, wherein, the dienophiles are chalcone or its derivatives, and the dienes are dehydroprenyl flavonoids, dehydroprenyl stilbenes, dehydroprenyl chalcones, or dehydroprenyl benzofurans.

7. The method according to claim 2, wherein, in the Diels-Alder reaction, reaction temperature is 50° C., and pH is 8.0.

8. The method according to claim 2, wherein, the Diels-Alder reaction is performed for generating natural flavonoid products or analogues thereof.

* * * * *

UNITED STATES PATENT AND TRADEMARK OFFICE
CERTIFICATE OF CORRECTION

PATENT NO. : 11,293,015 B2
APPLICATION NO. : 16/951916
DATED : April 5, 2022
INVENTOR(S) : Xiaoguang Lei et al.

Page 1 of 1

It is certified that error appears in the above-identified patent and that said Letters Patent is hereby corrected as shown below:

On the Title Page (30), in Foreign Application Priority Data, insert therefor -- November 19, 2019 (CN) 2019-11136243.7 --.

Signed and Sealed this
Thirteenth Day of September, 2022

Katherine Kelly Vidal
*Director of the United States Patent and Trademark Office*